US008101647B2

(12) United States Patent
Chafeev et al.

(10) Patent No.: US 8,101,647 B2
(45) Date of Patent: *Jan. 24, 2012

(54) SPIRO-OXINDOLE COMPOUNDS AND THEIR USE AS THERAPEUTIC AGENTS

(75) Inventors: Mikhail Chafeev, Burnaby (CA); Sultan Chowdhury, Surrey (CA); Lauren Fraser, Surrey (CA); Jianmin Fu, Coquitlam (CA); Jonathan Langille, Quaker Hill, CT (US); Shifeng Liu, Coquitlam (CA); Jianyu Sun, San Manteo, CA (US); Shaoyi Sun, Coquitlam (CA); Serguei Sviridov, Burnaby (CA); Mark Wood, Port Moody (CA); Alla Zenova, Vancouver (CA)

(73) Assignee: Xenon Pharmaceuticals Inc., Burnaby, B.C. (CA)

( * ) Notice: Subject to any disclaimer, the term of this patent is extended or adjusted under 35 U.S.C. 154(b) by 109 days.

This patent is subject to a terminal disclaimer.

(21) Appl. No.: 12/577,799

(22) Filed: Oct. 13, 2009

(65) Prior Publication Data

US 2011/0112162 A9 May 12, 2011

Related U.S. Application Data

(60) Provisional application No. 61/106,410, filed on Oct. 17, 2008.

(51) Int. Cl.
*C07D 491/10* (2006.01)
*A61K 31/404* (2006.01)

(52) U.S. Cl. .................. 514/412; 548/410
(58) Field of Classification Search .......... 514/412; 548/410
See application file for complete search history.

(56) References Cited

U.S. PATENT DOCUMENTS

| 3,189,617 A | 6/1965 | Archer et al. ............ 260/319 |
| 3,723,459 A | 3/1973 | Paragamian ............ 260/325 |
| 3,845,770 A | 11/1974 | Theeuwes et al. ......... 128/260 |
| 4,045,576 A | 8/1977 | Welstead, Jr. et al. ...... 424/309 |
| 4,326,525 A | 4/1982 | Swanson et al. ........... 128/260 |
| 4,438,130 A | 3/1984 | Kaplan ..................... 424/274 |
| 4,440,785 A | 4/1984 | Walsh ...................... 424/317 |
| 4,670,566 A | 6/1987 | Walsh ...................... 548/485 |
| 4,886,788 A | 12/1989 | Skuballa et al. ............. 514/58 |
| 4,935,446 A | 6/1990 | Imaki et al. ............... 514/530 |
| 5,023,265 A | 6/1991 | Scherlock et al. .......... 514/300 |
| 5,116,854 A | 5/1992 | Marfat ..................... 514/365 |
| 5,182,289 A | 1/1993 | Ting et al. ................ 514/278 |
| 5,278,162 A | 1/1994 | Wilkerson ............... 514/252 |
| 5,296,478 A | 3/1994 | Teleha ................... 514/235.2 |
| 5,453,516 A | 9/1995 | Fischer et al. ............. 548/543 |
| 5,663,431 A | 9/1997 | Di Malta et al. ........... 562/828 |
| 5,686,624 A | 11/1997 | Di Malta et al. ........... 548/410 |
| 5,696,145 A | 12/1997 | Foulon et al. ............. 514/409 |
| 5,723,625 A | 3/1998 | Keplinger et al. .......... 548/408 |
| 5,726,322 A | 3/1998 | Di Malta et al. ........... 548/410 |
| 5,728,723 A | 3/1998 | Di Malta et al. ........... 514/418 |
| 5,763,471 A | 6/1998 | Fourtillan et al. .......... 514/409 |
| 5,767,128 A | 6/1998 | Guillaumet et al. ........ 514/300 |
| 5,776,936 A | 7/1998 | Lee et al. ................. 514/250 |
| 5,849,780 A | 12/1998 | Di Malta et al. ........... 514/409 |
| 5,994,350 A | 11/1999 | Foulon et al. ............ 514/232.8 |
| 6,046,341 A | 4/2000 | Foulon et al. ............. 548/411 |
| 6,090,818 A | 7/2000 | Foulon et al. ............. 514/278 |
| 6,110,969 A | 8/2000 | Tani et al. ................ 514/530 |
| 6,225,347 B1 | 5/2001 | Buchmann et al. ......... 514/530 |
| 6,235,780 B1 | 5/2001 | Ohuchida et al. .......... 514/530 |
| 6,262,293 B1 | 7/2001 | Tani et al. ................. 560/18 |
| 6,288,119 B1 | 9/2001 | Ohuchida et al. .......... 514/573 |
| 6,355,627 B1 | 3/2002 | Ishida et al. ............... 514/58 |
| 6,414,153 B1 | 7/2002 | Kelly et al. ............... 546/113 |
| 6,670,357 B2 | 12/2003 | Leftheris et al. .......... 514/218 |
| 6,964,973 B2 | 11/2005 | Zhi et al. ................. 514/312 |
| 7,368,470 B2 | 5/2008 | Sundermann et al. ...... 514/415 |
| 7,700,641 B2 * | 4/2010 | Chafeev et al. ........... 514/409 |
| 7,799,798 B2 | 9/2010 | Chafeev et al. ........... 514/278 |
| 2002/0039790 A1 | 4/2002 | Keplinger et al. .......... 435/371 |
| 2004/0038970 A1 | 2/2004 | Thurieau et al. .......... 514/234.2 |
| 2004/0167224 A1 | 8/2004 | Ozaki et al. .............. 514/616 |
| 2005/0004137 A1 | 1/2005 | Romano ............... 514/253.07 |
| 2005/0004138 A1 | 1/2005 | Romano ............... 514/253.07 |
| 2005/0014764 A1 | 1/2005 | Romano et al. ......... 514/253.06 |
| 2005/0020617 A1 | 1/2005 | Bastian et al. ............. 514/300 |
| 2005/0038036 A1 | 2/2005 | Romano et al. ......... 514/253.06 |

(Continued)

FOREIGN PATENT DOCUMENTS

CA 2095718 A1 5/1992
(Continued)

OTHER PUBLICATIONS

Adams et al., "Bicyclic N-Hydroxyurea Inhibitors of 5-Lipoxygenase: Pharmacodynamic, Pharmacokinetic, and in Vitro Metabolic Studies Characterizing *N*-Hydroxy-*N*-(2,3-dihydro-6-(phenylmethoxy)-3-benzofuranyl)urea," *J. Med. Chem.* 39(26): 5035-5046, 1996. Akai, "Development of Novel Asymmetric Reactions Oriented to Next-Generation Enzymatic Organic Syntheses," *Yakugaku Zasshi 123*(11): 919-931, 2003.
Al-Thebeiti and El-Zohry, "A Facile Route for the Synthesis of Some New Spiro[indoline-3,3'-indan]-2,1'-dione Derivatives," *Heterocycles 41*(11): 2475-2480, 1995.
Alabaster et al., "The Synthesis of 5-Substituted 2,3-Dihydrobenzofurans," *Synthesis 12*: 950-952, Dec. 1988.
Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.
Alper et al., "Eine neuartige Methode zur Synthese von Spiro[pyrrolidin-3,3'-oxindolen]: katalysierte Ringerweiterung von Cyclopropanen mit Aldiminen," *Angew. Chem. 111*(21): 3379-3381, 1999.

(Continued)

*Primary Examiner* — Kamal Saeed
*Assistant Examiner* — Janet L Coppins
(74) *Attorney, Agent, or Firm* — Seed IP Law Group PLLC

(57) ABSTRACT

This invention is directed to spiro-oxindole compounds, as stereoisomers, enantiomers, tautomers thereof or mixtures thereof; or pharmaceutically acceptable salts, solvates or prodrugs thereof, for the treatment and/or prevention of sodium channel-mediated diseases or conditions, such as pain.

37 Claims, No Drawings

U.S. PATENT DOCUMENTS

| | | | |
|---|---|---|---|
| 2005/0075351 A1 | 4/2005 | Berg et al. | 514/266.2 |
| 2005/0153998 A1 | 7/2005 | Ito et al. | 514/278 |
| 2005/0159473 A1 | 7/2005 | Sall et al. | 514/414 |
| 2005/0171186 A1 | 8/2005 | Fensome et al. | 514/418 |
| 2005/0256110 A1 | 11/2005 | Collins et al. | 514/224.2 |
| 2005/0256144 A1 | 11/2005 | Kath et al. | 514/275 |
| 2006/0247441 A1 | 11/2006 | Wilk | 548/408 |
| 2007/0049269 A1 | 3/2007 | Broka et al. | 514/269 |
| 2007/0072831 A1 | 3/2007 | Cai et al. | 514/80 |
| 2007/0105820 A1 | 5/2007 | Chafeev et al. | 514/80 |
| 2007/0299102 A1 | 12/2007 | Felding et al. | 514/299 |
| 2008/0103151 A9 | 5/2008 | Chafeev et al. | 514/248 |
| 2010/0125072 A1 | 5/2010 | Chafeev et al. | 514/232.8 |
| 2010/0130487 A1 | 5/2010 | Chafeev et al. | 514/232.8 |
| 2010/0137299 A1 | 6/2010 | Chafeev et al. | 514/232.8 |
| 2010/0160291 A1 | 6/2010 | Chafeev et al. | 514/211.09 |
| 2010/0160362 A1 | 6/2010 | Cadieux et al. | 514/278 |
| 2010/0173967 A1 | 7/2010 | Chafeev et al. | 514/409 |
| 2010/0331386 A1 | 12/2010 | Chafeev et al. | 514/409 |
| 2011/0034500 A1 | 2/2011 | Chafeev et al. | 514/278 |
| 2011/0086899 A1 | 4/2011 | Winters et al. | 514/409 |
| 2011/0087027 A1 | 4/2011 | Cadieux et al. | 546/15 |

FOREIGN PATENT DOCUMENTS

| | | |
|---|---|---|
| CA | 2107348 A1 | 7/1993 |
| CA | 2129215 A1 | 1/1995 |
| CA | 2 274 898 A1 | 6/1998 |
| CA | 2 450 550 A1 | 1/2003 |
| CA | 2 466 915 A1 | 8/2003 |
| CA | 2 487 494 A1 | 12/2003 |
| CA | 2 235 686 C | 6/2007 |
| DE | 1 956 237 A | 5/1971 |
| DE | 2113343 A1 | 9/1972 |
| EP | 0 147 805 A2 | 7/1985 |
| EP | 0 164 860 A1 | 12/1985 |
| EP | 0 175 551 A1 | 3/1986 |
| EP | 0 608 058 A1 | 7/1994 |
| EP | 1 422 217 A2 | 5/2004 |
| EP | 1 557 166 A1 | 7/2005 |
| FR | 2 722 195 A1 | 1/1996 |
| JP | 10-95766 A | 4/1998 |
| WO | WO 86/03749 A1 | 7/1986 |
| WO | WO 91/01306 A1 | 2/1991 |
| WO | WO 91/04974 A1 | 4/1991 |
| WO | WO 91/06545 A1 | 5/1991 |
| WO | WO 92/09577 A1 | 6/1992 |
| WO | WO 93/12786 A1 | 7/1993 |
| WO | WO 93/15051 A1 | 8/1993 |
| WO | WO 94/03427 A1 | 2/1994 |
| WO | WO 95/06688 A1 | 3/1995 |
| WO | WO 95/14667 A1 | 6/1995 |
| WO | WO 97/15556 A1 | 5/1997 |
| WO | WO 97/36895 A1 | 10/1997 |
| WO | WO 98/25901 A1 | 6/1998 |
| WO | WO 98/50016 A2 | 11/1998 |
| WO | WO 00/06556 A1 | 2/2000 |
| WO | WO 00/71129 A1 | 11/2000 |
| WO | WO 01/38564 A2 | 5/2001 |
| WO | WO 01/38564 A3 | 5/2001 |
| WO | WO 01/74775 A1 | 10/2001 |
| WO | WO 02/30868 A1 | 4/2002 |
| WO | WO 02/38544 A2 | 5/2002 |
| WO | WO 03/000677 A1 | 1/2003 |
| WO | WO 03/037274 A2 | 5/2003 |
| WO | WO 03/037890 A2 | 5/2003 |
| WO | WO 03/064425 A1 | 8/2003 |
| WO | WO 03/078394 A1 | 9/2003 |
| WO | WO 03/106457 A1 | 12/2003 |
| WO | WO 04/000225 A2 | 12/2003 |
| WO | WO 04/000227 A2 | 12/2003 |
| WO | WO 2004/048320 A1 | 6/2004 |
| WO | WO 2005/011657 A2 | 2/2005 |
| WO | WO 2005/016913 A1 | 2/2005 |
| WO | WO 2005/019208 A1 | 3/2005 |
| WO | WO 2005/035498 A1 | 4/2005 |
| WO | WO 2005/092304 A2 | 10/2005 |
| WO | WO 2005/092895 A2 | 10/2005 |
| WO | WO 2005/097107 A2 | 10/2005 |
| WO | WO 2005/097122 A2 | 10/2005 |
| WO | WO 2005/099689 A1 | 10/2005 |
| WO | WO 2005/104711 A2 | 11/2005 |
| WO | WO 2005/105753 A2 | 11/2005 |
| WO | WO 2005/110992 A1 | 11/2005 |
| WO | WO 2005/111024 A1 | 11/2005 |
| WO | WO 2006/012173 A1 | 2/2006 |
| WO | WO 2006/017075 A1 | 2/2006 |
| WO | WO 2006/023107 A1 | 3/2006 |
| WO | WO 2006/023109 A1 | 3/2006 |
| WO | WO 2006/049290 A1 | 5/2006 |
| WO | WO 2006/055752 A2 | 5/2006 |
| WO | WO 2006/087019 A1 | 8/2006 |
| WO | WO 2006/091646 A2 | 8/2006 |
| WO | WO 2006/110654 A1 | 10/2006 |
| WO | WO 2006/110917 A2 | 10/2006 |
| WO | WO 2006/113864 A2 | 10/2006 |
| WO | WO 2006/113875 A2 | 10/2006 |
| WO | WO 2008/046046 A1 | 4/2008 |
| WO | WO 2008/046049 A1 | 4/2008 |
| WO | WO 2008/046065 A1 | 4/2008 |
| WO | WO 2008/046082 A2 | 4/2008 |
| WO | WO 2008/046083 A2 | 4/2008 |
| WO | WO 2008/046084 A2 | 4/2008 |
| WO | WO 2008/046087 A2 | 4/2008 |
| WO | WO 2008/060789 A2 | 5/2008 |
| WO | WO 2008/117050 A1 | 10/2008 |
| WO | WO 2010/045197 A1 | 4/2010 |
| WO | WO 2010/045251 A2 | 4/2010 |
| WO | WO 2010/053998 A1 | 5/2010 |
| WO | WO 2010/078307 A1 | 7/2010 |
| WO | WO 2010/132352 A2 | 11/2010 |
| WO | WO-2011/002708 * | 1/2011 |
| WO | WO 2011/002708 A1 | 1/2011 |
| WO | WO 2011/047173 A2 | 4/2011 |
| WO | WO 2011/047174 A1 | 4/2011 |

OTHER PUBLICATIONS

Alper et al., "Facile, Novel Methodology for the Synthesis of Spiro[pyrrolidin-3,3'- oxindoles]: Catalyzed Ring Expansion Reactions of Cyclopropanes by Aldimines," *Angew. Chem. Int. Ed. 38*(21): 3186-3189, 1999.

Anger et al., "Medicinal Chemistry of Neuronal Voltage-Gated Sodium Channel Blockers," *Journal of Medicinal Chemistry 44*(2): 115-137, Jan. 18, 2001.

Autrey and Tahk, "The Synthesis and Stereochemistry of Some Isatylideneacetic Acid Derivatives," *Tetrahedron 23*: 901-917, 1967.

Bacher et al., "Oxindole alkaloids from *Uncaria tomentosa* induce apoptosis in proliferating, G0/G1-arrested and bcl-2-expressing acute lymphoblastic leukaemia cells," *British Journal of Haematology 132*: 615-622, 2005.

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem. 49*: 3784-3790, 1984.

Basavaiah et al., "TiCl$_4$ catalyzed tandem construction of C-C and C-O bonds: a simple and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol. 81*: 613-642, May 1983.

Bennett and Xie, "A peripheral mononeuropathy in rat that produces disorders of pain sensation like those seen in man," *Pain 33*: 87-107, 1988.

Beyersbergen Van Henegouwen et al., "First Total Synthesis of *ent*-Gelsedine via a Novel Iodide-Promoted Allene *N*-Acyliminium Ion Cyclization," *J. Org. Chem. 65*(24): 8317-8325, 2000.

Beyersbergen Van Henegouwen et al., "Total Synthesis of (+)-Gelsedine," *Angw. Chem. Int. Ed. 38*(15): 2214-2217, 1999.

Billert and Beckert, "Beiträge zur Chemie der Pyrido[1,2-α]pyrazine—Reaktivität gegenüber Heterocumulenen der Kohlensäurereihe und Ketenen," *J. Prakt. Chem. 341*(4): 332-341, 1999.

Binder et al., "Disease mechanisms in neuropathic itch," *Nature Clinical Practice/Neurology 4*(6): 329-337, Jun. 2008.

Blair and Bean, "Roles of Tetrodotoxin (TTX)-Sensitive Na+ Current, TTX-Resistant Na+ Current, and Ca2+ Current in the Action Potentials of Nociceptive Sensory Neurons," *Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Rio-Organic Chemistry* 7: 1751-1761, 1979.

Brackenbury and Djamgoz, "Activity-dependent regulation of voltage-gated Na+ channel expression in Mat-LyLu rat prostate cancer cell line," *J. Physiol.* 573.2: 343-356, 2006.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Braude and Lindwall, "Condensations of Isatin with Acetone by the Knoevenagel Method," *Journal of the American Chemical Society* 55: 325-327, Jan. 1933.

Caldwell et al., "Sodium channel $Na_v1.6$ is localized at nodes of Ranvier, dendrites, and synapses," *PNAS* 97(10): 5616-5620, May 9, 2000.

Cañas-Rodriguez and Leeming, "N-Phenyl-2-indolinones and N-Phenylindolines. A New Class of Antidepressant Agents," *Journal of Medicinal Chemistry* 15(7): 762-770, 1972.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Cestèle and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European Journal of Medicinal Chemistry* 40: 1143-1148, 2005.

Chaplan et al., "Quantitative assessment of tactile allodynia in the rat paw," *Journal of Neuroscience Methods* 53: 55-63, 1994.

Chioni et al., "A novel adhesion molecule in human breast cancer cells: Voltage-gated Na+ channel β1 subunit," *The International Journal of Biochemistry & Cell Biology* 41: 1216-1227, 2009.

Chung and Chung, "Sodium channels and neuropathic pain," *Novartis Found Symposium* 261: 19-31, 2004.

Clare et al., "Voltage-gated sodium channels as therapeutic targets," *Drug Discovery Today* 5(11): 506-520, Nov. 2000.

Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.

Coppola, "*N*-Arylation of Isatins. A Direct Route to *N*-Arylisatoic Anhydrides," *J. Heterocyclic Chem.* 24: 1249-1251, Sep./Oct. 1987.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cox et al., "An *SCN9A* channelopathy causes congenital inability to experience pain," *Nature* 444: 894-898, Dec. 14, 2006.

Craner et al., "Molecular changes in neurons in multiple sclerosis: Altered axonal expression of $Na_v1.2$ and $Na_v1.6$ sodium channels and $Na^+/Ca^{2+}$ exchanger," *PNAS* 101(21): 8168-8173, May 25, 2004.

Cravotto et al., "Azomethine Ylide Cycloaddition/Reductive Heterocyclization Approach to Oxindole Alkaloids: Asymmetric Synthesis of (—)-Horsfiline," *J. Org. Chem.* 66(25): 8447-8453, 2001.

Creveling and Daly, "Batrachotoxinin A [3H]Benzoate Binding to Sodium Channels," *Methods in Neurosciences* 8: 25-37, 1992.

Cube et al., "3-(2-Ethoxy-4-{4[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.

Dallacker and Sanders, "Darstellung and Reaktionen von 5-(3'-Hydroxy-oxindol-3'-yl)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Dib-Hajj et al., "Genetics and Molecular Pathophysiology of $Na_v1.7$-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Do and Bean, "Subthreshold Sodium Currents and Pacemaking of Subthalamic Neurons: Modulation by Slow Inactivation," *Neuron* 39: 109-120, Jul. 3, 2003.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of *N*-Aryldiazoamides. An Efficient Synthesis of 2(3*H*)-Indolinones," *J. Org. Chem* 53(5): 1017-1022, 1988.

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.

Dutton et al., "A Total Synthesis of Gelsemine: Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)benzotriazoles," *Tetrahedron* 55: 11927-11942, 1999.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Ettinger and Argoff, "Use of Antiepileptic Drugs for Nonepileptic Conditions: Psychiatric Disorders and Chronic Pain," *Neurotherapeutics: The Journal of the American Society for Experimental NeuroTherapeutics* 4:75-83, Jan. 2007.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.

Feldman and Vidulova, "Extending Pummerer Reaction Chemistry. Application to the Oxidative Cuclization of Indole Derivatives," *Organic Letters* 6(11): 1869-1871, 2004.

Fishman et al., "Intravenous Lidocaine for Treatment-resistant Pruritus," *American Journal of Medicine* 102: 584-585, Jun. 1997.

Flanagan et al., "Radical cyclisation reactions with indoles," *Tetrahedron Letters* 44: 1795-1798, 2003.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Fuchs and See, "Basolateral amygdala inactivation abolishes conditioned stimulus- and heroin-induced reinstatement of extinguished heroin-seeking behavior in rats," *Psychopharmacology* 160: 425-433, 2002.
Fuji et al., "Direct Asymmetric Synthesis of Quaternary Carbon Centers via Addition-Elimination Process: Nitroolefination of α-Substituted δ-Lactones," *J. Am. Chem. Soc. 111*: 7921-7925, 1989.
Fujita et al., "The Beckmann Rearrangement by Means of Phosphoryl Chloride/N,N-Dimethylacetamide; A Novel and Convenient Method for Preparing Benzoxazoles," *Synthesis* 68-69, Jan. 1982.
Gálvez and García, "Synthesis of Isomeric β-Haloethylthienopyrroles," *J. Heterocyclic Chem. 21*: 393-395, Mar.-Apr. 1984.
Ganguly et al., "Solution- and solid-phase synthesis of enantiomerically pure spiro oxindoles," *Tetrahedron Letters 43*: 8981-8983, 2002.
Ganguly et al., "Synthesis of heterocyclic compounds using radical reactions and evidence for the formation of spiro radical intermediates," *Tetrahedron Letters 45*: 883-886, 2004. See also Ganguly et al., "Corrigendum to 'Synthesis of heterocyclic compounds using radical reactions and evidence for the formation of spiro radical intermediates,'" [*Tetrahedron Letters 45*: 883-886, 2004], *Tetrahedron Letters 45*: 3835, 2004.
Garden et al., "Investigation of the selective reduction of isatin derivatives. Synthesis of α-hydroxyacetophenone derivatives and ethyl spiro-3,3-(ethylenedioxy)-2-hydroxyindoline carboxylates," *Tetrahedron Letters 44*: 7617-7621, 2003.
Garden et al., "A versatile synthetic methodology for the synthesis of tryptophols," *Tetrahedron 58*: 8399-8412, 2002.
Goldberg et al., "Loss-of-function mutations in the $Na_v1.7$ gene underlie congenital indifference to pain in multiple human populations," *Clin. Genet. 71*: 311-319, 2007.
González-López De Turiso and Curran, "Radical Cyclization Approach to Spirocyclohexadienones," *Organic Letters 7*(1): 151-154, 2005.
Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters 37*(5): 695-698, 1996.
Grigg et al., "Spiro-oxindoles via bimetallic [Pd(0)/Ag(I)] catalytic intramolecular Heck-1,3-dipolar cycloaddition cascade reactions," *Tetrahedron Letters 43*: 2605-2608, 2002.
Grigoryan et al., "Synthesis and antispasmodic activity of spiro[β-carbolineindolones] and spiro[indoleindolo[2,3-c]azepinones]," *Hayastani Kimiakan Handes 58*(3): 100-104, 2005, Caplus Database Accession No. 2005:876436, 4 pages, Abstract only.
Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience 23*(26): 8881-8892, Oct. 1, 2003.
Hamann et al., "Motor disturbances in mice with deficiency of the sodium channel gene Scn8a show features of human dystonia," *Experimental Neurology 184*: 830-838, 2003.
Haufe et al., "The promiscuous nature of the cardiac sodium current," *Journal of Molecular and Cellular Cardiology 42*: 469-477, 2007.
Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron 39*(23): 1981-1986, 1983.
Ikoma et al., "The neurobiology of itch," *Nature Reviews Neuroscience 7*: 535-547, Jul. 2006.
Inan et al., "Inhibitory effect of lidocaine on pain and itch using formalin-induced nociception and 5'-guanidinonaltrindole-induced scratching models in mice: Behavioral and neuroanatomical evidence," *European Journal of Pharmacology 616*: 141-146, 2009.
Iranpoor et al., "A novel method for the highly efficient synthesis of 1,2-benzisoxazoles under neutral conditions using the $Ph_3P/DDQ$ system," *Tetrahedron Letters 47*: 8247-8250, 2006.
Ishiyama et al., "Synthesis of Arylboronates via the Palladium(0)-Catalyzed Cross-Coupling Reaction of Tetra(alkoxo)diborons with Aryl Triflates," *Tetrahedron Letters 38*(19): 3447-3450, 1997.
Islip and White, "236. Some Reactions of 2-(3-Oxindolyl)ethylamines," *Journal of the Chemical Society* 1201-1204, 1964.

Itoh et al., "Introduction of a Hydroxy Group at the Para Position and N-Iodophenylation of N-Arylamides Using Phenyliodine(III) Bis(Trifluoracetate)," *J. Org. Chem. 67*: 74247428, 2002.
Jarvis et al., "A-803467, a potent and selective $Na_v1.8$ sodium channel blocker, attenuates neuropathic and inflammatory pain in the rat," *PNAS 104*(20): 8520-8525, May 15, 2007.
Jorgensen and Berteau, "Thyroxine Analogs. 21. o- and m-L-Thyroxine and Related Compounds," *Journal of Medicinal Chemistry 14*(12): 1199-1202, 1971.
Julian et al., "Studies in the Indole Series. VI. On the Synthesis of Oxytryptophan and Further Studies of 3-Alkylation of Oxindoles," *Journal of the American Chemical Society 57*: 2026-2029, Nov. 1935.
Julian et al., "Studies in the Indole Series. VIII. Yohimbine (Part 1). The Mechanism of Dehydrogenation of Yohimbine and Related Compounds," *Journal of the American Chemical Society 70*: 174-179, Jan. 1948.
Kaila et al., "Synthesis and Biological Evaluation of Quinoline Salicylic Acids as P-Selectin Antagonists," *J. Med. Chem. 50*: 21-39, 2007.
Kamara et al., "The First Direct Transformation of 2,2'-Dihydroxychalcones into Coumestans," *Tetrahedron 55*: 861-868, 1999.
Kamiya et al., "A Nonsense Mutation of the Sodium Channel Gene SCN2A in a Patient with Intractable Epilepsy and Mental Decline," *Journal of Neuroscience 24*(11): 2690-2698, Mar. 17, 2004.
Kang et al., "Pteropodine and isopteropodine positively modulate the function of rat muscarinic $M_1$ and $5-HT_2$ receptors expressed in Xenopus oocyte," *European Journal of Pharmacology 444*: 39-45, 2002.
Karp et al., "Preparation of 4-Hydroxy-2-trifluoromethylthiophene: A Novel Bioisostere of α,α,α-Trifluoro-m-cresol," *Synthesis 8*: 1078-1080, 2000.
Kende et al., "Intramolecular Radical Cyclization of Phenolic Enolates," *J. Am. Chem. Soc. 110*: 2210-2218, 1988.
Kim et al., "BACE1 regulates voltage-gated sodium channels and neuronal activity," *Nature Cell Biology 9*(7): 755-764, Jul. 2007.
Kim et al., "Design, synthesis, and evaluation of dioxane-based antiviral agents targeted against the Sindbis virus capsid protein," *Bioorganic & Medicinal Chemistry Letters 15*: 3207-3211, 2005.
King et al., "Hydroxy-quinoxalines and -phenazines, and Experiments on the Preparation of Hydroxyquinoxaline Di-N-oxides," *J. Chem. Soc.* 3012-3016, 1949.
Kirmse et al., "Intramolecular Reactivity of Arylcarbenes: Derivatives of o-Tolylcarbene," *J. Org. Chem. 59*: 3821-3829, 1994.
Klugbauer et al., "Structure and functional expression of a new member of the tetrodotoxin-sensitive voltage-activated sodium channel family from human neuroendocrine cells," *EMBO J. 14*(6): 1084-1090, 1995.
Kobayashi and Furukawa, "Studies on Indole Derivatives. I. Synthesis of 3-Phenyl-9H-pyridazino-[3,4-b]indole Derivatives," *Chemical & Pharmaceutical Bulletin 12*(10): 1129-1135, Oct. 1964.
Kollmar et al., "2-Amino-3-Fluorobenzoic Acid [Benzoic acid, 2-amino-3-fluoro-]," *Organic Syntheses, Coll. 79*: 196, 2002, 5 pages.
Kornet and Thio, "Oxindole-3-spiropyrrolidines and -piperidines. Synthesis and Local Anesthetic Activity," *Journal of Medicinal Chemistry 19*(7): 892-898, 1976.
Kotha et al., "Recent applications of the Suzuki-Miyaura cross-coupling reaction in organic synthesis," *Tetrahedron 58*: 9633-9695, 2002.
Kubo et al., "Michael Additions of Indoles to 2-oxoindolin-3-ylidene Ketones," *Heterocycles 4*(10): 1675-1680, 1976.
Kumar et al., "A New Route to Spiropyrrolidinyl-oxindole Alkaloids via Iodide Ion Induced Rearrangement of [(N-Aziridinomethylthio)methylene]-2-oxindoles," *Organic Letters 3*(26): 4193-4196, 2001.
Kuzma et al., "Progress in the Development of Ultra-Long-Acting Local Anesthetics," *Regional Anesthesia 22*(6): 543-551, Nov.-Dec. 1997.
Lackey and Sternbach, "Synthesis of Substituted Quinoline-4-carboxylic Acids," *Synthesis*: 993-997, Oct. 1993.

Lai et al., "The role of voltage-gated sodium channels in neuropathic pain," *Current Opinion in Neurobiology* 13:291-297, 2003.

Laus, "Kinetics of isomerization of tetracyclic spiro oxindole alkaloids," *J. Chem. Soc., Perkin Trans. 2*: 315-317, 1998.

Laus et al., "Analysis of the kinetics of isomerization of spiro oxindole alkaloids," *J. Chem. Soc., Perkin Trans. 2*: 1931-1936, 1996.

Lee-Son et al., "Stereoselective Inhibition of Neuronal Sodium Channels by Local Anesthetics," *Anesthesiology* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.

Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.

Lindemann et al., "Zur Kenntnis der Indoxazene," *Justus Liebigs Annalen der Chemie* 456: 284-311, 1927.

Lindwall and Maclennan, "A Condensation of Acetophenone with Isatin by the Knoevenagel Method," *Journal of the American Chemical Society* 54: 4739-4744, Dec. 1932.

Liu et al., "Mutations in Cardiac Sodium Channels: Clinical Implications," *Am. J. Pharmacogenomics* 3(3): 173-179, 2003.

Lossin et al., "Molecular Basis of an Inherited Epilepsy," *Neuron* 34: 877-884, Jun. 13, 2002.

Loudon and Ogg, "2:3-Dihydro-3-oxobenz-1:4-oxazines," *J. Chem. Soc.*: 739-744, 1955.

Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.

Lyalin et al., [title unavailable], *Zhurnal Organicheskoi Khimii* 20(4): 846-849, 1984.

Ma and Cai, "*N,N*-Dimethyl Glycine-Promoted Ullmann Coupling Reaction of Phenols and Aryl Halides," *Organic Letters* 5(21): 3799-3802, 2003.

Maercker and Theysohn, "Versuche zur Umlagerung von 2-Cyclopropyl-äthyl-Anionen," *Liebigs Ann. Chem.* 759: 132-157, 1972.

Maginnity and Gaulin, "Derivatives of *o*-, *m*- and *p*-Aminobenzotrifluoride," *J. Am. Chem. Soc.* 73: 3579-3580, Aug. 1951.

Majumdar et al., "1-Alkylisatins via Aldol-Retro-aldol Condensation," *J. Chem. Research (S)*, 460-461, 1996.

Mann et al., "The Synthesis of Lignans and Related Structures using Quinodimethanes and Isobenzofurans: Approaches to the Podophyllins," *J. Chem. Soc. Perkin Trans. I*: 2081-2088, 1984.

Mannaioni et al., "Tryptophan Metabolism and Hepatic Encephalopathy. Studies on the Sedative Properties of Oxindole," *Advances in experimental medicine and biology* 467: 155-167, 1999.

Mao and Baldwin, "New Spirocyclic Oxindole Synthesis Based on a Hetero Claisen Rearrangement," *Organic Letters* 6(14): 2425-2428, 2004.

Mao and Chen, "Systemic lidocaine for neuropathic pain relief," *Pain* 87: 7-17, 2000.

Marcantonio et al., "An Investigation into Causes and Effects of High Cyanide Levels in the Palladium-Catalyzed Cyanation Reaction," *Organic Letters* 6(21): 3723-3725, 2004.

Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.

Marti and Carreira, "Total Synthesis of (—)-Spirotryprostatin B: Synthesis and Related Studies," *J. Am. Chem. Soc.* 127(32): 11505-11515, 2005.

McMurtrey and Daves, Jr., "König's Adducts of *N*-Alkyl(aryl)aminoethanols and Quinones. 3,4-Dihydro-4-alkyl(aryl)-8a-hydroxy-2*H*-1,4,benzoxazin-6(8a*H*)-ones," *J. Org. Chem.* 35(12): 4252-4253, 1970.

McNeal et al., "[$^3$H]Batrachotoxinin A 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Meisler et al., "Sodium channel gene family: epilepsy mutations, gene interactions and modifier effects," *J. Physiol.* 588.11: 1841-1848, 2010.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Morinville et al., "Distribution of the Voltage-Gated Sodium Channel $Na_v1.7$ in the Rat: Expression in the Autonomic and Endocrine Systems," *Journal of Comparative Neurology* 504: 680-689, 2007.

Morton et al., "Novel solid-phase synthesis of 1,5-benzothiazepine-4-one derivatives," *Tetrahedron Letters* 41: 3029-3033, 2000.

Muci and Buchwald, "Practical Palladium Catalysts for C-N and C-O Bond Formation," *Topics in Current Chemistry* 219: 131-209, 2002.

Muhammad et al., "Two stereoisomeric pentacyclic oxindole alkaloids from *Uncaria tomentosa*; uncarine C and uncarine E," *Acta Cyst. C57*: 480-482, 2001.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nair et al., "Formal dipolar cycloaddition of allylsilanes to *o*-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-*dl*-thyronine and Some of its Iodinated Derivatives," *J. Am. Chem. Soc.* 63: 609-611, Feb. 1941.

Oguri et al., "Amino Acids and Peptides XXVIII. A New Synthesis of α-Amino Acid Derivatives by Alkylation of Schiff Bases derived from Glycine and Alanine," *Chem. Pharm. Bull.* 25(9): 2287-2291, 1977.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pages.

Overman and Watson, "Diaterosection in the Formation of Spirocyclic Oxindoles by the Intramolecular Heck Reaction," *J. Org. Chem* 71: 2587-2599, 2006.

Papale et al., "Heterozygous mutations of the voltage-gated sodium channel SCN8A are associated with spike-wave discharges and absence epilepsy in mice," *Human Molecular Genetics* 18(9): 1633-1641, 2009.

Pereira et al., "Severe epilepsy, retardation, and dysmorphic features with a 2q deletion including SCN1A and SCN2A," *Neurology* 63: 191-192, 2004.

Pietra and Tacconi, "α-Alkyl- and α-aryl-N-methyltryptamines," *Farmaco, Edizione Scientifica* 14: 854-866, 1959, Caplus Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7): 1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines," *Bioorganic & Medicinal Chemistry* 11: 407-419, 2003.

Raymond et al., "Expression of Alternatively Spliced Sodium Channel α-Subunit Genes," *Journal of Biological Chemistry* 279(44): 46234-46241, Oct. 29, 2004.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in SCN9A," *PNAS* 107(11): 5148-5153, Mar. 16, 2010.

Ren and Dubner, "Enhanced Descending Modulation of Nociception in Rats With Persistent Hindpaw Inflamation," *Journal of Neurophysiology* 76(5): 3025-3037, Nov. 1996.

Rhodes et al., "Noninactivating voltage-gated sodium channels in severe myoclonic epilepsy of infancy," *PNAS* 101(30): 11147-11152, Jul. 27, 2004.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with o-Fluoro-acetophenone, o-Fluorobenzaldehyde and o-Fluorobenzophenone," *Aust. J. Chem.* 44: 1097-1114, 1991.

Ross et al., "Loss of Inhibitory Interneurons in the Dorsal Spinal Cord and Elevated Itch in Bhlhb5 Mutant Mice," *Neuron* 65: 886-898, Mar. 25, 2010.

Rossiter, "A convenient synthesis of 3-methyleneoxindoles: cytotoxic metabolites of indole-3-acetic acids," *Tetrahedron Letters* 43: 4671-4673, 2002.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (—)-spirotryprostatin B via a diastereoselective azomethine glide [1,3]-dipolar cycloaddition reaction," *Tetrahedron* 58: 6311-6322, 2002.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono O-MOM- and O-Benzylresorcinols Prenylated at C-2 or C-4 Positions," *Synthesis* 6: 10171021, 1999.

Singh et al., "Novel cAMP PDE III Inhibitors: Imidazo[4,5-b]pyridine-2(3H)-ones and Thiazolo[4,5-b]pyridin-2(3H)-ones and Their Analogs," *J. Med. Chem.* 37: 248-254, 1994.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3' ]oxindole-spiro[3.7"](3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (S)-(—)-Spirobrassinin, and Its Oxazoline Analog," *J. Org. Chem.* 66: 3940-3947, 2001.

Tacconi et al., "Heterodiene Syntheses—V 1,2-versus 1,4-cycloaddition reactions of enamines to n-substituted 3-oxindolideneacetopheones," *Tetrahedron* 27:561-579, 1971.

Takahashi et al., "Palladium(0)-Catalyzed Carbonylation on the Multipin™ System," *Tetrahedron Letters* 40: 7843-7846, 1999.

Tamaoka, "Paramyotonia Congenita and Skeletal Sodium Channelopathy," *Internal Medicine* 42(9): 769-770, Sep. 2003.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2H-pyrrolo[2,3-b]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Twycross et al., "Itch: scratching more than the surface," *Q. J. Med.* 96: 7-26, 2003.

Usman et al., "1-Acetyl-3-(2-chloro-2,3-dihydrobenzofuran-3-yl)-1,2-dihydro-3 -hydroxy-2-oxo-3H-indole," *Acta Cryst. E58*: o37-o39, 2002.

Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-*b*]pyridin-2(2H)-one Derivatives as Potential Non-opioid Analgesic Agents," *Pharmaceutical Sciences 3*: 283-287, 1997.

Viaud et al., "Acylation of Oxazolo[4,5-*b*]pyridin-2(3H)-ones, 2-Phenyloxazolo[4,5 -*b*]pyridines and Pyrrolo[2,3-*b*]pyridin-2(2H)ones," *Tetrahedron* 53(14): 5159-5168, 1997.

Villamil et al., "Efficacy of lidocaine in the treatment of pruritus in patients with chronic cholestatic liver diseases," *The American Journal of Medicine 118*: 1160-1163, 2005.

Vippagunta et al., "Crystalline solids," *Advanced Drug Delivery Reviews 48*: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

Wang and Ganesan, "A Biomimetic Total Synthesis of (—)-Spirotryprostatin B and Related Studies," *J. Org. Chem.* 65(15): 4685-4693, 2000.

Watanabe et al., "$Na_x2$/NaG Channel Is Involved in Control of Salt-Intake Behavior in the CNS," *Journal of Neuroscience* 20(20): 7743-7751, Oct. 15, 2000.

Weidmann et al., "2-[(2-Pyridylmethyl)sulfinyl]-1H-thieno[3,4-*d*]imidazoles. A Novel Class of Gastric $H^+/K^+$-ATPase Inhibitors," *J. Med. Chem.* 35: 438-450, 1992.

Wolff (ed.), *Burger's Medicinal Chemistry and Drug Discovery, Fifth Edition, vol. I: Principles and Practice*, John Wiley & Sons, Inc., New York, New York, 1994, pp. 975-977.

Wood et al., "Voltage-Gated Sodium Channels and Pain Pathways," *J. Neurobiol.* 61: 55- 71, 2004.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Wu et al., "The Effect of Hypercholesterolemia on the Sodium Inward Currents in Cardiac Myocyte," *J. Mol. Cell. Cardiol.* 27: 1263-1269, 1995.

Yang and Williams, "Palladium-Catalyzed Cyanation of Aryl Bromides Promoted by Low-Level Organotin Compounds," *Organic Letters* 6(17): 2837-2840, 2004.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of syn-1-acetyl-9'aH-8'-methoxyspiro[indole-3,2'-oxeto[3',2':4,5]furo[3,2-g][1]benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans. 1*: 345-353, 2002.

Zinser et al., "Anthelmintic paraherquamides are cholinergic antagonists in gastrointestinal nematodes and mammals," *J. vet. Pharmacol. Therap.* 25: 241-250, 2002.

Invitation to Pay Additional Fees, mailed Aug. 23, 2006, for PCTAN PCT/US2006/014845, 11 pages.

International Search Report and Written Opinion, mailed Oct. 31, 2006, for PCTAN PCT/US2006/014865, 26 pages.

International Preliminary Report on Patentability, mailed Nov. 1, 2007, for PCTAN PCT/US2006/014865, 13 pages.

Chafeev et al., entitled Oxindole Compounds and Their Uses As Therapeutic Agents, Preliminary Amendment dated Jul. 14, 2006, for U.S. Appl. No. 11/408,269, 6 pages.

Chafeev et al., entitled Oxindole Compounds and Their Uses As Therapeutic Agents, Restriction Requirement mailed Sep. 9, 2008, for U.S. Appl. No. 11/408,269, 10 pages.

Chafeev et al., entitled Oxindole Compounds and Their Uses As Therapeutic Agents, Response to Restriction Requirement dated Oct. 9, 2008, for U.S. Appl. No. 11/408,269, 3 pages.

Chafeev et al., entitled Oxindole Compounds and Their Uses As Therapeutic Agents, Office Action mailed Dec. 15, 2008, for U.S. Appl. No. 11/408,269, 29 pages.

International Search Report and Written Opinion, mailed Oct. 6, 2006, for PCTAN PCT/US2006/014352, 11 pages.

International Preliminary Report on Patentability, mailed Oct. 16, 2007, for PCTAN PCT/US2006/014352, 6 pages.

Chafeev et al., entitled Spiro-Oxindole Compounds and Their Uses As Therapeutic Agents, Preliminary Amendment dated Jul. 5, 2006, for U.S. Appl. No. 11/402,310, 6 pages.

Chafeev et al., entitled Spiro-Oxindole Compounds and Their Uses As Therapeutic Agents, Restriction Requirement mailed Feb. 10, 2009, for U.S. Appl. No. 11/402,310, 7 pages.

Chafeev et al., entitled Spiro-Oxindole Compounds and Their Uses As Therapeutic Agents, Response to Restriction Requirement dated Feb. 25, 2009, for U.S. Appl. No. 11/402,310, 109 pages.

Chafeev et al., entitled Spiro-Oxindole Compounds and Their Uses As Therapeutic Agents, Office Action mailed May 15, 2009, for U.S. Appl. No. 11/402,310, 43 pages.

Chafeev et al., entitled Spiro-Oxindole Compounds and Their Uses As Therapeutic Agents, Amendment dated Aug. 17, 2009, for U.S. Appl. No. 11/402,310, 150 pages.

Chafeev et al., entitled Spiro-Oxindole Compounds and Their Uses As Therapeutic Agents, Notice of Allowance mailed Sep. 30, 2009, for U.S. Appl. No. 11/402,310, 9 pages.

Chafeev et al., entitled Spiro-Oxindole Compounds and Their Uses As Therapeutic Agents, Statement of the Substance of the Interview, mailed Oct. 30, 2009 for U.S. Appl. No. 11/402,310, 2 pages.

Chafeev et al., entitled Spiro-Oxindole Compounds and Their Uses As Therapeutic Agents, Communication dated Nov. 17, 2009, for U.S. Appl. No. 11/402,310, 4 pages.

Sun et al., entitled Spiro-Oxindole Compounds and Their Uses As Therapeutic Agents, Office Action dated Jul. 12, 2010, for U.S. Appl. No. 12/650,218, 26 pages.

Sun et al., entitled Spiro-Oxindole Compounds and Their Uses As Therapeutic Agents, Amendment dated Nov. 10, 2010, for U.S. Appl. No. 12/650,218, 28 pages.

Invitation to Pay Additional Fees, mailed Jan. 2, 2007, for PCTAN PCT/US2006/014887, 9 pages.

International Search Report and Written Opinion, mailed Mar. 15, 2007, for PCTAN PCT/US2006/014887, 22 pages.

International Preliminary Report on Patentability, mailed Nov. 1, 2007, for PCTAN PCT/US2006/014887, 12 pages.

Chafeev et al., entitled Heterocyclic Compounds and Their Uses As Therapeutic Agents, Preliminary Amendment dated Jul. 14, 2006, for U.S. Appl. No. 11/407,859, 6 pages.

Chafeev et al., entitled Heterocyclic Compounds and Their Uses As Therapeutic Agents, Restriction Requirement mailed Mar. 31, 2008, for U.S. Appl. No. 11/407,859, 9 pages.

Chafeev et al., entitled Heterocyclic Compounds and Their Uses As Therapeutic Agents, Response to Restriction Requirement dated Apr. 30, 2008, for U.S. Appl. No. 11/407,859, 39 pages.

Chafeev et al., entitled Heterocyclic Compounds and Their Uses As Therapeutic Agents, Office Action mailed Jun. 20, 2008, for U.S. Appl. No. 11/407,859, 46 pages.

Chafeev et al., entitled Heterocyclic Compounds and Their Uses As Therapeutic Agents, Amendment dated Oct. 17, 2008, for U.S. Appl. No. 11/407,859, 41 pages.

Chafeev et al., entitled Heterocyclic Compounds and Their Uses As Therapeutic Agents, Office Action mailed Jan. 15, 2009, for U.S. Appl. No. 11/407,859, 8 pages.

International Search Report and Written Opinion, mailed Aug. 11, 2006, for PCTAN PCT/US2006/013318, 15 pages.

International Preliminary Report on Patentability, mailed Oct. 16, 2007, for PCTAN PCT/US2006/013318, 9 pages.

Chafeev et al., entitled Spiroheterocyclic Compounds and Their Uses As Therapeutic Agents, Preliminary Amendment dated Jul. 7, 2006, for U.S. Appl. No. 11/402,200, 6 pages.

Chafeev et al., entitled Spiroheterocyclic Compounds and Their Uses As Therapeutic Agents, Restriction Requirement mailed Feb. 10, 2009, for U.S. Appl. 11/402,200, 6 pages.
Chafeev et al., entitled Spiroheterocyclic Compounds and Their Uses As Aaf Therapeutic Agents, Response to Restriction Requirement dated Feb. 27, 20009, for U.S. Appl. No. 11/402,200, 31 pages.
Chafeev et al., entitled Spiroheterocyclic Compounds and Their Uses As Therapeutic Agents, Office Action mailed Apr. 24, 2009 for U.S. Appl. No. 11/402,200, 30 pages.
Chafeev et al., entitled Spiroheterocyclic Compounds and Their Uses As Therapeutic Agents, Amendment dated Aug. 24, 2009, for U.S. Appl. No. 11/402,200, 36 pages.
Chafeev et al., entitled Spiroheterocyclic Compounds and Their Uses As Therapeutic Agents, Office Action mailed Nov. 17, 2009, for U.S. Appl. No. 11/402,200, 7 pages.
Chafeev et al., entitled Spiroheterocyclic Compounds and Their Uses As Therapeutic Agents, Amendment dated Mar. 17, 2010, for U.S. Appl. No. 11/402,200, 17 pages.
Chafeev et al., entitled Spiroheterocyclic Compounds and Their Uses As. Therapeutic Agents, Notice of Allowance dated May 13, 2010, for U.S. Appl. No. 11/402,200, 16 pages.
Chafeev et al., entitled Spiroheterocyclic Compounds and Their Uses As Therapeutic Agents, Preliminary Amendment dated Oct. 25, 2010, for U.S. Appl. No. 12/855,514, 32 pages.
International Search Report and Written Opinion, mailed Mar. 3, 2008, for PCTAN PCT/US2007/081240,16 pages.
International Preliminary Report on Patentability mailed Apr. 23, 2009, for PCTAN PCT/US2007/081240, 9 pages.
International Search Report and Written Opinion, mailed Oct. 13, 2008, for PCTAN PCT/US2007/081323, 21 pages.
International Preliminary Report on Patentability, mailed Apr. 15, 2009, for PCTAN PCT/US2007/081323, 12 pages.
International Search Report and Written Opinion, mailed Mar. 3, 2008, for PCTAN PCT/US2007/081244, 21 pages.
International Preliminary Report on Patentability, mailed Apr. 23, 2009, for PCTAN PCT/US2007/081244, 12 pages.
Invitation to Pay Additional Fees, mailed Jul. 16, 2008, for PCTAN PCT/US2007/081319, 10 pages
International Search Report and Written Opinion, mailed Dec. 29, 2008, for PCTAN PCT/US2007/081319,18 pages.
International Preliminary Report on Patentability, mailed Apr. 15, 2009, for PCTAN PCT/US2007/081319, 8 pages.
International Search Report and Written Opinion, mailed May 19, 2008, for PCTAN PCT/US2007/081247, 18 pages.
International Preliminary Report on Patentability, mailed Apr. 15, 2009, for PCTAN PCT/US2007/081247, 10 pages.
Chafeev et al., entitled Use of Spiro-Oxindole Compounds As Therapeutic Agents, Preliminary Amendment dated Mar. 4, 2010, for U.S. Appl. No. 12/445,264, 18 pages.
International Search Report and Written Opinion, mailed May 13, 2008, for PCTAN PCT/US2007/081318, 12 pages.
International Preliminary Report on Patentability, mailed Apr. 15, 2009, for PCTAN PCT/US2007/081318, 5 pages.
International Search Report and Written Opinion, mailed Mar. 6, 2008, for PCTAN PCT/US2007/081297, 18 pages.
International Preliminary Report on Patentability, mailed Apr. 15, 2009, for PCTAN PCT/US2007/081297, 10 pages.
Invitation to Pay Additional Fees, mailed Jan. 27, 2009, for PCTAN PCT/US2007/081320, 7 pages.
Written Opinion of the International Searching Authority, mailed Jan. 5, 2009, for PCTAN PCT/US2007/081320, 11 pages.
International Preliminary Report on Patentability, mailed May 5, 2009, for PCTAN PCT/US2007/081320, 12 pages.
International Search Report and Written Opinion, mailed Feb. 9, 2010 for PCTAN PCT/US2009/063290, 13 pages.
International Search Report and Written Opinion, mailed Oct. 1, 2010, for PCTAN PCT/US2010/040187, 13 pages.
Invitation to Pay Additional Fees, mailed Feb. 9, 2010, for PCTAN PCT/US2009/060537, 8 pages.
International Search Report and Written Opinion, mailed Oct. 6, 2010, for PCTAN PCT/US2009/060537, 18 pages.

Chafeev et al., entitled Spiro-Oxindole Compounds and Their Use As Therapeutic Agents, Preliminary Amendment dated Jan. 12, 2010, for U.S. Appl. No. 12/578,148, 57 pages.
International Search Report and Written Opinion, mailed Jan. 22, 2010, for PCTAN PCT/US2009/060455, 14 pages.
International Search Report and Written Opinion, mailed Apr. 8, 2010, for PCTAN PCT/US2009/069663, 13 pages.
Invitation to Pay Additional Fees, mailed Aug. 18, 2010, for PCTAN PCT/US2010/034223, 7 pages.
Goldberg, "Significance of Molecular Type, Shape and Complementarity in Clathrate Inclusion," *Topics in Current Chemistry 149*: 1-44, 1988.
Guillaumet et al., "Synthese d'un analogue dioxinique du psoralene," *Tetrahedron Letters 29*(22): 2665-2666, 1988.
MacNicol., "Clathrates and Molecular Inclusion Phenomena," *Chemical Society Reviews 7*(1): 65-87, 1978.
Pouton, "Lipid formulations for oral administration of drugs: non-emulsifying, self-smulsifying and 'self-microemulsifying' drug delivery systems," *European Journal of Pharmaceutical Sciences 11*(Suppl 2): S93-S98, 2000.
Saenger, "Cyclodextrin Inclusion Compounds in Research and Industry," *Angew. Chem. Int. Ed. Engl 19*: 344-362, 1980.
Sircar et al., "Synthesis and SAR of N-Benzoyl-l-Biphenylalanine Derivatives: Discovery of TR-14035, A Dual $\alpha_4\beta/\alpha_4\beta_1$ Integrin Antagonist," *Bioorganic & Medicinal Chemistry Letters 10*: 2051-2066, 2002.
Weber and Czugler, "Functional Group Assisted Clathrate Formation—Scissor-Like and Roof-Shaped Host Molecules," *Topics in Current Chemistry 149*:45-135, 1988.
Official Action from Intellectual Property India, mailed Apr. 29, 2011, for India Patent Application No. 4597/CHENP/2007, 2 pages.
Chafeev et al., entitled Spiro-Oxindole Compounds and Their Uses as Therapeutic Agents, Office Action dated Feb. 4, 2011, for U.S. Appl. No. 12/650,196, 31 pages.
Chafeev et al., entitled Spiro-Oxindole Compounds and Their Uses as Therapeutic Agents, Amenedment and Winther Declaration dated May 4, 2011, for U.S. Appl. No. 12/650,196, 197 pages.
Chafeev et al., entitled Spiro-Oxindole Compounds and Their Uses as Therapeutic Agents, Office Action mailed Jun. 14, 2011, for U.S. Appl. No. 12/650,196, 17 pages.
Sun et al., entitled Spiro-Oxindole Compounds and Their Uses as Therapeutic Agents, Notice of Allowance mailed Dec. 13, 2010, for U.S. Appl. No. 12/650,218, 19 pages.
Sun et al., entitled Spiro-Oxindole Compounds and Their Uses as Therapeutic Agents, Supplemental Amendment dated Mar. 2, 2011, for U.S. Appl. No. 12/650,218, 3 pages.
Sun et al., entitled Spiro-Oxindole Compounds and Their Uses as Therapeutic Agents, Preliminary Amendment dated Jun. 24, 2011, for U.S. Appl. No. 13/078,678, 32 pages.
International Search Report and Written Opinion, mailed Apr. 1, 2011, for PCTAN PCT/US2010/052704, 12 pages.
Winters et al., entitled Pharmaceutical Compositions for Oral Administration, Preliminary dated Dec. 27, 2010, for U.S. Appl. No. 12/905,048, 9 pages.
International Preliminary Report on Patentability, mailed May 10, 2011, for PCTAN PCT/US2009/, 7 pages.
Chafeev et al., entitled Enantiomers Spiro-Oxindole Compounds and Their Uses as Therapeutic Agents, Restriction Requirement mailed Jun. 20, 2011, for U.S. Appl. No. 12/825,168, 8 pages.
International Preliminary Report on Patentability, mailed Apr. 19, 2011, for PCTAN PCT/US2009/060537, 11 pages.
International Preliminary Report on Patentability, mailed Apr. 19, 2011, for PCTAN PCT/US2009/060455, 7 pages.
Chafeev et al., entitled Spiro-Oxindole Compounds and Their Use as Therapeutic Agents, Office Action dated Apr. 1, 2011, for U.S. Appl. No. 12/577,799, 49 pages.
Official Action from Intellectual Property India, mailed Mar. 28, 2011, for India Patent Application No. 4596/CHENP/2007, 4 pages.
Official Action from Intellectual Property Australia, dated Jan. 12, 2011, for Patent Application No. 2006235593, 5 pages.
Official Action from State Intellectual Property Office of China, dated Dec. 25, 2009, for Patent Application No. 200680011733.9, 4 pages.

Official Action from State Intellectual Property Office of China, dated Oct. 9, 2010, for Patent Application No. 200680011733.9, 4 pages.
Official Action from European Patent Office, dated Apr. 9, 2010, for Patent Application No. 06 750 402.7, 4 pages.
Response to Official Action from European Patent Office, dated Aug. 19, 2010, for Patent Application No. 06 750 402.7,4 105 pages.
Official Action from Intellectual Property Office of New Zealand, dated Sep. 1, 2009, for Patent Application No. 561210, 2 pages.
Response to Official Action from Intellectual Property Office of New Zealand, dated Nov. 22, 2010, for Patent Application No. 561210, 2 pages.
Official Action from Intellectual Property Office of New Zealand, dated Nov. 30, 2010, for Patent Application No. 561210, 1 page.
Response to Official Action from Intellectual Property Office of New Zealand, dated Feb. 21, 2011, for Patent Application No. 561210, 2 pages.
Official Action from Intellectual Property Office of New Zealand, dated Feb. 25, 2011, for Patent Application No. 561210, 2 pages.
Official Action from Intellectual Property Office of Republic of the Philippines, dated Sep. 22, 2010, for Patent Application No. 1-2007-502050, 2 pages.
Response to Official Action from Intellectual Property Office of Republic of the Philippines, dated Jan. 20, 2011, for Patent Application No. 1-2007-502050, 85 pages.
Translation of Official Action from Intellectual Property Office of Russia, dated Sep. 22, 2010, for Patent Application No. 2007141632/04(045572), 7 pages.
Official Action from European Patent Office, dated Aug. 5, 2008, for Patent Application No. 06 758 436.7, 5 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from Intellectual Property of India, dated May 18, 2009, for Patent Application No. 4598/CHENP/2007/,2 pages.
Response to Official Action from Intellectual Property of India, dated Mar. 15, 2010, for Patent Application No. 4598/CHENP/2007, 27 pages.
Official Action from Intellectual Property Office of New Zealand, dated Aug. 27, 2009, for Patent Application No. 561204, 2 pages.
Response to Official Action from Intellectual Property Office of New Zealand, dated Nov. 22, 2010, for Patent Application No. 561204, 2 pages.
Official Action from Intellectual Property Office of New Zealandm dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Official Action from State Intellectual Property Office of China, dated May 5, 2011, for Patent Appliction No. 200780038272.9, 9 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 2011, for Patent Application No. 07 868 434.7, 3 pages.

* cited by examiner ic agents.

SPIRO-OXINDOLE COMPOUNDS AND THEIR USE AS THERAPEUTIC AGENTS

CROSS-REFERENCE TO RELATED APPLICATION

This application claims the benefit under 37 U.S.C. §119(e) of U.S. Provisional Patent Application No. 61/106,410, filed Oct. 17, 2008, which application is incorporated herein by reference in its entirety.

FIELD OF THE INVENTION

The present invention is directed to spiro-oxindole compounds and pharmaceutical compositions comprising the compounds and methods of using the compounds and the pharmaceutical compositions in treating sodium channel-mediated diseases or conditions, such as pain, as well as other diseases and conditions associated with the mediation of sodium channels.

BACKGROUND OF THE INVENTION

Voltage-gated sodium channels, transmembrane proteins that initiate action potentials in nerve, muscle and other electrically excitable cells, are a necessary component of normal sensation, emotions, thoughts and movements (Catterall, W. A., *Nature* (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., *Neuron* (2000), Vol. 28, pp. 365-368). Each alpha-subunit contains four homologous domains, I to IV, each with six predicted transmembrane segments. The alpha-subunit of the sodium channel, forming the ion-conducting pore and containing the voltage sensors regulating sodium ion conduction has a relative molecular mass of 260,000. Electrophysiological recording, biochemical purification, and molecular cloning have identified ten different sodium channel alpha subunits and four beta subunits (Yu, F. H., et al., *Sci. STKE* (2004), 253; and Yu, F. H., et al., *Neurosci.* (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., *Nature* (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. Implicit with function, this family of proteins are considered prime points of therapeutic intervention. $Na_V1.1$ and $Na_V1.2$ are highly expressed in the brain (Raymond, C. K., et al., *J. Biol. Chem.* (2004), 279(44): 46234-41) and are vital to normal brain function. In humans, mutations in $Na_V1.1$ and $Na_V1.2$ result in severe epileptic states and in some cases mental decline (Rhodes, T. H., et al., *Proc. Natl. Acad. Sci. USA* (2004),101(30):11147-52; Kamiya, K., et al., *J. Biol. Chem.* (2004), 24(11):2690-8; Pereira, S., et al., *Neurology* (2004), 63(1):191-2). As such both channels have been considered as validated targets for the treatment of epilepsy (see PCT Published Patent Publication No. WO 01/38564).

$Na_V1.3$ is broadly expressed throughout the body (Raymond, C. K., et al., *op. cit.*). It has been demonstrated to have its expression upregulated in the dorsal horn sensory neurons of rats after nervous system injury (Hains, B. D., et al., *J. Neurosci.* (2003), 23(26):8881-92). Many experts in the field have considered $Na_V1.3$ as a suitable target for pain therapeutics (Lai, J., et al., *Curr. Opin. Neurobiol.* (2003), (3):291-72003; Wood, J. N., et al., *J. Neurobiol.* (2004), 61(1):55-71; Chung, J. M., et al., *Novartis Found Symp.* (2004), 261:19-27; discussion 27-31, 47-54).

$Na_V1.4$ expression is essentially limited to muscle (Raymond, C. K., et al., *op. cit.*). Mutations in this gene have been shown to have profound effects on muscle function including paralysis, (Tamaoka A., *Intern. Med.* (2003), (9):769-70). Thus, this channel can be considered a target for the treatment of abnormal muscle contractility, spasm or paralysis.

The cardiac sodium channel, $Na_V1.5$, is expressed mainly in the heart ventricles and atria (Raymond, C. K., et al., *op. cit.*), and can be found in the sinovial node, ventricular node and possibly Purkinje cells. The rapid upstroke of the cardiac action potential and the rapid impulse conduction through cardiac tissue is due to the opening of $Na_V1.5$. As such, $Na_V1.5$ is central to the genesis of cardiac arrhythmias. Mutations in human $Na_V1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H. et al., *Am. J. Pharmacogenomics* (2003), 3(3):173-9). Sodium channel blocker therapy has been used extensively in treating cardiac arrhythmias. The first antiarrhythmic drug, quinidine, discovered in 1914, is classified as a sodium channel blocker.

$Na_V1.6$ encodes an abundant, widely distributed voltage-gated sodium channel found throughout the central and peripheral nervous systems, clustered in the nodes of Ranvier of neural axons (Caldwell, J. H., et al., *Proc. Natl. Acad. Sci. USA* (2000), 97(10): 5616-20). Although no mutations in humans have been detected, $Na_V1.6$ is thought to play a role in the manifestation of the symptoms associated with multiple sclerosis and has been considered as a target for the treatment of this disease (Craner, M. J., et al., *Proc. Natl. Acad. Sci. USA* (2004), 101(21):8168-73).

$Na_V1.7$ was first cloned from the pheochromocytoma PC12 cell line (Toledo-Aral, J. J., et al., *Proc. Natl. Acad. Sci. USA* (1997), 94:1527-1532). Its presence at high levels in the growth cones of small-diameter neurons suggested that it could play a role in the transmission of nociceptive information. Although this has been challenged by experts in the field as $Na_V1.7$ is also expressed in neuroendocrine cells associated with the autonomic system (Klugbauer, N., et al., *EMBO J.* (1995), 14(6):1084-90) and as such has been implicated in autonomic processes. The implicit role in autonomic functions was demonstrated with the generation of $Na_V1.7$ null mutants; deleting $Na_V1.7$ in all sensory and sympathetic neurons resulted in a lethal perinatal phenotype. (Nassar, et al., *Proc. Natl. Acad. Sci. USA* (2004), 101(34):12706-11). In contrast, by deleting the $Na_V1.7$ expression in a subset of sensory neurons that are predominantly nociceptive, a role in pain mechanisms, was demonstrated (Nassar, et al., *op. cit.*).

Further support for $Na_V1.7$ blockers active in a subset of neurons is supported by the finding that two human heritable pain conditions, primary erythermalgia and familial rectal pain, have been shown to map to $Na_V1.7$ (Yang, Y., et al., *J. Med. Genet.* (2004), 41(3):171-4).

The expression of $Na_V1.8$ is essentially restricted to the DRG (Raymond, C. K., et al., *op. cit.*). There are no identified human mutations for $Na_V1.8$. However, $Na_V1.8$-null mutant mice were viable, fertile and normal in appearance. A pronounced analgesia to noxious mechanical stimuli, small deficits in noxious thermoreception and delayed development of inflammatory hyperalgesia suggested to the researchers that $Na_V1.8$ plays a major role in pain signalling (Akopian, A. N., et al., *Nat. Neurosci.* (1999), 2(6): 541-8). Blocking of this channel is widely accepted as a potential treatment for pain (Lai, J, et al., *op. cit.*; Wood, J. N., et al., *op. cit.*; Chung, J. M., et al., *op. cit.*). PCT Published Patent Application No. WO03/037274A2 describes pyrazole-amides and sulfonamides for the treatment of central or peripheral nervous system conditions, particularly pain and chronic pain by blocking sodium channels associated with the onset or recurrence of the indicated conditions. PCT Published Patent Application No. WO03/037890A2 describes piperidines for the treatment of central or peripheral nervous system conditions, particularly pain and chronic pain by blocking sodium channels associated with the onset or recurrence of the indicated conditions. The compounds, compositions and methods of these inventions are of particular use for treating neuropathic or inflammatory pain by the inhibition of ion flux through a channel that includes a PN3 ($Na_V1.8$) subunit.

The tetrodotoxin insensitive, peripheral sodium channel $Na_V1.9$, disclosed by Dib-Hajj, S. D., et al. (see Dib-Hajj, S. D., et al., *Proc. Natl. Acad. Sci. USA* (1998), 95(15):8963-8) was shown to reside solely in the dorsal root ganglia. It has been demonstrated that $Na_V1.9$ underlies neurotrophin (BDNF)-evoked depolarization and excitation, and is the only member of the voltage gated sodium channel superfamily to be shown to be ligand mediated (Blum, R., Kafitz, K. W., Konnerth, A., *Nature* (2002), 419 (6908):687-93). The limited pattern of expression of this channel has made it a candidate target for the treatment of pain (Lai, J, et al., *op. cit.*; Wood, J. N., et al., *op. cit.*; Chung, J. M. et al., *op. cit.*).

NaX is a putative sodium channel, which has not been shown to be voltage gated. In addition to expression in the lung, heart, dorsal root ganglia, and Schwann cells of the peripheral nervous system, NaX is found in neurons and ependymal cells in restricted areas of the CNS, particularly in the circumventricular organs, which are involved in body-fluid homeostasis (Watanabe, E., et al., *J. Neurosci.* (2000), 20(20):7743-51). NaX-null mice showed abnormal intakes of hypertonic saline under both water- and salt-depleted conditions. These findings suggest that the NaX plays an important role in the central sensing of body-fluid sodium level and regulation of salt intake behaviour. Its pattern of expression and function suggest it as a target for the treatment of cystic fibrosis and other related salt regulating maladies.

Studies with the sodium channel blocker tetrodotoxin (TTX) used to lower neuron activity in certain regions of the brain, indicate its potential use in the treatment of addiction. Drug-paired stimuli elicit drug craving and relapse in addicts and drug-seeking behavior in rats. The functional integrity of the basolateral amygdala (BLA) is necessary for reinstatement of cocaine-seeking behaviour elicited by cocaine-conditioned stimuli, but not by cocaine itself. BLA plays a similar role in reinstatement of heroin-seeking behavior. TTX-induced inactivation of the BLA on conditioned and heroin-primed reinstatement of extinguished heroin-seeking behaviour in a rat model (Fuchs, R. A. and See, R. E., *Psychopharmacology* (2002) 160(4):425-33).

This closely related family of proteins has long been recognised as targets for therapeutic intervention. Sodium channels are targeted by a diverse array of pharmacological agents. These include neurotoxins, antiarrhythmics, anticonvulsants and local anesthetics (Clare, J. J., et al., *Drug Discovery Today* (2000) 5:506-520). All of the current pharmacological agents that act on sodium channels have receptor sites on the alpha subunits. At least six distinct receptor sites for neurotoxins and one receptor site for local anesthetics and related drugs have been identified (Cestèle, S. et al., *Biochimie* (2000), Vol. 82, pp. 883-892).

The small molecule sodium channel blockers or the local anesthetics and related antiepileptic and antiarrhythmic drugs, interact with overlapping receptor sites located in the inner cavity of the pore of the sodium channel (Catterall, W. A., *Neuron* (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrignine, phenyloin and carbamazepine) and certain cardiac arrhythmias (e.g. lignocaine, tocamide and mexiletine). However, the potency and therapeutic index of these blockers is not optimal and have limited the usefulness of these compounds in a variety of therapeutic areas where a sodium channel blocker would be ideally suited.

Management of Acute and Chronic Pain

Drug therapy is the mainstay of management for acute and chronic pain in all age groups, including neonates, infants and children. The pain drugs are classified by the American Pain Society into three main categories: 1) non-opioid analgesics-acetaminophen, and non-steroidal anti-inflammatory drugs (NSAIDs), including salicylates (e.g. aspirin), 2) opioid analgesics and 3) co-analgesics.

Non-opioid analgesics such as acetaminophen and NSAIDs are useful for acute and chronic pain due to a variety of causes including surgery, trauma, arthritis and cancer. NSAIDs are indicated for pain involving inflammation because acetaminophen lacks anti-inflammatory activity. Opioids also lack anti-inflammatory activity. All NSAIDs inhibit the enzyme cyclooxygenase (COX), thereby inhibiting prostaglandin synthesis and reducing the inflammatory pain response. There are at least two COX isoforms, COX-1 and COX-2. Common non-selective COX inhibitors include, ibuprofen and naproxen. Inhibition of COX-1, which is found in platelets, GI tract, kidneys and most other human tissues, is thought to be associated with adverse effects such as gastrointestinal bleeding. The development of selective COX-2 NSAIDs, such as Celecoxib, Valdecoxib and Rofecoxib, have the benefits of non-selective NSAIDs with reduced adverse effect profiles in the gut and kidney. However, evidence now suggests that chronic use of certain selective COX-2 inhibitors can result in an increased risk of stroke occurrence.

The use of opioid analgesics is recommended by the American Pain Society to be initiated based on a pain-directed history and physical that includes repeated pain assessment. Due to the broad adverse effect profiles associated with opiate use, therapy should include a diagnosis, integrated interdisciplinary treatment plan and appropriate ongoing patient monitoring. It is further recommended that opioids be added to non-opioids to manage acute pain and cancer related pain that does not respond to non-opioids alone. Opioid analgesics act as agonists to specific receptors of the mu and kappa types in the central and peripheral nervous system. Depending on the opioid and its formulation or mode of administration it can be of shorter or longer duration. All opioid analgesics have a risk of causing respiratory depression, liver failure, addiction and dependency, and as such are not ideal for long-term or chronic pain management.

A number of other classes of drugs may enhance the effects of opioids or NSAIDSs, have independent analgesic activity in certain situations, or counteract the side effects of analgesics. Regardless of which of these actions the drug has, they are collectively termed "coanalgesics". Tricyclic antidepressants, antiepileptic drugs, local anaesthetics, glucocorticoids, skeletal muscle relaxants, anti-spasmodil agents, antihistamines, benzodiazepines, caffeine, topical agents (e.g. capsaicin), dextroamphetamine and phenothizines are all used in the clinic as adjuvant therapies or individually in the treatment of pain. The antiepeileptic drugs in particular have enjoyed some success in treating pain conditions. For instance, Gabapentin, which has an unconfirmed therapeutic target, is indicated for neuropathic pain. Other clinical trials are attempting to establish that central neuropathic pain may respond to ion channel blockers such as blockers of calcium, sodium and/or NMDA (N-methyl-D-aspartate) channels. Currently in development are low affinity NMDA channel blocking agents for the treatment of neuropathic pain. The literature provides substantial pre-clinical electrophysiological evidence in support of the use of NMDA antagonists in the treatment of neuropathic pain. Such agents also may find use in the control of pain after tolerance to opioid analgesia occurs, particularly in cancer patients.

Systemic analgesics such as NSAIDs and opioids are to be distinguished from therapeutic agents which are useful only as local analgesics/anaesthetics. Well known local analgesics such as lidocaine and xylocalne are non-selective ion channel blockers which can be fatal when administered systemically. A good description of non-selective sodium channel blockers is found in Madge, D. et al., *J. Med. Chem.* (2001), 44(2): 115-37.

Several sodium channel modulators are known for use as anticonvulsants or antidepressants, such as carbamazepine, amitriptyline, lamotrigine and riluzole, all of which target brain tetradotoxin-sensitive (TTX-S) sodium channels. Such TTX-S agents suffer from dose-limiting side effects, including dizziness, ataxia and somnolence, primarily due to action at TTX-S channels in the brain.

Sodium Channels Role in Pain

Sodium channels play a diverse set of roles in maintaining normal and pathological states, including the long recognized role that voltage gated sodium channels play in the generation of abnormal neuronal activity and neuropathic or pathological pain (Chung, J. M. et al., *op. cit.*). Damage to peripheral nerves following trauma or disease can result in changes to sodium channel activity and the development of abnormal afferent activity including ectopic discharges from axotomised afferents and spontaneous activity of sensitized intact nociceptors. These changes can produce long-lasting abnormal hypersensitivity to normally innocuous stimuli, or allodynia. Examples of neuropathic pain include, but are not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There has been some degree of success in treating neuropathic pain symptoms by using medications, such as gabapentin, and more recently pregabalin, as short-term, first-line treatments. However, pharmacotherapy for neuropathic pain has generally had limited success with little response to commonly used pain reducing drugs, such as NSAIDS and opiates. Consequently, there is still a considerable need to explore novel treatment modalities.

There remains a limited number of potent effective sodium channel blockers with a minimum of adverse events in the clinic. There is also an unmet medical need to treat neuropathic pain and other sodium channel associated pathological states effectively and without adverse side effects. The present invention provides methods to meet these critical needs.

SUMMARY OF THE INVENTION

The present invention is directed to spiro-oxindole compounds and pharmaceutical compositions comprising the compounds and methods of using the compounds and the pharmaceutical compositions of the invention for the treatment and/or prevention of sodium channel-mediated diseases or conditions, such as pain. The present invention is also directed to methods of using the compounds of the invention and pharmaceutical compositions comprising the compounds of the invention for the treatment of other sodium channel-mediated diseases or conditions, including, but not limited to central nervous conditions such as epilepsy, anxiety, depression and bipolar disease; cardiovascular conditions such as arrhythmias, atrial fibrillation and ventricular fibrillation; neuromuscular conditions such as restless leg syndrome, essential tremor and muscle paralysis or tetanus; neuroprotection against stroke, glaucoma, neural trauma and multiple sclerosis; and channelopathies such as erythromyalgia and familial rectal pain syndrome. The present invention is also directed to the use of the compounds of the invention and pharmaceutical compositions comprising the compounds of the invention for the treatment and/or prevention of diseases or conditions, such as hypercholesterolemia, benign prostatic hyperplasia, pruritis, and cancer.

Accordingly, in one aspect, this invention is directed to compounds of formula (I):

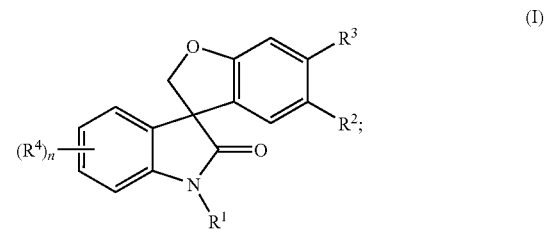

wherein:

n is 0, 1, 2, 3 or 4;

$R^1$ is hydrogen, —$R^5$—C(=NO$R^6$)N($R^7$)$R^8$, diphenylmethyl, aralkyl (optionally substituted with a substituent selected from the group consisting of —N($R^7$)$R^8$, —C(=NO$R^6$)N($R^7$)$R^8$, —O—$R^5$—O$R^7$, —O—$R^5$—C(O)O$R^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);

R² is hydrogen;
R³ is selected from the group consisting of —O—R⁵—N(R⁷)R⁸, —O—R⁵—N(R⁷)C(O)OR⁸, —O—R⁵—C(O)OR⁷, —O—Si(R⁷)₃ and —N[S(O)₂R⁷]₂;
or R² and R³, together with the carbons to which they are attached, form a fused O-heterocyclyl ring optionally substituted by =NOR⁷;
R⁴ is selected from the group consisting of alkyl, halo, haloalkyl, optionally substituted aryl and optionally substituted aralkyl;
each R⁵ is independently selected from the group consisting of an optionally substituted straight or branched alkylene chain, an optionally substituted straight or branched alkenylene chain and an optionally substituted straight or branched alkynylene chain;
R⁶ is selected from the group consisting of hydrogen and —C(O)R⁷; and
each R⁷ and R⁸ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;
as a stereoisomer, enantiomer or tautomer thereof or mixtures thereof;
or a pharmaceutically acceptable salt, solvate or prodrug thereof.

In another aspect, the invention provides pharmaceutical compositions comprising a pharmaceutically acceptable excipient and a compound of formula (I), as described above, as a stereoisomer, enantiomer or tautomer thereof or mixtures thereof; or a pharmaceutically acceptable salt, solvate or prodrug thereof.

In another aspect, the invention provides methods for the treatment of pain in a mammal, preferably a human, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of one or more of $Na_V1.1$, $Na_V1.2$, $Na_V1.3$, $Na_V1.4$, $Na_V1.5$, $Na_V1.6$, $Na_V1.7$, $Na_V1.8$, or $Na_V1.9$ is implicated in the disease, condition or disorder, wherein the method comprises administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating a range of sodium channel-mediated diseases or conditions in a mammal, for example, pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythermalgia, primary erythermalgia, familial rectal pain, cancer, epilepsy, partial and general tonic seizures, restless leg syndrome, arrhythmias, fibromyalgia, neuroprotection under ischaemic conditions caused by stroke, glaucoma or neural trauma, tachy-arrhythmias, atrial fibrillation and ventricular fibrillation, wherein the methods comprise administering to the mammal in need thereof, preferably a human, a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating a range of sodium channel-mediated diseases or conditions in a mammal, preferably a human, by the inhibition of ion flux through a voltage-dependent sodium channel in the mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or preventing hypercholesterolemia in a mammal, preferably a human, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or preventing benign prostatic hyperplasia in a mammal, preferably a human, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or preventing pruritis in a mammal, preferably a human, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or preventing cancer in a mammal, preferably a human, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed in the invention.

In another aspect, this invention is directed to the use of the compounds of the invention, as set forth above, as a stereoisomer, enantiomer or tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer or tautomer thereof or mixtures thereof, or a pharmaceutically acceptable salt, solvate or prodrug thereof, in the preparation of a medicament for the treatment of sodium channel-mediated diseases or conditions in a mammal.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Amino" refers to the —$NH_2$ radical.
"Cyano" refers to the —CN radical.
"Hydroxy" refers to the —OH radical.
"Imino" refers to the =NH substituent.
"Nitro" refers to the —$NO_2$ radical.

"Oxo" refers to the =O substituent.
"Thioxo" refers to the =S substituent.
"Trifluoromethyl" refers to the —$CF_3$ radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})$C(O)$OR^{22}$, —$N(R^{20})$C(O)$R^{22}$, —$N(R^{20})$S(O)$_t R^{22}$ (where t is 1 to 2), —S(O)$_t OR^{22}$ (where t is 1 to 2), —S(O)$_p R^{22}$ (where p is 0 to 2), and —S(O)$_t N(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})$C(O)$OR^{22}$, —$N(R^{20})$C(O)$R^{22}$, —$N(R^{20})$S(O)$_t R^{22}$ (where t is 1 to 2), —S(O)$_t OR^{22}$ (where t is 1 to 2), —S(O)$_p R^{22}$ (where p is 0 to 2), and —S(O)$_t N(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably one to eight carbon atoms and which is attached to the rest of the molecule by a single bond, e.g., ethynyl, propynyl, butynyl, pentynyl, hexynyl, and the like. Unless stated otherwise specifically in the specification, an alkynyl group is optionally substituted by one or more of the following groups: alkyl, alkenyl, halo, haloalkenyl, cyano, nitro, aryl, cycloalkyl, heterocyclyl, heteroaryl, oxo, trimethylsilanyl, —$OR^{20}$, —OC(O)—$R^{20}$, —$N(R^{20})_2$, —C(O)$R^{20}$, —C(O)$OR^{20}$, —C(O)$N(R^{20})_2$, —$N(R^{20})$C(O)$OR^{22}$, —$N(R^{20})$C(O)$R^{22}$)—$N(R^{20})$S(O)$_t R^{22}$ (where t is 1 to 2), —S(O)$_t OR^{22}$ (where t is 1 to 2), —S(O)$_p R^{22}$ (where p is 0 to 2), or —S(O)$_t N(R^{20})_2$ (where t is 1 to 2), where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), and —S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), and —S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_t$R$^{22}$ (where t is 1 to 2), —S(O)$_t$OR$^{22}$ (where t is 1 to 2), —S(O)$_p$R$^{22}$ (where p is 0 to 2), and S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_t$R$^{22}$ (where t is 1 to 2), —R$^{21}$—N=C(OR$^{20}$)R$^{20}$, —R$^{21}$—S(O)$_t$OR$^{22}$ (where t is 1 to 2), —R$^{21}$—S(O)$_p$R$^{22}$ (where p is 0 to 2), and —R$^{21}$—S(O)$_t$N(R$^{20}$)$_2$ (where t is 1 to 2) where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene or alkenylene chain; and each R$^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Aralkenyl" refers to a radical of the formula —R$_d$—R$_c$ where R$_d$ is an alkenylene chain as defined above and R$_c$ is one or more aryl radicals as defined above. The aryl part of the aralkenyl radical may be optionally substituted as described above for an aryl group. The alkenylene chain part of the aralkenyl radical may be optionally substituted as defined above for an alkenylene group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—$N(R^{20})_2$, —$R^{21}$—$C(O)R^{20}$, —$R^{21}$—C(O)$OR^{20}$, —$R^{21}$—C(O)N($R^{20}$)$_2$, —$R^{21}$—$N(R^{20})C(O)OR^{22}$, —$R^{21}$—$N(R^{20})C(O)R^{22}$, —$R^{21}$—$N(R^{20})S(O)_tR^{22}$ (where t is 1 to 2), —$R^{21}$—N═$C(OR^{20})R^{20}$, —$R^{21}$—$S(O)_tOR^{22}$ (where t is 1 to 2), —$R^{21}$—$S(O)_pR^{22}$ (where p is 0 to 2), and —$R^{21}$—$S(O)_tN(R^{20})_2$ (where t is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_bR_g$ where $R_b$ is an alkylene chain as defined above and $R_g$ is a cycloalkyl radical as defined above. The alkylene chain and the cycloalkyl radical may be optionally substituted as defined above.

"Cycloalkylalkenyl" refers to a radical of the formula —$R_dR_g$ where $R_d$ is an alkenylene chain as defined above and $R_g$ is a cycloalkyl radical as defined above. The alkenylene chain and the cycloalkyl radical may be optionally substituted as defined above.

"Fused" refers to any ring system described herein which is fused to an existing ring structure in the compounds of the invention. When the fused ring system is a heterocyclyl or a heteroaryl, any carbon in the existing ring structure which becomes part of the fused ring system may be replaced with a nitrogen.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—$N(R^{20})_2$, —$R^{21}$—$C(O)R^{20}$, —$R^{21}$—C(O)$OR^{20}$, —$R^{21}$—C(O)N($R^{20}$)$_2$, —$R^{21}$—$N(R^{20})C(O)OR^{22}$, —$R^{21}$—$N(R^{20})C(O)R^{22}$, —$R^{21}$—$N(R^{20})S(O)_tR^{22}$ (where t is 1 to 2), —$R^{21}$—N═$C(OR^{20})R^{20}$, —$R^{21}$—$S(O)_tOR^{22}$ (where t is 1 to 2), —$R^{21}$—$S(O)_pR^{22}$ (where p is 0 to 2), and —$R^{21}$—$S(O)_tN(R^{20})_2$ (where t is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"O-heterocyclyl" refers to a heterocyclyl radical as defined above containing at least one oxygen. An O-heterocyclyl radical may be optionally substituted as described above for heterocyclyl radicals.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The alkylene chain of the heterocyclylalkyl radical may be optionally substituted as defined above for an alkene chain. The heterocyclyl part of the heterocyclylalkyl radical may be optionally substituted as defined above for a heterocyclyl group.

"Heterocyclylalkenyl" refers to a radical of the formula —$R_dR_h$ where $R_d$ is an alkenylene chain as defined above and $R_h$ is a heterocyclyl radical as defined above, and if the heterocyclyl is a nitrogen-containing heterocyclyl, the heterocyclyl may be attached to the alkenylene chain at the nitrogen atom. The alkenylene chain of the heterocyclylalkenyl radical may be optionally substituted as defined above for an alkenylene chain. The heterocyclyl part of the heterocyclylalkenyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl(benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_t R^{22}$ (where t is 1 to 2), —$R^{21}$—N=C($OR^{20}$)$R^{20}$, —$R^{21}$—S(O)$_t OR^{22}$ where t is 1 to 2), —$R^{21}$—S(O)$_p R^{22}$ (where p is 0 to 2), and —$R^{21}$—S(O)$_t N(R^{20})_2$ (where t is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene or alkenylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula —$R_b R_i$ where $R_b$ is an alkylene chain as defined above and $R_i$ is a heteroaryl radical as defined above. The heteroaryl part of the heteroarylalkyl radical may be optionally substituted as defined above for a heteroaryl group. The alkylene chain part of the heteroarylalkyl radical may be optionally substituted as defined above for an alkylene chain.

"Heteroarylalkenyl" refers to a radical of the formula —$R_d R_i$ where $R_d$ is an alkenylene chain as defined above and $R_i$ is a heteroaryl radical as defined above. The heteroaryl part of the heteroarylalkenyl radical may be optionally substituted as defined above for a heteroaryl group. The alkenylene chain part of the heteroarylalkenyl radical may be optionally substituted as defined above for an alkenylene chain.

"Analgesia" refers to an absence of pain in response to a stimulus that would normally be painful.

"Allodynia" refers to a condition in which a normally innocuous sensation, such as pressure or light touch, is perceived as being extremely painful.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of the invention being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reducation, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its coversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving the disease or condition, i.e., causing regression of the disease or condition; or (d) relieving the symptoms resulting from the disease or condition, i.e., relieving pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Also within the scope of the invention are all polymorphs of the aforementioned species and crystal habits thereof.

The chemical naming protocol and structure diagrams used herein are a modified form of the I.U.P.A.C. nomenclature system, using the ACD/Name Version 9.07 software program, wherein the compounds of the invention are named herein as derivatives of a central core structure, e.g., the 2-oxindole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I) wherein n is 0, $R^1$ is tetrahydrofuranylmethyl, $R^2$ is hydrogen and $R^3$ is —O—Si($R^7$)$_3$ where $R^7$ is 1-methylethyl; i.e., a compound of the following formula:

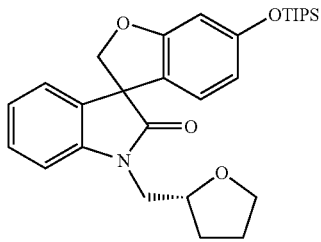

is named herein as 1-[(2R)-tetrahydrofuran-2-ylmethyl]-6-{[tris(1-methylethyl)silyl]oxy}spiro[1-benzofuran-3,3'-indol]-2'(1'H)-one.

Embodiments of the Invention

Of the various aspects of the invention set forth above in the Summary of the Invention, certain embodiments are preferred.

One embodiment of the invention is a compound of formula (I), as set forth above in the Summary of the Invention, as a stereoisomer, enantiomer or tautomer thereof or mixtures thereof; or a pharmaceutically acceptable salt, solvate or prodrug thereof. Of this embodiment, a preferred embodiment is wherein the compound of formula (I) is a compound of formula (I), as set forth above in the Summary of the Invention, as a stereoisomer, enantiomer or tautomer thereof or mixtures thereof; or a pharmaceutically acceptable salt.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0, 1, 2, 3 or 4;

$R^1$ is selected from the group consisting of hydrogen, —$R^5$—C(=NO$R^6$)N($R^7$)$R^8$, diphenylmethyl, aralkyl (optionally substituted with a substituent selected from the group consisting of —N($R^7$)$R^8$, —C(=NO$R^6$)N($R^7$)$R^8$, —O—$R^5$—C(O)O$R^7$, —O—$R^5$—C(O)N($R^7$)$R^8$ and —S(O)$R^7$) and heterocyclylalkyl (optionally substituted with —C(O)$R^7$);

$R^2$ is hydrogen;

$R^3$ is selected from the group consisting of —O—$R^5$—N($R^7$)$R^8$, —O—$R^5$—N($R^7$)C(O)O$R^8$, —O—$R^5$—C(O)O$R^7$, —O—Si($R^7$)$_3$ and —N[S(O)$_2R^7$]$_2$;

$R^4$ is selected from the group consisting of alkyl, halo, haloalkyl, aryl and aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)$R^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;

$R^1$ is selected from the group consisting of hydrogen, —$R^5$—C(=NO$R^6$)N($R^7$)$R^8$, diphenylmethyl, aralkyl (optionally substituted with a substituent selected from the group consisting of —N($R^7$)$R^8$, —C(=NO$R^6$)N($R^7$)$R^8$, —O—$R^5$—C(O)O$R^7$, —O—$R^5$—C(O)N($R^7$)$R^8$ and —S(O)$R^7$) and heterocyclylalkyl (optionally substituted with —C(O)$R^7$);

$R^2$ is hydrogen;

$R^3$ is selected from the group consisting of —O—$R^5$—N($R^7$)$R^8$, —O—$R^5$—N($R^7$)C(O)O$R^8$, —O—$R^5$—C(O)O$R^7$, —O—Si($R^7$)$_3$ and —N[S(O)$_2R^7$]$_2$;

each $R^5$ is an optionally substituted straight or branched alkylene chain;

$R^6$ is selected from the group consisting of hydrogen and —C(O)$R^7$; and each R⁷ and R⁸ is independently selected from the group consisting of hydrogen, alkyl, haloalkyl, optionally substituted cycloalkyl and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
R¹ is hydrogen;
R² is hydrogen;
R³ is selected from the group consisting of —O—R⁵—N(R⁷)R⁸ and —O—Si(R⁷)₃;
R⁵ is an optionally substituted straight or branched alkylene chain;
each R⁷ and R⁸ is independently selected from the group consisting of hydrogen, alkyl, haloalkyl, optionally substituted cycloalkyl and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:

6-[2-(dimethylamino)ethoxy]spiro[1-benzofuran-3,3'-indol]-2'(1'H)-one; and
6-{[tris(1-methylethyl)silyl]oxy}spiro[1-benzofuran-3,3'-indol]-2'(1'H)-one.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
R¹ is diphenylmethyl;
R² is hydrogen;
R³ is —O—R⁵—N(R⁷)R⁸;
R⁵ is an optionally substituted straight or branched alkylene chain;
R⁷ and R⁸ are each independently selected from the group consisting of hydrogen, alkyl, haloalkyl, optionally substituted cycloalkyl and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
R¹ is diphenylmethyl;
R² is hydrogen;
R³ is —O—R⁵—N(R⁷)R⁸;
R⁵ is an optionally substituted straight or branched alkylene chain;
R⁷ and R⁸ are each independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is 6-[2-(dimethylamino)ethoxy]-1'-(diphenylmethyl)spiro[1-benzofuran-3,3'-indol]-2'(1'H)-one.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
R¹ is heterocyclylalkyl (optionally substituted with —C(O)R⁷);
R² is hydrogen;
R³ is selected from the group consisting of —O—R⁵—N(R⁷)R⁸, —O—R⁵—N(R⁷)C(O)OR⁸, —O—R⁵—C(O)OR⁷, —O—Si(R⁷)₃ and —N[S(O)₂R⁷]₂;
each R⁵ is an optionally substituted straight or branched alkylene chain; and
each R⁷ and R⁸ is independently selected from the group consisting of hydrogen, alkyl, haloalkyl, optionally substituted cycloalkyl and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
R¹ is tetrahydrofuranylmethyl;
R² is hydrogen;
R³ is selected from the group consisting of —O—R⁵—N(R⁷)R⁸, —O—R⁵—N(R⁷)C(O)OR⁸, —O—R⁵—C(O)OR⁷, —O—Si(R⁷)₃ and —N[S(O)₂R⁷]₂;
each R⁵ is straight or branched alkylene chain; and
each R⁷ and R⁸ is independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:

1'-[(2R)-tetrahydrofuran-2-ylmethyl]-6-{[tris(1-methylethyl)silyl]oxy}spiro[1-benzofuran-3,3'-indol]-2'(1'H)-one;
N-(methylsulfonyl)-N-{2'-oxo-1'-[(2R)-tetrahydrofuran-2-ylmethyl]-1',2'-dihydrospiro[1-benzofuran-3,3'-indol]-6-yl}methanesulfonamide;
tert-butyl[1-methyl-2-({2'-oxo-1'-[(2R)-tetrahydrofuran-2-ylmethyl]-1',2'-dihydrospiro[1-benzofuran-3,3'-indol]-6-yl}oxy)ethyl]carbamate;
6-(2-aminopropoxy)-1'-[(2R)-tetrahydrofuran-2-ylmethyl]spiro[1-benzofuran-3,3'-indol]-2'(1H)-one hydrochloride;
6-[2-(dimethylamino)ethoxy]-1'-[(2R)-tetrahydrofuran-2-ylmethyl]spiro[1-benzofuran-3,3'-indol]-2'(1'H)-one;
methyl({2'-oxo-1'-[(2R)-tetrahydrofuran-2-ylmethyl]-1',2'-dihydrospiro[1-benzofuran-3,3'-indol]-6-yl}oxy)acetate; and
({2'-oxo-1'-[(2R)-tetrahydrofuran-2-ylmethyl]-1',2'-dihydrospiro[1-benzofuran-3,3'-indol]-6-yl}oxy)acetic acid.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0, 1, 2, 3 or 4;
R¹ is selected from the group consisting of hydrogen, —R⁵—C(=NOR⁶)N(R⁷)R⁸, diphenylmethyl, aralkyl (optionally substituted with a substituent selected from the group consisting of —N(R⁷)R⁸, —C(=NOR⁶)N(R⁷)R⁸, —O—R⁵—C(O)OR⁷, —O—R⁵—C(O)N(R⁷)R⁸ and —S(O)R⁷) and heterocyclylalkyl (optionally substituted with —C(O)R⁷);

$R^2$ and $R^3$, together with the carbons to which they are attached, form a fused O-heterocyclyl ring optionally substituted by =NOR$^7$;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)R$^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0 or 1;

$R^1$ is selected from the group consisting of hydrogen, —R$^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—C(O)OR$^7$, —O—R$^5$—C(O)N(R$^7$)R$^8$ and —S(O)R$^7$) and heterocyclylalkyl (optionally substituted with —C(O)R$^7$);

$R^2$ and $R^3$, together with the carbons to which they are attached, form a fused O-heterocyclyl ring optionally substituted by =NOR$^7$;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)R$^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0 or 1;

$R^1$ is selected from the group consisting of hydrogen, —R$^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—C(O)OR$^7$, —O—R$^5$—C(O)N(R$^7$)R$^8$ and —S(O)R$^7$) and heterocyclylalkyl (optionally substituted with —C(O)R$^7$);

$R^2$ and $R^3$, together with the carbons to which they are attached, form a fused [1,3]-dioxolyl;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)R$^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0 or 1;

$R^1$ is —R$^5$—C(=NOR$^6$)N(R$^7$)R$^8$;

$R^2$ and $R^3$, together with the carbons to which they are attached, form a fused [1,3]-dioxolyl;

$R^4$ is halo;

$R^5$ is an optionally substituted straight or branched alkylene chain;

$R^6$ is selected from the group consisting of hydrogen and —C(O)R$^7$; and each $R^7$ and $R^8$ is independently selected from the group consisting of hydrogen, alkyl and optionally substituted cycloalkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:

N'-hydroxy-3-(2'-oxo-6H-spiro[benzofuro[6,5-d][1,3]dioxole-7,3'-indoline]-1'-yl)propanimidamide;

2-(4'-chloro-2'-oxospiro[furo[2,3-f][1,3]benzodioxole-7,3'-indol]-1'(2'H)-yl)-N'-[(cyclopropylcarbonyl)oxy]ethanimidamide; and (1Z)-N'-hydroxy-2-(2'-oxospiro[furo[2,3-f][1,3]benzodioxole-7,3'-indol]-1'(2'H)-yl)ethanimidamide.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;

$R^1$ is aralkyl optionally substituted with a substituent selected from —N(R$^7$)R$^8$;

$R^2$ and $R^3$, together with the carbons to which they are attached, form a fused [1,3]-dioxolyl;

each $R^5$ is independently selected from the group consisting of an optionally substituted straight or branched alkylene chain; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
$R^1$ is benzyl optionally substituted with a substituent selected from —N($R^7$)$R^8$;
$R^2$ and $R^3$, together with the carbons to which they are attached, form a fused [1,3]-dioxolyl;
$R^7$ and $R^8$ are each independently selected from the group consisting of hydrogen and optionally substituted pyrrolidinyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:
tert-butyl (3R)-3-({4-[(2'-oxospiro[furo[2,3-f][1,3]benzodioxole-7,3'-indol]-1'(2'H)-yl)methyl]phenyl}-amino)pyrrolidine-1-carboxylate;
1'-{4-[(3R)-pyrrolidin-3-ylamino]benzyl}spiro[furo[2,3-f][1,3]benzodioxole-7,3'-indol]-2'(1'H)-one, and
1'-{4-[(3R)-pyrrolidin-3-ylamino]benzyl}spiro[furo[2,3-f][1,3]benzodioxole-7,3'-indol]-2'(1'H)-one hydrochloride.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
$R^1$ is aralkyl (optionally substituted with a substituent selected from the group consisting of —N($R^7$)$R^8$, —C(=NOR$^6$)N($R^7$)$R^8$, —O—$R^5$—C(O)O$R^7$, —O—$R^5$—C(O)N($R^7$)$R^8$ and —S(O)$R^7$) and heterocyclylalkyl (optionally substituted with —C(O)$R^7$);
$R^2$ and $R^3$, together with the carbons to which they are attached, form a fused dihydrofuranyl optionally substituted by =NOR$^7$;
each $R^5$ is independently an optionally substituted straight or branched alkylene chain;
$R^6$ is selected from the group consisting of hydrogen and —C(O)$R^7$; and
each $R^7$ and $R^8$ is independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
$R^1$ is benzyl optionally substituted with a substituent selected from the group consisting of —N($R^7$)$R^8$, —C(=NOR$^6$)N($R^7$)$R^8$, —O—$R^6$—C(O)O$R^7$, —O—$R^5$—C(O)N($R^7$)$R^8$ and —S(O)$R^7$;
$R^2$ and $R^3$, together with the carbons to which they are attached, form a fused dihydrofuranyl optionally substituted by =NOR$^7$;
each $R^5$ is independently an optionally substituted straight or branched alkylene chain;
$R^6$ is selected from the group consisting of hydrogen and —C(O)$R^7$; and
each $R^7$ and $R^8$ is independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:
N'-hydroxy-4-[(2'-oxo-5,6-dihydrospiro[benzo[1,2-b:5,4-b']difuran-3,3'-indol]-1'(2'H)-yl)methyl]benzenecarboximidamide;
N'-hydroxy-3-[(2'-oxo-5,6-dihydrospiro[benzo[1,2-b:5,4-b']difuran-3,3'-indol]-1'(2'H)-yl)methyl]benzenecarboximidamide;
2-{3-[(2'-oxo-5,6-dihydrospiro[benzo[1,2-b:5,4-b']difuran-3,3'-indol]-1'(2'H)-yl)methyl]phenoxy}acetamide;
2-{4-[(2'-oxo-5,6-dihydrospiro[benzo[1,2-b:5,4-b']difuran-3,3'-indol]-1'(2'H)-yl)methyl]phenoxy}acetamide;
ethyl {3-[(2'-oxo-5,6-dihydrospiro[benzo[1,2-b:5,4-b']difuran-3,3'-indol]-1'(2'H)-yl)methyl]phenoxy}acetate;
{3-[(2'-oxo-5,6-dihydrospiro[benzo[1,2-b:5,4-b']difuran-3,3'-indol]-1'(2'H)-yl)methyl]phenoxy}acetic acid;
2-(4-((2'-oxo-5,6-dihydro-2H-spiro[benzofuro[6,5-b]furan-3,3'-indoline]-1'-yl)methyl)phenoxy)acetic acid;
N-methyl-2-{3-[(2'-oxo-5,6-dihydrospiro[benzo[1,2-b:5,4-b']difuran-3,3'-indol]-1'(2'H)-yl)methyl]phenoxy}acetamide; and
1'-[4-(methylsulfinyl)benzyl]-5,6-dihydrospiro[benzo[1,2-b:5,4-b']difuran-3,3'-indol]-2'(1'H)-one.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
$R^1$ is independently selected from the group consisting of pyrrolidin-2-ylmethyl (optionally substituted with —C(O)$R^7$) and tetrahydrofuran-2-ylmethyl;
$R^2$ and $R^3$, together with the carbons to which they are attached, form a fused dihydrofuranyl optionally substituted by =NOR$^7$;
each $R^5$ is independently an optionally substituted straight or branched alkylene chain;
each $R^7$ is independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:
1'-{[(2S)-1-acetylpyrrolidin-2-yl]methyl}-5,6-dihydrospiro[benzo[1,2-b:5,4-b']difuran-3,3'-indol]-2'(1'H)-one; and
1'-[(2R)-tetrahydrofuran-2-ylmethyl]spiro[benzo[1,2-b:5,4-b']difuran-3,3'-indole]-2',5(1'H,6H)-dione 5-oxime.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;
$R^1$ is aralkyl (optionally substituted with a substituent selected from the group consisting of —N($R^7$)$R^8$, —C(=NOR$^6$)N($R^7$)$R^8$, —O—$R^5$—O$R^7$, —O—$R^5$—C(O)O$R^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);
$R^2$ and $R^3$, together with the carbons to which they are attached, form a fused [1,4]-dioxinyl;
each $R^5$ is independently an optionally substituted straight or branched alkylene chain;
$R^6$ is selected from the group consisting of hydrogen and —C(O)$R^7$; and each $R^7$ and $R^8$ is independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, wherein:

n is 0;

$R^1$ is benzyl optionally substituted with a substituent selected from the group consisting of —N($R^7$)$R^8$, —C(=NO$R^6$)N($R^7$)$R^8$, —O—$R^5$—O$R^7$, —O—$R^5$—C(O)O$R^7$, —O—$R^5$—C(O)N($R^7$)$R^8$, —O—$R^5$—N($R^7$)$R^8$ and —S(O)$R^7$;

$R^2$ and $R^3$, together with the carbons to which they are attached, form a fused [1,4]-dioxinyl;

each $R^5$ is independently an optionally substituted straight or branched alkylene chain;

$R^6$ is selected from the group consisting of hydrogen and —C(O)$R^7$; and each $R^7$ and $R^8$ is independently selected from the group consisting of hydrogen and alkyl.

Another embodiment is a compound of formula (I), as set forth above in the Summary of the Invention, as a stereoisomer, enantiomer or tautomer thereof or mixtures thereof; or a pharmaceutically acceptable salt, solvate or prodrug thereof, which is selected from the group consisting of:

2-{4-[(2'-oxo-2,3-dihydrospiro[furo[2,3-g][1,4]benzodioxine-8,3'-indol]-1'(2'H)-yl)methyl]phenoxy}acetamide;

1'-[4-(2-methoxyethoxy)benzyl]-2,3-dihydrospiro[furo[2,3-g][1,4]benzodioxine-8,3'-indol]-2'(1'H)-one;

1'-{4-[2-(dimethylamino)ethoxy]benzyl}-2,3-dihydrospiro[furo[2,3-g][1,4]benzodioxine-8,3'-indol]-2'(1'H)-one;

ethyl {4-[(2'-oxo-2,3-dihydrospiro[furo[2,3-g][1,4]benzodioxine-8,3'-indol]-1'(2'H)-yl)methyl]phenoxy}acetate;

{4-[(2'-oxo-2,3-dihydrospiro[furo[2,3-g][1,4]benzodioxine-8,3'-indol]-1'(2'H)-yl)methyl]phenoxy}acetic acid; and 1'-[4-(2-hydroxyethoxy)benzyl]-2,3-dihydrospiro[furo[2,3-g][1,4]benzodioxine-8,3'-indol]-2'(1'H)-one.

Another embodiment of the invention is a method of treating, preventing or ameliorating a disease or a condition in a mammal, preferably a human, wherein the disease or condition is selected from the group consisting of pain, depression, cardiovascular diseases, respiratory diseases, and psychiatric diseases, and combinations thereof, and wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

One embodiment of this embodiment is wherein the disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, peripheral nerve injury, and combinations thereof.

Another embodiment of this embodiment is wherein the disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythermalgia, primary erythermalgia, familial rectal pain, cancer, epilepsy, partial and general tonic seizures, restless leg syndrome, arrhythmias, fibromyalgia, neuroprotection under ischaemic conditions caused by stroke or neural trauma, tachy-arrhythmias, atrial fibrillation and ventricular fibrillation.

Another embodiment of the invention is the method of treating pain in a mammal, preferably a human, by the inhibition of ion flux through a voltage-dependent sodium channel in the mammal, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating or preventing hypercholesterolemia in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating or preventing benign prostatic hyperplasia in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating or preventing pruritis in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of treating or preventing cancer in a mammal, preferably a human, wherein the method comprises administering to the mammal in need thereof a therapeutically effective amount of an embodiment of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

Another embodiment of the invention is the method of decreasing ion flux through a voltage-dependent sodium channel in a cell in a mammal, wherein the method comprises contacting the cell with an embodiment of a compound of the invention, as set forth above, as a stereoisomer, enantiomer or tautomer thereof or mixtures thereof, or a pharmaceutically acceptable salt, solvate or prodrug thereof.

Specific embodiments of the compounds of the invention are described in more detail below in the Preparation of the Compounds of the Invention.

Utility and Testing of the Compounds of the Invention

The compounds of the invention modulate, preferably inhibit, ion flux through a voltage-dependent sodium channel in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a sodium channel downwards, inhibit the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel. Preferably, the compounds are state or frequency dependent modifiers of the sodium channels, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., *op. cit.*). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are sodium channel blockers and are therefore useful for treating diseases and conditions in mammals, preferably humans, and other organisms, including all those human diseases and conditions which are the result of aberrant voltage-dependent sodium channel biological activity or which may be ameliorated by modulation of voltage-dependent sodium channel biological activity.

As defined herein, a sodium channel-mediated disease or condition refers to a disease or condition in a mammal, preferably a human, which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

The present invention therefore relates to compounds, pharmaceutical compositions and methods of using the compounds and pharmaceutical compositions for the treatment of sodium channel-mediated diseases in mammals, preferably humans and preferably diseases related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a mammal, preferably a human, in need of such treatment an effective amount of a sodium channel blocker modulating, especially inhibiting, agent.

Accordingly, the present invention provides a method for treating a mammal for, or protecting a mammal from developing, a sodium channel-mediated disease, especially pain, comprising administering to the mammal, especially a human, in need thereof, a therapeutically effective amount of a compound of the invention or a pharmaceutical composition comprising a therapeutically effective amount of a compound of the invention wherein the compound modulates the activity of one or more voltage-dependent sodium channels.

The general value of the compounds of the invention in mediating, especially inhibiting, the sodium channel ion flux can be determined using the assays described below in the Biological Assays section. Alternatively, the general value of the compounds in treating conditions and diseases in humans may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, *Pain* (2000), 87:7-17). Allimetric scaling of the doses effective in these rat models, translates into doses similar to those shown to be efficacious in humans (Tanelian, D. L. and Brose, W. G., *Anesthesiology* (1991), 74(5):949-951). Furthermore, Lidoderm®, lidocaine applied in the form of a dermal patch, is currently an FDA approved treatment for post-herpetic neuralgia (Devers, A. and Glaler, B. S., *Clin. J. Pain* (2000), 16(3):205-8).

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g. opiate, benzodiazepine, amphetamine, cocaine, alcohol, butane inhalation), Alzheimer, dementia, age-related memory impairment, Korsakoff syndrome, restenosis, urinary dysfunction, incontinence, Parkinson's disease, cerebrovascular ischemia, neurosis, gastrointestinal disease, sickle cell anemia, transplant rejection, heart failure, myocardial infarction, reperfusion injury, intermittent claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congentia, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebelleear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythermalgia, primary erythermalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g. musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

Sodium channel blockers have clinical uses in addition to pain. Epilepsy and cardiac arrhythmias are often targets of sodium channel blockers. Recent evidence from animal models suggest that sodium channel blockers may also be useful for neuroprotection under ischaemic conditions caused by stroke or neural trauma and in patients with multiple sclerosis (MS) (Clare, J. J. et al., op. cit. and Anger, T. et al., op. cit.).

The present invention also relates to compounds, pharmaceutical compositions and methods of using the compounds and pharmaceutical compositions for the treatment or prevention of diseases or conditions such as benign prostatic hyperplasia (BPH), hypercholesterolemia, cancer and pruritis (itch).

Benign prostatic hyperplasia (BPH), also known as benign prostatic hypertrophy, is one of the most common diseases affecting aging men. BPH is a progressive condition which is characterized by a nodular enlargement of prostatic tissue resulting in obstruction of the urethra. Consequences of BPH can include hypertrophy of bladder smooth muscle, a decompensated bladder, acute urinary retention and an increased incidence of urinary tract infection.

BPH has a high public health impact and is one of the most common reasons for surgical intervention among elderly men. Attempts have been made to clarify the etiology and pathogenesis and, to that end, experimental models have been developed. Spontaneous animal models are limited to the chimpanzee and the dog. BPH in man and the dog share many common features. In both species, the development of BPH occurs spontaneously with advanced age and can be prevented by early/prepubertal castration. A medical alternative to surgery is very desirable for treating BHP and the consequences.

The prostatic epithelial hyperplasia in both man and the dog is androgen sensitive, undergoing involution with androgen deprivation and resuming epithelial hyperplasia when androgen is replaced. Cells originating from the prostate gland have been shown to express high levels of voltage gated sodium channels. Immunostaining studies clearly demonstrated evidence for voltage gated sodium channels in prostatic tissues (*Prostate Cancer Prostatic Dis.* 2005; 8(3):266-73).

Hypercholesterolemia, i.e., elevated blood cholesterol, is an established risk factor in the development of, e.g., atherosclerosis, coronary artery disease, hyperlipidemia, stroke, hyperinsulinemias, hypertension, obesity, diabetes, cardiovascular diseases (CVD), myocardial ischemia, and heart attack. Thus, lowering the levels of total serum cholesterol in individuals with high levels of cholesterol has been known to reduce the risk of these diseases. The lowering of low density lipoprotein cholesterol in particular is an essential step in the prevention of CVD. Although there are a variety of hypercholesterolemia therapies, there is a continuing need and a continuing search in this field of art for alternative therapies.

The invention provides compounds which are useful as antihypercholesterolemia agents and their related conditions. The present compounds may act in a variety of ways. While not wishing to be bound to any particular mechanism of action, the compounds may be direct or indirect inhibitors of the enzyme acyl CoA: cholesterol acyl transferase (ACAT) that results in inhibition of the esterification and transport of cholesterol across the intestinal wall. Another possibility may be that the compounds of the invention may be direct or indirect inhibitors of cholesterol biosynthesis in the liver. It is possible that some compounds of the invention may act as both direct or indirect inhibitors of ACAT and cholesterol biosynthesis.

Pruritus, commonly known as itch, is a common dermatological condition. While the exact causes of pruritis are complex and poorly understood, there has long been acknowledged to have interactions with pain. In particular, it is believed that sodium channels likely communicate or propagate along the nerve axon the itch signals along the skin. Transmission of the itch impulses results in the unpleasant sensation that elicits the desire or reflex to scratch.

From a neurobiology level, it is believed that there is a shared complexity of specific mediators, related neuronal pathways and the central processes of itch and pain and recent data suggest that there is a broad overlap between pain- and itch-related peripheral mediators and/or receptors (Ikoma et al., *Nature Reviews Neuroscience*, 7:535-547, 2006). Remarkably, pain and itch have similar mechanisms of neuronal sensitization in the peripheral nervous system and the central nervous system but exhibits intriguing differences as well.

For example, the mildly painful stimuli from scratching are effective in abolishing the itch sensation. In contrast, analgesics such as opioids can generate severe pruritus. The antagonistic interaction between pain and itch can be exploited in pruritus therapy, and current research concentrates on the identification of common targets for future analgesic and antipruritic therapy.

Compounds of the present invention have been shown to have analgesic effects in a number of animal models at oral doses ranging from 1 mg/Kg to 100 mg/Kg. The compounds of the invention can also be useful for treating pruritus.

The types of itch or skin irritation, include, but are not limited to:

a) psoriatic pruritis, itch due to hemodyalisis, aguagenic pruritus, and itching caused by skin disorders (e.g., contact dermatitis), systemic disorders, neuropathy, psychogenic factors or a mixture thereof;

b) itch caused by allergic reactions, insect bites, hypersensitivity (e.g., dry skin, acne, eczema, psoriasis), inflammatory conditions or injury;

c) itch associated with vulvar vestibulitis; and d) skin irritation or inflammatory effect from administration of another therapeutic such as, for example, antibiotics, antivirals and antihistamines.

The compounds of the invention are also useful in treating or preventing certain hormone sensitive cancers, such as prostate cancer (adenocarcinoma), breast cancer, ovarian cancer, testicular cancer, thyroid neoplasia, in a mammal, preferably a human. The voltage gated sodium channels have been demonstrated to be expressed in prostate and breast cancer cells. Up-regulation of neonatal $Na_v1.5$ occurs as an integral part of the metastatic process in human breast cancer and could serve both as a novel marker of the metastatic phenotype and a therapeutic target (*Clin. Cancer Res.* 2005, Aug. 1; 11(15): 5381-9). Functional expression of voltage-gated sodium channel alpha-subunits, specifically $Na_v1.7$, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (*Prostate Cancer Prostatic Dis.*, 2005; 8(3):266-73).

The compounds of the invention are also useful in treating or preventing symptoms in a mammal associated with BPH such as, but not limited to, acute urinary retention and urinary tract infection.

The compounds of the invention are also useful in treating or preventing certain endocrine imbalances or endocrinopathies such as congenital adrenal hyperplasia, hyperthyroidism, hypothyroidism, osteoporosis, osteomalacia, rickets, Cushing's Syndrome, Conn's syndrome, hyperaldosteronism, hypogonadism, hypergonadism, infertility, fertility and diabetes.

The present invention readily affords many different means for identification of sodium channel modulating agents that are useful as therapeutic agents. Identification of modulators of sodium channel can be assessed using a variety of in vitro and in vivo assays, e.g. measuring current, measuring membrane potential, measuring ion flux, (e.g. sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

A competitive binding assay with known sodium channel toxins such as tetrodotoxin, alpha-scorpion toxins, aconitine, BTX and the like, may be suitable for identifying potential therapeutic agents with high selectivity for a particular sodium channel. The use of BTX in such a binding assay is well known and is described in McNeal, E. T., et al., *J. Med. Chem.* (1985), 28(3):381-8; and Creveling, C. R., et al., *Methods in Neuroscience*, Vol. 8: Neurotoxins (Conn PM Ed) (1992), pp. 25-37, Academic Press, New York.

These assays can be carried out in cells, or cell or tissue extracts expressing the channel of interest in a natural endogenous setting or in a recombinant setting. The assays that can be used include plate assays which measure Na+ influx through surrogate markers such as $^{14}$C-guanidine influx or determine cell depolarization using fluorescent dyes such as the FRET based and other fluorescent assays or a radiolabelled binding assay employing radiolabelled aconitine, BTX, TTX or STX. More direct measurements can be made with manual or automated electrophysiology systems. The guanidine influx assay is explained in more detail below in the Biological Assays section.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.)

which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available, however these are of only limited functional value and information content. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they alleviate pain, especially chronic pain or other conditions such as arrhythmias and epilepsy, benign prostatic hyperplasia (BPH), hypercholesterolemia, cancer and pruritis (itch) with minimal adverse events. The assays described below in the Biological Assays Section are useful in assessing the biological activity of the instant compounds.

Typically, a successful therapeutic agent of the present invention will meet some or all of the following criteria. Oral availability should be at or above 20%. Animal model efficacy is less than about 0.1 µg to about 100 mg/Kg body weight and the target human dose is between 0.1 µg to about 100 mg/Kg body weight, although doses outside of this range may be acceptable ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 µM, preferably below 1 µM and most preferably below 50 nM. The $IC_{50}$ ("Inhibitory Concentration-50%") is a measure of the amount of compound required to achieve 50% inhibition of ion flux through a sodium channel, over a specific time period, in an assay of the invention. Compounds of the present invention in the guanidine influx assay have demonstrated $IC_{50}$'s ranging from less than a nanomolar to less than 10 micromolar.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_V1.1$, $Na_V1.2$, $Na_V1.3$, $Na_V1.4$, $Na_V1.5$, $Na_V1.6$, $Na_V1.7$, $Na_V1.8$, or $Na_V1.9$ activity in a biological sample or a mammal, preferably a human, which method comprises administering to the mammal, preferably a human, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_V1.1$, $Na_V1.2$, $Na_V1.3$, $Na_V1.4$, $Na_V1.5$, $Na_V1.6$, $Na_V1.7$, $Na_V1.8$, or $Na_V1.9$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer or tautomer thereof or mixtures thereof, or a pharmaceutically acceptable salt, solvate or prodrug thereof, can be used in the preparation of a medicament for the treatment of sodium channel-mediated disease or condition in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as pain, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., *The Merck Manual*, $16^{th}$ edition, Merck and Co., Rahway, N.J., 1992; Goodmanetna., eds., *Goodman and Cilman's The Pharmacological Basis of Therapeutics*, $10^{th}$ edition, Pergamon Press, Inc., Elmsford, N.Y., (2001); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, $18^{th}$ edition, Mack Publishing Co., Easton, Pa. (1990); Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transportionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of sodium channel-mediated diseases and conditions. For example, a compound of the invention may be administered simultaneously, sequentially or separately in combination with other therapeutic agents, including, but not limited to:

opiates analgesics, e.g. morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g. acetomeniphen, salicylates (e.g. aspirin);

nonsteroidal antiinflammatory drugs (NSAIDs), e.g. ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g. carbamazepine, oxcarbazepine, lamotrigine, valproate, topiramate, gabapentin and pregabalin;

antidepressants such as tricyclic antidepressants, e.g. amitriptyline, clomipramine, despramine, imipramine and nortriptyline;

COX-2 selective inhibitors, e.g. celecoxib, rofecoxib, parecoxib, valdecoxib, deracoxib, etoricoxib, and lumiracoxib;

alpha-adrenergics, e.g. doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g. amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g. (αR,9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

coal-tar analgesics, in particular paracetamol;

serotonin reuptake inhibitors, e.g. paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g. maprotiline, lofepramine, mirtazepine, oxaprotiline, fezolamine, tomoxetine, mianserin, buprorion, buprorion metabolite hydroxybuprorion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT$_3$ antagonists such as ondansetron;

metabotropic glutamate receptor (mGluR) antagonists;

local anaesthetic such as mexiletine and lidocaine;

corticosteroid such as dexamethasone;

antiarrhythimics, e.g. mexiletine and phenyloin;

muscarinic antagonists, e.g., tolterodine, propiverine, tropsium t chloride, darifenacin, solifenacin, temiverine and ipratropium;

cannabinoids;

vanilloid receptor agonists (e.g. resinferatoxin) or antagonists (e.g. capsazepine);

sedatives, e.g. glutethimide, meprobamate, methaqualone, and dichloralphenazone;

anxiolytics such as benzodiazepines, antidepressants such as mirtazapine, topical agents (e.g. lidocaine, capsacin and resiniferotoxin);

muscle relaxants such as benzodiazepines, baclofen, carisoprodol, chlorzoxazone, cyclobenzaprine, methocarbamol and orphenadrine;

anti-histamines or H1 antagonists;

NMDA receptor antagonists;

5-HT receptor agonists/antagonists;

PDEV inhibitors;

Tramadol®;

cholinergic (nicotinc) analgesics;

alpha-2-delta ligands;

prostaglandin E2 subtype antagonists;

leukotriene B4 antagonists;

5-lipoxygenase inhibitors; and

5-HT$_3$ antagonists.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for modulating the activity of ion channels, for the treatment of pain, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of this invention, i.e., compounds of formula (I):

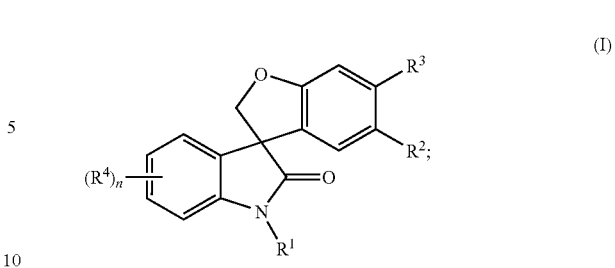

wherein n, $R^1$, $R^2$, $R^3$ and $R^4$ are as described above in the Summary of the Invention, as a stereoisomer, enantiomer or tautomer thereof or mixtures thereof; or a pharmaceutically acceptable salt, solvate or prodrug thereof.

It is also understood that one skilled in the art would be able to make the compounds of the invention by similar methods or by methods known to one skilled in the art. For example, the compounds of the invention can be prepared according to methods similar to those described in PCT Published Patent Application, WO 2006/110917. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry Reactions*, Mechanisms, and Structure, 5th edition (Wiley, December 2000)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein. The use of protecting groups is described in detail in Greene, T. W. and P. G. M. Wuts, *Greene's Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one skilled in the art would be able to make these compounds by similar methods or by methods known to one skilled in the art. It is also understood that one skilled in the art would be able to make in a similar manner as described below other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry: Reactions*, Mechanisms, and Structure, 5th edition (Wiley, December 2000)) or prepared as described herein.

Compounds of formula (I), as set forth above in the Summary of the Invention, can be prepared following the general procedure as described below in REACTION SCHEME 1, where n, $R^1$, $R^2$, $R^3$ and $R^4$ are as defined above in the Summary of the Invention for compounds of formula (I), X is Cl or Br and R" is an alkyl group.

REACTION SCHEME 1

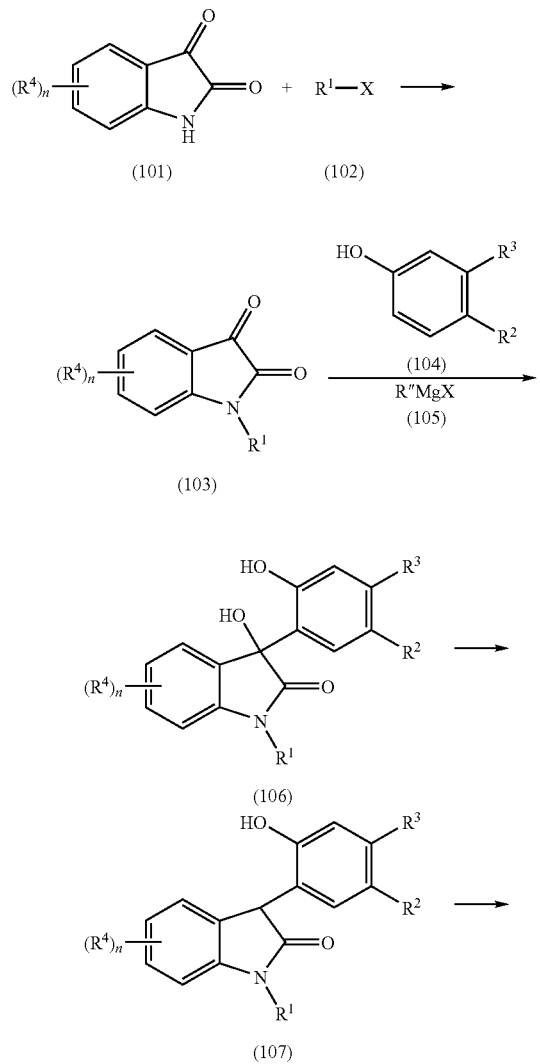

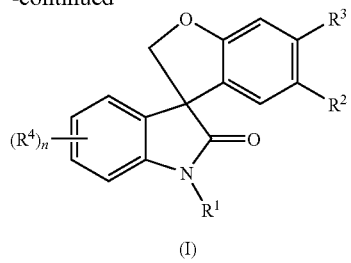

Compounds of formula (101), formula (102), formula (104) and formula (105) are commercially available or can be prepared according to methods known to one skilled in the art or by the methods disclosed herein or by the methods disclosed in PCT Published Patent Application WO 2006/110917.

As set forth above, an isatin compound of formula (101) is alkylated with the chloro or bromo compound of formula (102) to afford the product of formula (103). The phenol compound of formula (104) is treated with a Grignard reagent of formula (105) at low temperature (0° C.) to form the phenoxymagnesium halide intermediate which reacts with the keto-carbonyl group of the isatin compound of formula (103) in a solvent, such as, but not limited to, methylene chloride or tetrahydrofuran, to afford the oxindole of formula (106). The compound of formula (107) is obtained after the removal of the hydroxyl group at C-3 position of the oxindole by treating the compound of formula (106) with silane such as triethylsilane. The compound of formula (107) can also be achieved by treating the compound of formula (106) with thionyl chloride/triethylamine then reduction with zinc dust. Compound of formula (107) is treated with chloroiodomethane in the presence of a base, such as, but not limited to, cesium carbonate, in a solvent, such as, but not limited to, tetrahydrofuran to afford a compound of formula (I) of the invention via intramolecular cyclization.

An alternative synthesis of the compounds of formula (I) wherein different $R^1$ groups are introduced is illustrated below in REACTION SCHEME 2 where n, $R^1$, $R^2$, $R^3$ and $R^4$ are as described above in the Summary of the Invention for compounds of formula (I), and PG is a nitrogen-protecting group:

REACTION SCHEME 2

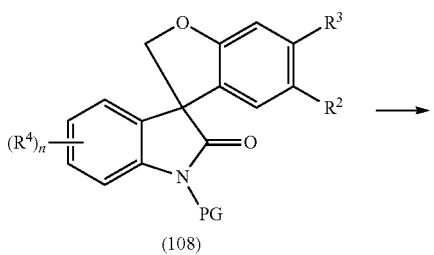

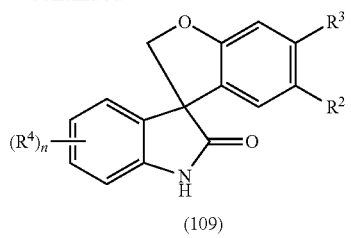

(109)

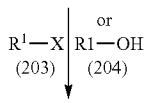

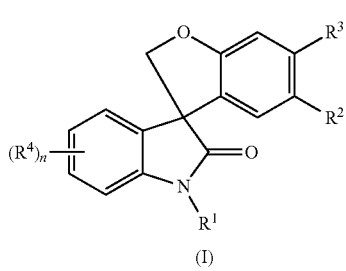

(I)

Compounds of formula (108) can be prepared according to methods known to one skilled in the art or by the methods disclosed herein (such as the methods disclosed above in REACTION SCHEME 1) or by the methods disclosed in PCT Published Patent Application WO 2006/110917.

As set forth above, when the protecting group is diphenylmethyl, it is removed from the compound of formula (108) under a high pressure of hydrogen such as 60-120 psi to form the oxindole compound of formula (109). Alternatively the diphenylmethyl group is removed by treatment of compound of formula (108) with triethyl silane and trifluoroacetic acid at 70 to 100° C. The formation of a compound of formula (I) is achieved by alkylation of the compound of formula (109) with a halide reagent $XR^1$ (where X is chloro, bromo or iodo) or a tosylate reagent $TsOR^1$ in the presence of a base such as, but not limited to, sodium hydride, sodium bis(trimethylsilyl)amide, lithium hydroxide, or cesium carbonate, in a solvent such as, but not limited to, N,N-dimethylformamide, tetrahydrofuran, 2-butanone, acetone or acetonitrile. Alternatively, reaction of compound of formula (109) with an alcohol under Mitsunobu reaction conditions in the presence of a phosphine reagent such as, but not limited to, triphenylphosphine, tributylphosphine or trimethyl phosphine, and azadicarboxylate of diethyl, diisopropyl or di-tert-butyl in a solvent such as, but not limited to, tetrahydrofuran, ethyl acetate or dichloromethane, provides the compound of formula (I).

Compounds of formula (I) wherein $R^1$ is aralkyl substituted with $-O-R^5-C(O)OR^7$ or $-O-R^5-C(O)N(R^7)R^8$ where $R^5$, $R^7$ and $R^8$ are as described above in the Summary of the Invention, can be prepared in a similar manner as described below in REACTION SCHEME 3 where n, $R^2$, $R^3$, $R^4$, $R^5$, $R^7$ and $R^8$ are as described above in the Summary of the Invention, Z is $-C(O)NH_2$, $-N(CH_3)_2$ or $-OCH_3$, X is Cl, Br or I, Bn is benzyl and Et is ethyl:

REACTION SCHEME 3

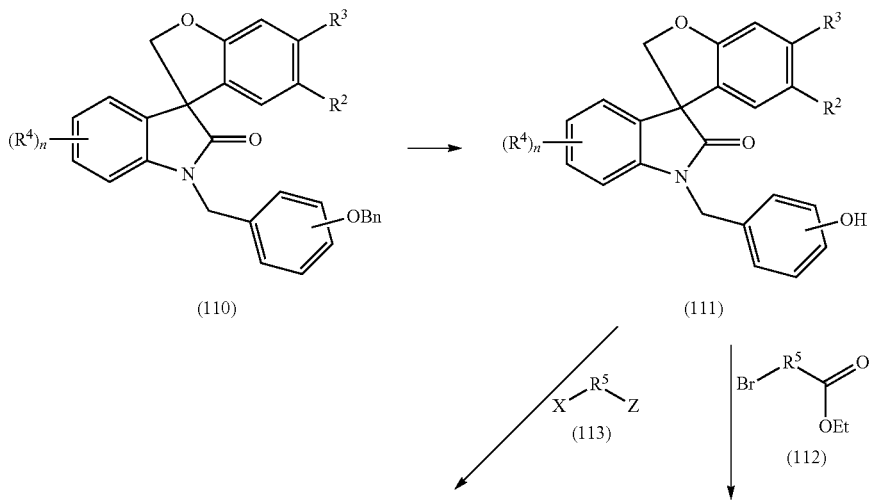

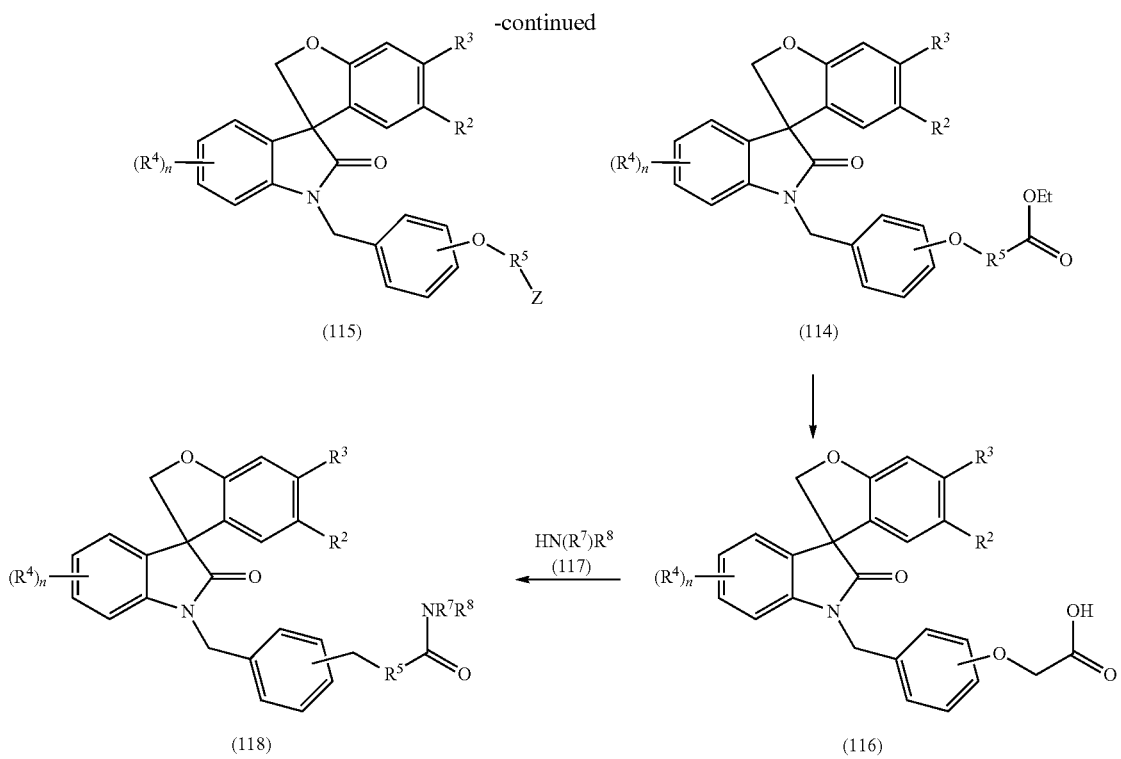

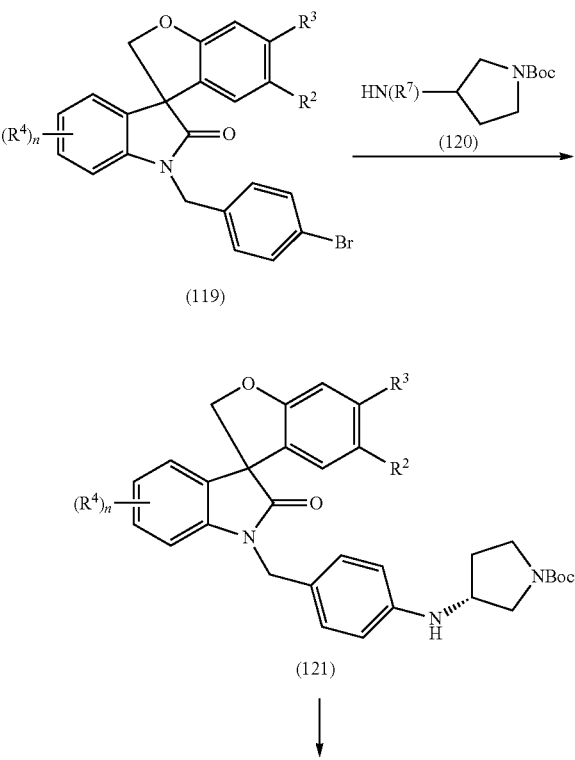

Compounds of formula (110) can be prepared according to methods known to one skilled in the art or by the methods disclosed herein or by the methods disclosed in PCT Published Patent Application WO 2006/110917. Compounds of formula (112), (113) and (117) are commercially available, or can be prepared according to methods known to one skilled in the art.

As set forth above, a phenol compound of formula (111) is synthesized by hydrogenation of compound of formula (110) with a catalyst such as, but not limited to, palladium on carbon, in a solvent such as, but not limited to, methanol. The formation of an alkylated compound of formula (115), a compound of formula (I), is achieved by alkylation of the compound of formula (111) with a compound of formula (113), e.g., 2-iodoacetamide, in the presence of a base such as, but not limited to, potassium carbonate, in a solvent such as, but not limited to, N,N-dimethylformamide. The compound of formula (114) can also be synthesized by alkylation of the compound of formula (111) with a compound of formula (112), e.g., ethyl bromoacetate, in the presence of a base such as, but not limited to, potassium carbonate, in a solvent such as, but not limited to, N,N-dimethylformamide. Hydrolysis of compound of formula (114) in the presence of a base such as, but not limited to, lithium hydroxide affords acid compound of formula (116). The acid compound of formula (116) is converted to the corresponding acid chloride, by treatment with oxalyl chloride in the presence of catalytic amount of N,N-dimethylformamide in a solvent such as, but not limited to, chloroform. The acid chloride reacts with a primary or secondary amine of formula (117) in the presence of a base such as, but not limited to, triethylamine to form the amide compound of formula (118), a compound of formula (I).

Compounds of formula (I) wherein $R^1$ is aralkyl substituted with —$N(R^7)R^8$ wherein one of $R^7$ and $R^8$ is hydrogen and the other is optionally substituted heterocyclyl, e.g., pyrrolidin-3-yl, can be prepared in a similar manner as described below in REACTION SCHEME 4 where n, $R^2$, $R^3$, $R^4$ and $R^7$ are as described above in the Summary of the Invention, preferably $R^7$ is hydrogen, and Boc is t-butoxycarbonyl:

REACTION SCHEME 4

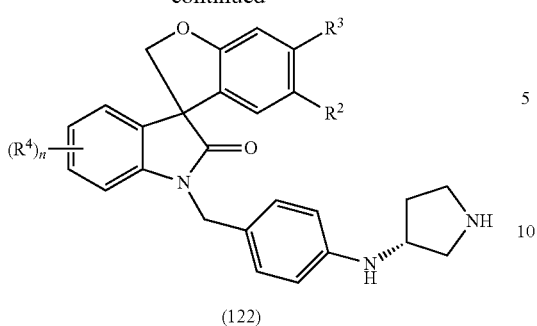

(122)

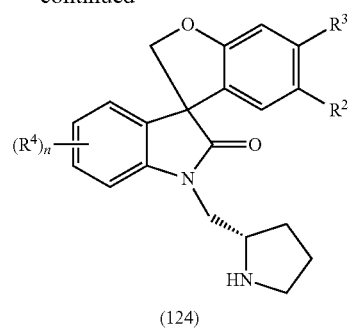

(124)

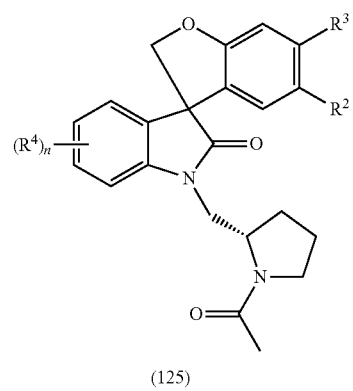

(125)

Compounds of formula (119) can be prepared according to methods known to one skilled in the art or by the methods disclosed herein or by the methods disclosed in PCT Published Patent Application WO 2006/110917. Compounds of formula (120), are commercially available, or can be prepared according to methods known to one skilled in the art.

As set forth above, compounds of formula (119) are reacted with a primary or secondary amine of formula (120) in the presence of a palladium catalyst such as, but not limited to, tris(dibenzylideneacetone)dipalladium(0), with a ligand such as, but not limited to, (±)-2,2'-bis(diphenylphosphino)-1,1'-binaphthalene, with a base such as, but not limited to, sodium tert-butoxide, in a solvent such as, but not limited to, toluene, to provide the amino compound of formula (121) as compounds of formula (I) (see Muci, A. R. et al., *Topics in Current Chemistry* (2002), 219:131). The compound of formula (122), a compound of formula (I), is synthesized by deprotection of the compound of formula (121) with an acid, such as, but not limited to, trifluoroacetic acid or hydrochloride in diethyl ether, in a solvent such as, but not limited to, dichloromethane or methanol.

Compounds of formula (I) wherein $R^1$ is heterocyclyl, preferably pyrrolidinyl, substituted —C(O)$R^7$ where $R^7$ is as described above in the Summary of the Invention, preferably alkyl, even more preferably methyl, can be prepared in a similar manner as described below in REACTION SCHEME 5 where n, $R^2$, $R^3$ and $R^4$ are as described above in the Summary of the Invention and Boc is t-butoxycarbonyl:

REACTION SCHEME 5

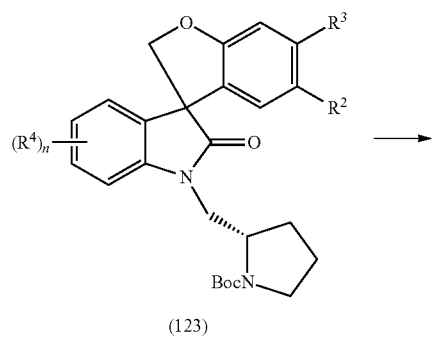

(123)

Compounds of formula (123) can be prepared according to methods known to one skilled in the art or by the methods disclosed herein or by the methods disclosed in PCT Published Patent Application WO 2006/110917.

As set forth above, a compound of formula (124) is synthesized by deprotection of a compound of formula (123) with an acid, such as, but not limited to, trifluoroacetic acid or hydrochloride in diethyl ether, in a solvent such as, but not limited to, dichloromethane or methanol. The compound of formula (124) is converted to a compound of formula (125), a compound of formula (I) by treatment of acetic anhydride in the presence of a base such as, but not limited to, triethyl amine, in a solvent such as, but not limited to, dichloromethane.

Compounds of formula (I) where $R^1$ is —$R^5$—C(=NOR$^6$)N(R$^7$)R$^8$ or aralkyl substituted with —C(=NOR$^6$)N(R$^7$)R$^8$ where each $R^5$, $R^6$, $R^7$ and $R^8$ is as defined above in the Summary of the Invention, can be prepared in a similar manner as described below in REACTION SCHEME 6 where n, $R^2$, $R^3$ and $R^4$ are as described above in the Summary of the Invention and B is an straight or branched alkylene chain or an aralkyl:

REACTION SCHEME 6

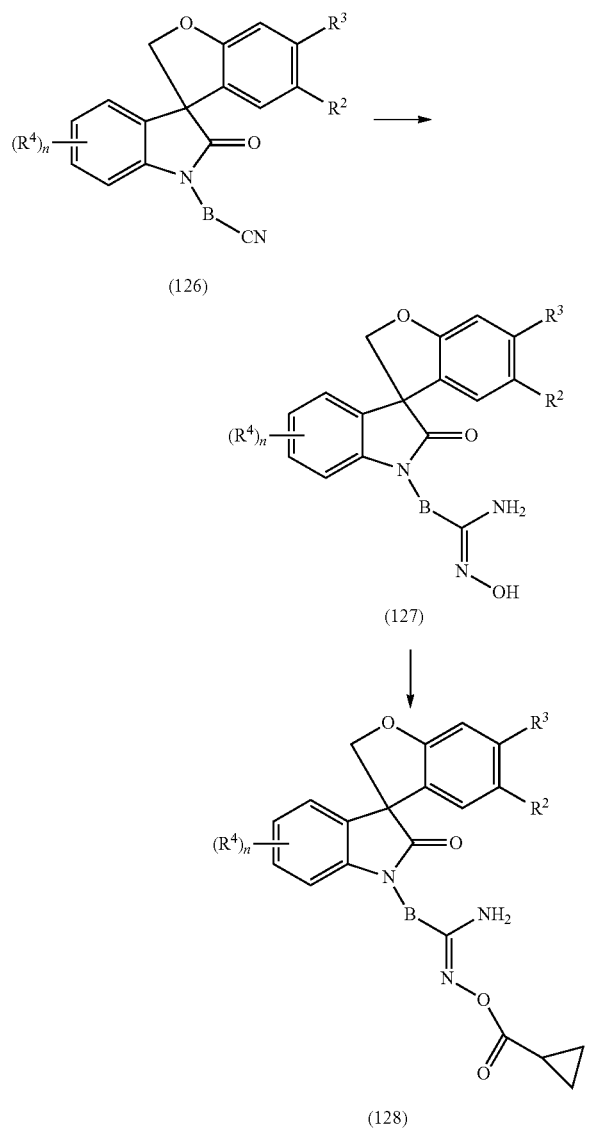

REACTION SCHEME 7

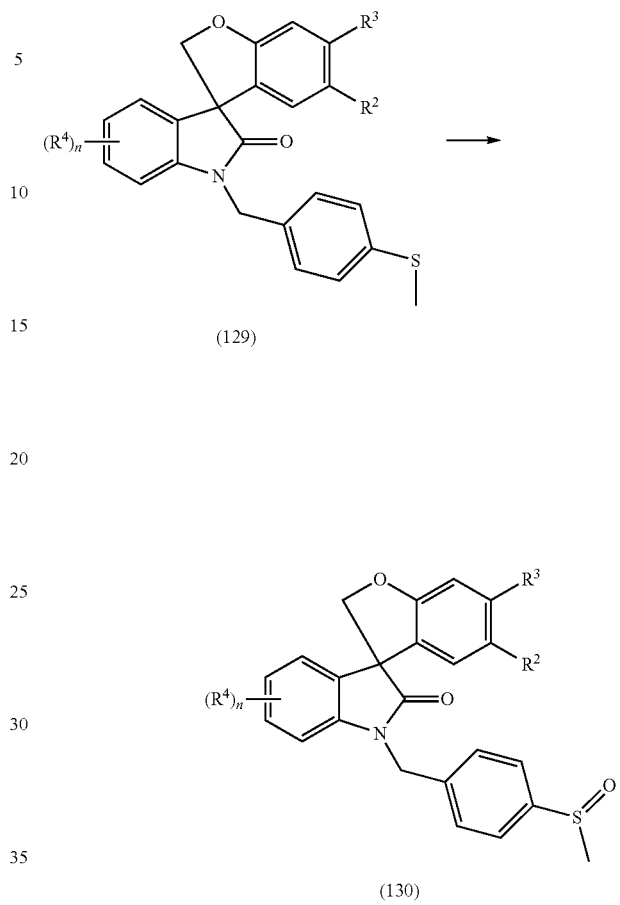

Compounds of formula (126) can be prepared according to methods known to one skilled in the art or by the methods disclosed herein or by the methods disclosed in PCT Published Patent Application WO 2006/110917.

As set forth above, a compound of formula (127) is obtained by treating a compound of formula (126) with hydroxylamine in a solvent such as, but not limited to, dimethyl sulfoxide. The compound of formula (127) is then converted to a compound of formula (128), a compound of formula (I), by treatment of cyclopropane carbonyl chloride in the presence of a base such as, but not limited to, diisopropyl amine, in a solvent such as, but not limited to, dichloromethane.

Compounds of formula (I) where $R^1$ is aralkyl, preferably benzyl, substituted with —S(O)$R^7$ where $R^7$ is as defined above in the Summary of the Invention, preferably alkyl, can be prepared in a similar manner as described below in REACTION SCHEME 7 where n, $R^2$, $R^3$ and $R^4$ are as described above in the Summary of the Invention:

Compounds of formula (129) can be prepared according to methods known to one skilled in the art or by the methods disclosed herein or by the methods disclosed in PCT Published Patent Application WO 2006/110917.

As set forth above, a compound of formula (130), a compound of formula (I), is synthesized by oxidation of a compound of formula (129) with oxidant such as, but not limited to, sodium metaperiodate in a solvent such as, but not limited to, water.

Compounds of formula (I) where $R^3$ is —N[S(O)$_2R^7$]$_2$ where $R^7$ is as described above in the Summary of the Invention, can be prepared in a similar manner as described below in REACTION SCHEME 8 where n, $R^1$, $R^2$, $R^4$ and each $R^7$ are as described above in the Summary of the Invention:

REACTION SCHEME 8

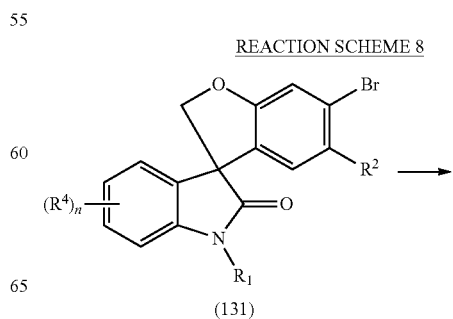

-continued

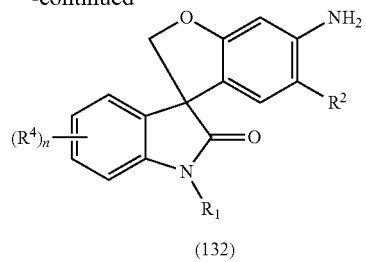

(132)

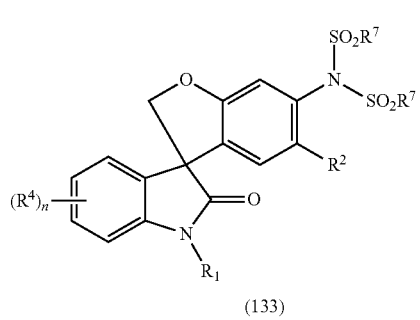

(133)

Compounds of formula (131) can be prepared according to methods known to one skilled in the art or by the methods disclosed herein or by the methods disclosed in PCT Published Patent Application WO 2006/110917.

As set forth above, a compound of formula (131) is reacted with benzophenone imine in the presence of a palladium catalyst such as, but not limited to, tris(dibenzylideneacetone)dipalladium(0), with a ligand such as, but not limited to, (±)-2,2'-bis(diphenylphosphino)-1,1'-binaphthalene, with a base such as, but not limited to, sodium tert-butoxide, in a solvent such as, but not limited to, dioxane or tetrahedrofuran, to provide an intermediate imino compound which is then deprotected by treatment with an acid such as, but not limited to, hydrochloride to afford a compound of formula (132). The compound of formula (132) is reacted with methanesulfonyl chloride in the presence of a base such as, but not limited to, triethylamine in a solvent such as, but not limited to, dichloromethane to form the sulfonamide compound (133), a compound of formula (I) as formula (I).

Compounds of formula (I) where $R^3$ is $-O-R^5-N(R^7)R^8$ where $R^5$, $R^7$ and $R^8$ are as described above in the Summary of the Invention, preferably where $R^5$ is methylene, and $R^7$ and $R^8$ are both alkyl, can be prepared in a similar manner as described below in REACTION SCHEME 9 where n, $R^1$, $R^2$ and $R^4$ are as described above in the Summary of the Invention, X is chloro, bromo or iodo, Ts is tosyl, Ph is phenyl and Bn is benzyl:

REACTION SCHEME 9

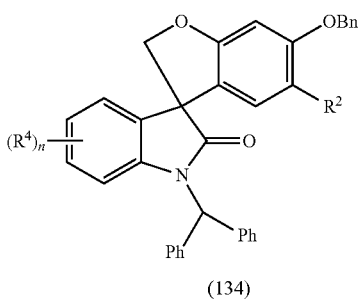

(134)

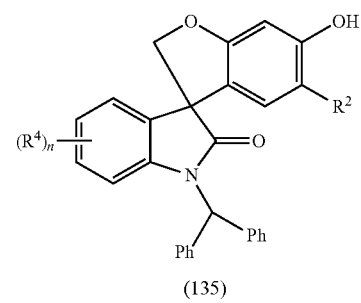

(135)

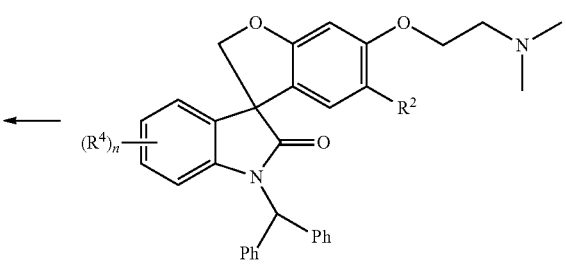

(137)         (136)

↓ XR¹ or TsOR¹

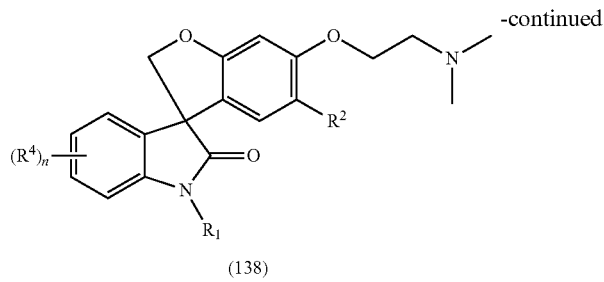

(138)

Compounds of formula (134) can be prepared according to methods known to one skilled in the art or by the methods disclosed herein or by the methods disclosed in PCT Published Patent Application WO 2006/110917.

As set forth above, the benzyl protecting on the compound of formula (134) is removed selectively by hydrogenation of the compound of formula (134) under one atm pressure of hydrogen with a catalyst such as, but is not limited to, palladium on carbon, in a solvent such as, but is not limited to, methanol, to provide compound of formula (135). The reaction of compound of formula (135) with N,N-dimethylethanolamine under Mitsunobu reaction conditions in the presence of a phosphine reagent such as, but not limited to, triphenylphosphine, and diethyl azadicarboxylate, in a solvent such as, but not limited to, tetrahydrofuran, provides the compound of formula (136), a compound of formula (I). The protecting diphenylmethyl group is removed at 60° C. under a high pressure of hydrogen, such as 60 psi, to form compound of formula (137). The formation of a compound of formula (138), a compound of formula (I), is achieved by alkylation of the compound of formula (137) with a halide reagent $XR^1$ (where X is chloro, bromo or iodo) or a tosylate reagent $TsOR^1$ in the presence of a base such as, but not limited to, sodium hydride, lithium hydroxide, and cesium carbonate, in a solvent such as, but not limited to, N,N-dimethylformamide, tetrahydrofuran, 2-butanone.

Compounds of formula (I) where $R^3$ is —O—$R^5$—N($R^7$)C(O)O$R^8$ or —O—$R^5$—N($R^7$)$R^8$ where each $R^5$, $R^7$ and $R^8$ are as described above in the Summary of the Invention, can be prepared in a similar manner as described below in REACTION SCHEME 10 where n, $R^1$, $R^2$ and $R^4$ are as described above in the Summary of the Invention, Ph is phenyl, Bn is benzyl and TIPS is tris(1-methylethyl)silyl:

REACTION SCHEME 10

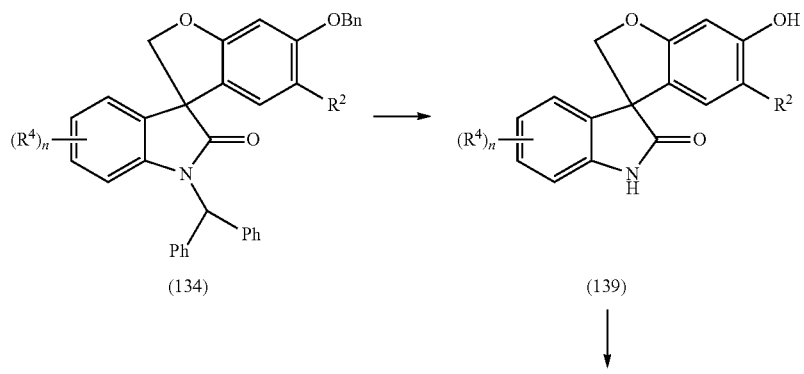

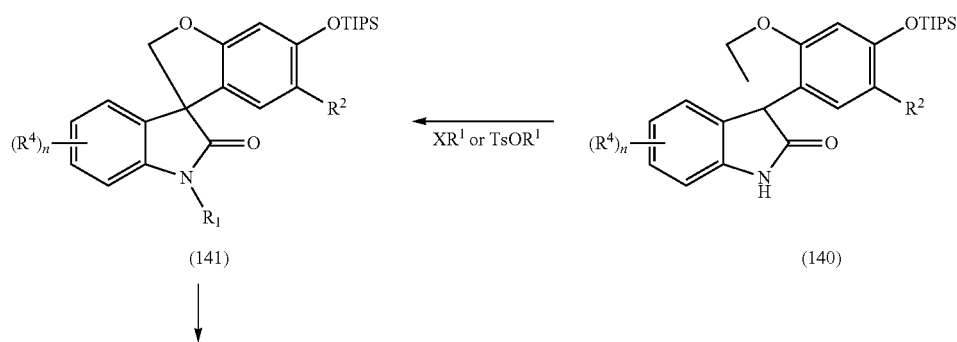

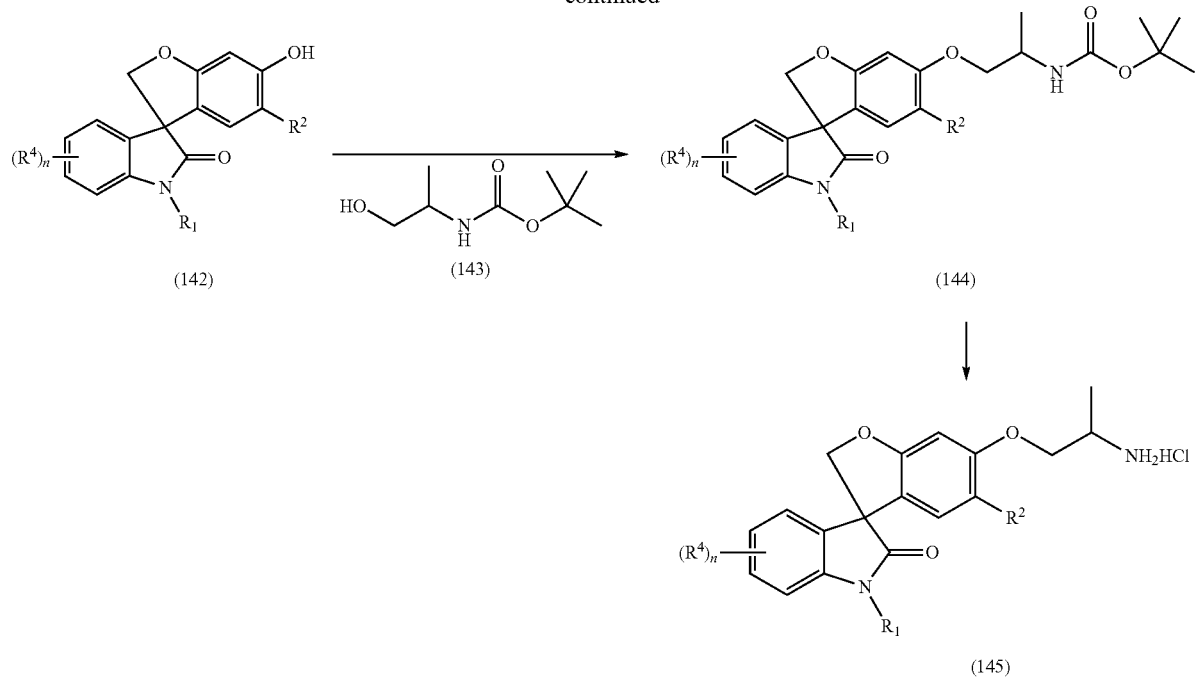

(142) (143) (144) (145)

Compounds of formula (134) can be prepared according to methods known to one skilled in the art or by the methods disclosed herein or by the methods disclosed in PCT Published Patent Application WO 2006/110917. Compounds of formula (143) are commercially available or can be prepared according to methods known to one skilled in the art.

As set forth above, the diphenyl methyl and benzyl protecting groups in the compounds of formula (134) is removed at 60° C. under a high pressure of hydrogen, such as 60 psi, to form a compound of formula (139) in a solvent such as, but not limited to, methanol. The compound of formula (139) is then protected selectively by TIPSCI to form a compound of formula (140). The formation of a compound of formula (140) is achieved by alkylation of the compound of formula (140) with a halide reagent $XR^1$ (where X is chloro, bromo or iodo) or a tosylate reagent $TsOR^1$ in the presence of a base such as, but not limited to, sodium hydride, and cesium carbonate, in a solvent such as, but not limited to, N,N-dimethylformamide, tetrahydrofuran, 2-butanone. The phenol compound of formula (142) can be obtained by deprotection of a compound of formula (141) in the presence of tetrabutylammonium fluoride. The reaction of compound of formula (142) with (D,L) tert-butyl 1-hydroxypropan-2-ylcarbamate (143) under Mitsunobu reaction conditions in the presence of a phosphine reagent such as, but not limited to, triphenylphosphine, and diethyl azadicarboxylate, in a solvent such as, but not limited to, tetrahydrofuran, provides the compound of formula (144), a compound of formula (I). The compound of formula (145), a compound of formula (I), can be synthesized by deprotection of the compound of formula (144) with an acid, such as, but not limited to, hydrochloride in dioxane, in a solvent such as, but not limited to, dichloromethane or methanol.

Compounds of formula (I) wherein $R^3$ is —O—$R^5$—C(O)O$R^7$ where $R^5$ and $R^7$ are as described above in the Summary of the Invention, preferably where $R^5$ is methylene and $R^7$ is hydrogen or alkyl, or wherein $R^2$ and $R^3$, together with the carbons to which they are attached, form a fused O-heterocyclyl ring substituted by =NO$R^7$ where $R^7$ is as described above in the Summary of the Invention, can be prepared in a similar manner as described below in REACTION SCHEME 11 where n, $R^1$ and $R^4$ are as described above in the Summary of the Invention:

REACTION SCHEME 11

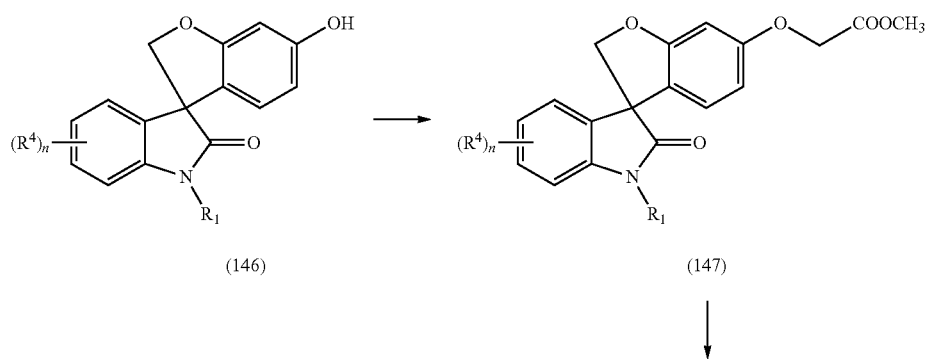

(146) (147)

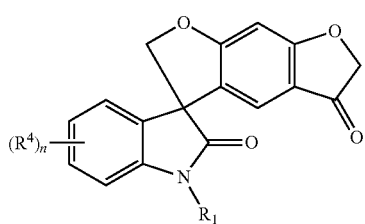 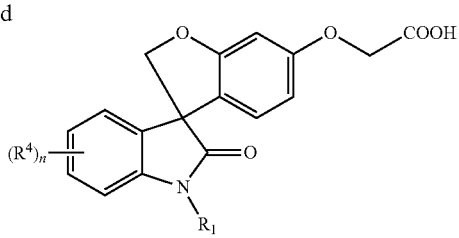

(149) (148)

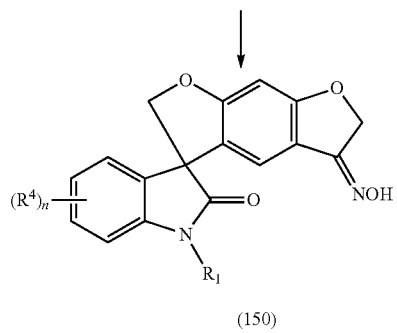

(150)

Compounds of formula (146) can be prepared according to methods known to one skilled in the art or by the methods disclosed herein or by the methods disclosed in PCT Published Patent Application WO 2006/110917.

As set forth above, a compound of formula (147), a compound of formula (I), is synthesized by alkylation of a compound of formula (146) with methyl bromoacetate in the presence of a base such as, but not limited to, potassium carbonate, in a solvent such as, but not limited to, 2-butanone. Hydrolysis of the compound of formula (147) in the presence of a base such as, but not limited to, lithium hydroxide affords the acid compound of formula (148), a compound of formula (I). The acid compound of formula (148) is converted to the corresponding acid chloride intermediate, by treatment with oxalyl chloride in the presence of catalytic amount of N,N-dimethylformamide in a solvent such as, but is not limited to, benzene. The acid chloride intermediate is treated with aluminum chloride to form the cyclized compound of formula (149) in a solvent such as, but not limited to, 2-butanone. Compound of formula (149) is then reacted with hydroxylamine hydrochloride in the presence of sodium acetate in a solvent such as, but is not limited to, a 1:1 mixture of methanol and tetrahydrofuran, to provide a compound of formula (150), a compound of formula (I).

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. It is understood that all polymorphs, amorphous forms, anhydrates, hydrates, solvates and salts of the compounds of the invention are intended to be within the scope of the invention. Furthermore, all compounds of the invention which contain an acid or an ester group can be converted to the corresponding ester or acid, respectively, by methods known to one skilled in the art or by methods described herein.

The following Preparations, which are directed to the preparation of intermediates or starting materials used in the preparation of the compounds of the invention, the following Examples, which are directed to the preparation of the compounds of the invention, and the following Biological Examples are provided as a guide to assist in the practice of the invention, and are not intended as a limitation on the scope of the invention.

Preparation 1

Synthesis of 3-[4-(benzyloxy)-2-hydroxyphenyl]-1-(diphenylmethyl)-1,3-dihydro-2H-indol-2-one A. Synthesis of 3-[4-(benzyloxy)-2-hydroxyphenyl]-1-(diphenylmethyl)-3-hydroxy-1,3-dihydro-2H-indol-2-one To a stirred solution of 3-(benzyloxy)phenol (8.7 g, 43.5 mmol) in tetrahydrofuran (100 mL) was added iso-propylmagnesium chloride (22.7 mL, 2 M tetrahydrofuran solution, 45.4 mmol) slowly at 0° C. The mixture was allowed to stir at 0° C. for 30 min, and concentrated in vacuo to dryness. Dichloromethane (100 mL) was added, followed by the addition of a solution of 1-(diphenylmethyl)-1H-indole-2,3-dione (12.4 g, 39.5 mmol) in dichloromethane (50 mL) at 0° C. The mixture was stirred at ambient temperature for 16 h, and quenched with saturated ammonium chloride solution. The organic layer was washed with water, dried over sodium sulfate and filtered. The filtrate was concentrated in vacuo to dryness. The obtained solid was recrystallized from ethyl acetate/hexanes to afford 3-[4-(benzyloxy)-2-hydroxyphenyl]-1-(diphenylmethyl)-3-hydroxy-1,3-dihydro-2H-indol-2-one (19.60 g, 97%) as a colorless solid: $^1$H NMR (300 MHz, CDCl$_3$) δ 7.49-7.43 (m, 1H), 7.42-7.25 (m, 13H), 7.23-7.17 (m, 2H), 7.12-7.04 (m, 2H), 6.91 (s, 1H), 6.72-6.62 (m, 2H), 6.51-6.44 (m, 1H), 6.39 (dd, J=8.6, 2.4 Hz, 1H), 4.99 (s, 2H); MS (ES+) m/z 536.3 (M+23).

B. Synthesis of 3-[4-(benzyloxy)-2-hydroxyphenyl]-1-(diphenylmethyl)-1,3-dihydro-2H-indol-2-one A mixture of 3-[4-(benzyloxy)-2-hydroxyphenyl]-1-(diphenylmethyl)-3-hydroxy-1,3-dihydro-2H-indol-2-one (10.0 g, 19.5 mmol), triethylsilane (15.6 mL, 97.5 mmol) and trifluoroacetic acid (15.0 mL, 195 mmol) was mixed and stirred at 0° C. for 20 min. The mixture was concentrated under vacuum. The residue was triturated with diethyl ether to afford 3-[4-(benzyloxy)-2-hydroxyphenyl]-1-(diphenylmethyl)-1,3-dihydro-2H-indol-2-one (7.40 g, 76%) as a colorless solid: $^1$H NMR (300 MHz, CDCl$_3$) δ 7.44-7.25 (m, 14H), 7.23-7.17 (m 2H), 7.11-7.02 (m, 2H), 6.95 (s, 1H), 6.81 (d, J=8.6 Hz, 1H), 6.68 (d, J=2.5 Hz, 1H), 6.55-6.49 (m, 1H), 6.46 (dd, J=8.6, 2.6 Hz, 1H), 5.09 (s, 1H), 4.99 (s, 2H); MS (ES+) m/z 498.3 (M+1).

Preparation 2

Synthesis of 3-(4-bromo-2-hydroxyphenyl)-1-(diphenylmethyl)-1,3-dihydro-2H-indol-2-one A. Synthesis of 3-(4-bromo-2-hydroxyphenyl)-1-(diphenylmethyl)-3-hydroxy-1,3-dihydro-2H-indol-2-one To a stirred solution of 3-bromophenol (11.9 g, 69.2 mmol) in dichloromethane (160.0 mL) at 0° C. was added isopropylmagnesium chloride (2.0 M in tetrahydrofuran, 38.0 mL, 76.1 mmol). The solution was stirred at 0° C. for 30 min, then 1-benzhydrylindoline-2,3-dione (10.0 g, 34.6 mmol) was added. The reaction was stirred at ambient temperature for 16 h, then concentrated in vacuo to dryness. The residue obtained was dissolved in ethyl acetate (400.0 mL) and washed with saturated ammonium chloride solution (3×100.0 mL). The organic phase was dried over magnesium sulfate, filtered and concentrated in vacuo to dryness. Purification by flash chromatography with 30% ethyl acetate in hexanes afforded 3-(4-bromo-2-hydroxyphenyl)-1-(diphenylmethyl)-3-hydroxy-1,3-dihydro-2H-indol-2-one (11.7 g, 70%) as a beige solid: $^1$H NMR (300 MHz, CDCl$_3$) δ 9.09 (br s, 1H), 7.47-7.16 (m, 11H), 7.12-7.00 (m, 3H), 6.92-6.84 (m, 2H), 6.72-6.66 (m, 1H), 6.51-6.45 (m, 1H), 4.57 (br s, 1H); MS (ES+) m/z 484.2 (M+1), 486.2 (M+1).

B. Synthesis of 3-(4-bromo-2-hydroxyphenyl)-1-(diphenylmethyl)-1,3-dihydro-2H-indol-2-one To an ice cold stirred solution of 3-(4-bromo-2-hydroxyphenyl)-1-(diphenylmethyl)-3-hydroxy-1,3-dihydro-2H-indol-2-one (13.1 g, 27.1 mmol) in triethylsilane (25.0 mL) was added trifluoroacetic acid (25.0 mL). The solution was stirred at ambient temperature for 64 h, then concentrated in vacuo to dryness. Recrystallization from diethyl ether (25.0 mL) in a Branson ultrasonic bench top water bath afforded 3-(4-bromo-2-hydroxyphenyl)-1-(diphenylmethyl)-1,3-dihydro-2H-indol-2-one (10.1 g, 79%) as a colorless solid: $^1$H NMR (300 MHz, CDCl$_3$) δ 9.17 (s, 1H), 7.40-7.03 (m, 13H), 6.99-6.92 (m, 2H), 6.79-6.74 (m, 2H), 6.58-6.50 (m, 1H), 5.10 (s, 1H); MS (ES−) m/z 468.2 (M−1), 470.2 (M−1).

Preparation 3

Synthesis of 6-(benzyloxy)-1'-(diphenylmethyl)spiro[1-benzofuran-3,3'-indol]-2'(1'H)-one To a stirred solution of 3-[4-(benzyloxy)-2-hydroxyphenyl]-1-(diphenylmethyl)-1,3-dihydro-2H-indol-2-one (7.4 g, 14.8 mmol), chloroiodomethane (2.7 mL, 37.0 mmol) in anhydrous tetrahydrofuran (200 mL) was added cesium carbonate (15.4 g, 47.4 mmol) under argon. The mixture was stirred at ambient temperature for 16 h, then filtered through a pad of celite. The filtrate was concentrated under vacuum. The residue was purified by column chromatography (ethyl acetate/hexanes, 1/5) followed by the treatment with diethyl ether/hexanes to afford 6-(benzyloxy)-1'-(diphenylmethyl) spiro[1-benzofuran-3,3'-indol]-2'(1'H)-one (4.1 g, 55%) as a colorless solid: $^1$H NMR (300 MHz, CDCl$_3$) δ 7.42-7.25 (m, 15H), 7.16-7.09 (m, 1H), 7.07-6.90 (m, 3H), 6.62-6.38 (m, 4H), 5.03-4.90 (m, 3H), 4.73 (d, J=9.0 Hz, 1H); MS (ES+) m/z 510.1 (M+1).

Preparation 4

Synthesis of 6-hydroxyspiro[1-benzofuran-3,3'-indol]-2'(1'H)-one

A suspension of 6-(benzyloxy)-1'-(diphenylmethyl)spiro[1-benzofuran-3,3'-indol]-2'(1'H)-one (0.60 g, 1.2 mmol) in methanol (20 mL) was degassed by bubbling through nitrogen for 1 h before palladium hydroxide on carbon (20%, 0.08 g, 0.12 mmol) was added. The mixture was stirred under 120 psi of hydrogen at 60° C. for 16 h. The mixture was filtered through a pad of celite, and the filtrate was concentrated in vacuo. The obtained residue was recrystallized with ethyl acetate and hexane to afford 6-hydroxy-2H-spiro[benzofuran-3,3'-indolin]-2'-one (0.25 g, 83%) as a colorless solid: $^1$H NMR (300 MHz, DMSO-d$_6$) δ 10.86-9.35 (br, 2H), 7.19 (td, J=7.6, 1.2 Hz, 1H), 7.03 (d, J=7.3 Hz, 1H), 6.96-6.84 (m, 2H), 6.42 (d, J=8.2 Hz, 1H), 6.29 (d, J=2.1 Hz, 1H), 6.17 (dd, J=8.2, 2.1 Hz, 1H), 4.72 (d, J=9.2 Hz, 1H), 4.59 (d, J=9.2 Hz, 1H); MS (ES+) m/z 254.1 (M+1).

Preparation 5

Synthesis of 1'-(diphenylmethyl)-6-hydroxyspiro[1-benzofuran-3,3'-indol]-2'(1'H)-one A suspension of 6-(benzyloxy)-1'-(diphenylmethyl)spiro[1-benzofuran-3,3'-indol]-2'(1'H)-one (1.00 g, 2.0 mmol) in methanol/ethyl acetate (15/25 mL) was degassed by bubbling through nitrogen for 1 h before palladium on carbon (5%, 0.42 g, 0.2 mmol) was added. The mixture was stirred under hydrogen at ambient temperature for 16 h. The mixture was filtered through a pad of celite, and the filtrate was concentrated in vacuo. The obtained residue was recrystallized from ethyl acetate and hexane to afford 1'-(diphenylmethyl)-6-hydroxyspiro[1-benzofuran-3,3'-indol]-2'(1'H)-one (0.78 g, 95%) as a colorless solid: $^1$H NMR (300 MHz, CDCl$_3$) δ 7.42-7.25 (m, 10H), 7.16-7.10 (m, 1H), 7.07-6.92 (m, 3H), 6.54-6.48 (m, 1H), 6.44 (d, J=8.2 Hz, 1H), 6.33 (d, J=2.2 Hz, 1H), 6.20 (dd, J=8.2, 2.2 Hz, 1H), 5.65 (s, 1H), 4.99 (d, J=9.0 Hz, 1H), 4.71 (d, J=9.0 Hz, 1H); MS (ES+) m/z 420.1 (M+1).

Preparation 6

Synthesis of 1'-(4-bromobenzyl)spiro[furo[2,3-f][1,3]benzodioxole-7,3'-indol]-2'(1'H)-one A mixture of spiro[furo[2,3-f][1,3]benzodioxole-7,3'-indol]-2'(1'H)-one (1.05 g, 3.73 mmol), 4-bromobenzyl bromide (1.21 g, 4.84 mmol) and cesium carbonate (1.84 g, 5.65 mmol) in 2-butanone (25 mL) was stirred at ambient temperature for 16 h. The mixture was diluted with ethyl acetate and filtered through Celite. The filtrate was concentrated under reduced pressure and the residue was purified by flash column chromatography and eluted with hexanes/ethyl acetate (9:1, increased to 1:1) to afford 1'-(4-bromobenzyl)spiro[furo[2,3-f][1,3]benzodioxole-7,3'-indol]-2'(1'H)-one (1.42 g, 84%) as a colorless solid: mp 148-150° C. (hexanes); $^1$H NMR (300 MHz, CDCl$_3$) δ 7.48 (d, J=8.4 Hz, 2H), 7.25-7.17 (m, 4H), 7.05 (dd, J=7.5, 7.5 Hz, 1H), 6.77 (d, J=7.8 Hz, 1H), 6.53 (s, 1H), 6.12 (s, 1H), 5.89 (s, 1H), 5.88 (s, 1H), 5.02 (d, J=15.6 Hz, 1H), 4.97 (d, J=9.0 Hz, 1H), 4.78 (d, J=15.6 Hz, 1H), 4.70 (d, J=9.0 Hz, 1H); $^{13}$C NMR (75 MHz, CDCl$_3$) δ 177.8, 156.1, 149.1, 142.5, 141.9, 134.9, 132.3, 132.2, 129.3, 129.1, 124.2, 123.8, 122.0, 119.4, 109.3, 103.1, 101.7, 93.8, 80.6, 58.4, 43.7; MS (ES+) m/z 452.0 (M+1), 450.0 (M+1).

Preparation 7

Synthesis of 3-[(2'-oxo-5,6-dihydrospiro[benzo[1,2-b:5,4-b']difuran-3,3'-indol]-1'(2'H)-yl)methyl]benzonitrile To a solution of 5,6-dihydrospiro[benzo[1,2-b:5,4-b']difuran-3,3'-indol]-2'(1'H)-one (0.97 g, 3.46 mmol) in 2-butanone (25 mL) were added cesium carbonate (3.39 g, 10.39 mmol) and α-bromo-m-tolunitrile (0.85 g, 4.33 mmol). The mixture was heated to reflux for 2 h, cooled to ambient temperature, and filtered. The solid was washed with ethyl acetate. The filtrate was concentrated in vacuo, the residue was purified by column chromatography with ethyl acetate-hexanes (1:5-1:1), followed by recrystallization from ethyl acetate and ether to afford 3-[(2'-oxo-5,6-dihydrospiro[benzo[1,2-b:5,4-b']difuran-3,3'-indol]-1'(2'H)-yl)methyl]benzonitrile (1.26 g, 92%) as a colorless solid: mp 187-193° C.; $^1$H NMR (300 MHz, CDCl$_3$) δ 7.61-7.58 (m, 3H), 7.47-7.44 (m, 1H), 7.25-7.19 (m, 2H), 7.07-7.03 (m, 1H), 6.73-6.71 (m, 1H), 6.43-6.41 (m, 2H), 5.11-4.70 (m, 4H), 4.53 (d, J=9.0 Hz, 2H), 3.09-2.91 (m, 2H); $^{13}$C NMR (75 MHz, CDCl$_3$) δ 178.1, 162.0, 161.4, 141.5, 137.5, 132.6, 131.9, 131.6, 130.7, 129.9, 128.9, 124.3, 123.9, 120.2, 119.9, 118.7, 118.4, 113.1, 108.8, 93.4, 80.5, 72.5, 57.7, 43.4, 29.0; MS (ES+) m/z 394.8 (M+1).

Preparation 8

Synthesis of (2'-oxospiro[furo[2,3-f][1,3]benzodioxole-7,3'-indol]-1'(2'H)-yl)acetonitrile Following the procedure as described in PREPARATION 7 and making non-critical variations using chloroacetonitrile to replace α-bromo-m-tolunitrile, and spiro[furo[2,3-f][1,3] benzodioxole-7,3'-indol]-2'(1'H)-one to replace 5,6-dihydrospiro[benzo[1,2-b:5,4-b']difuran-3,3'-indol]-2"(1'H)-one, (2'-oxospiro[furo[2,3-f][1,3]benzodioxole-7,3'-indol]-1'(2'H)-yl)acetonitrile was obtained (61%) as a colorless solid: mp 170-172° C.; $^1$H NMR (300 MHz, DMSO-d$_6$) δ 7.38 (dt, J=7.7, 1.2 Hz, 1H), 7.26 (d, J=7.7 Hz, 1H), 7.20 (d, J=7.3 Hz, 1H), 7.11 (dt, J=7.7, 1.1 Hz, 1H), 6.66 (s, 1H), 6.21 (s, 1H), 5.89 (d, J=1.5 Hz, 2H), 4.94 (ABq, 2H), 4.73 (ABq, 2H); $^{13}$C NMR (75 MHz, DMSO-d$_6$) δ 176.8, 155.8, 148.9, 142.2, 141.0, 131.9, 129.4, 124.3, 124.3, 119.8, 116.0, 109.7, 103.5, 101.9, 93.8, 80.1, 57.8, 28.8; MS (ES+) m/z 321.3 (M+1).

Preparation 9

Synthesis of 4-((2'-oxo-5,6-dihydro-2H-spiro[benzofuro[6,5-b]furan-3,3'-indoline]-1'-yl)methyl)benzonitrile Following the procedure as described in PREPARATION 7 and making non-critical variations using 4-(bromomethyl)benzonitrile to replace α-bromo-m-tolunitrile, 4-((2'-oxo-5,6-dihydro-2H-spiro[benzofuro[6,5-b]furan-3,3'-indoline]-1'-yl)methyl)benzonitrile was obtained (88%) as a colorless solid: mp 69-71° C.; $^1$H NMR (300 MHz, CDCl$_3$) δ 7.73-7.56 (m, 2H), 7.50-7.40 (m, 2H), 7.22-7.15 (m, 2H), 7.10-7.00 (m, 1H), 6.75-6.66 (m, 1H), 6.47-6.38 (m, 2H), 4.99 (ABq, 2H), 4.83 (ABq, 2H), 4.54 (t, J=8.6 Hz, 2H), 3.06-2.92 (m, 2H); MS (ES+) m/z 395.0 (M+1).

Preparation 10

Synthesis of 3-(2'-oxospiro[furo[2,3-f][1,3]benzodioxole-7,3'-indol]-1'(2'H)-yl)propanenitrile Following the procedure described in PREPARATION 7 and making non-critical variations using 3-bromopropionitrile to replace α-bromo-m-tolunitrile, and spiro[furo[2,3-f][1,3]benzodioxole-7,3'-indol]-2'(1'H)-one to replace 5,6-dihydrospiro[benzo[1,2-b:5,4-b']difuran-3,3'-indol]-2"(1'H)-one, 3-(2'-oxospiro[furo[2,3-f][1,3]benzodioxole-7,3'-indol]-1'(2'H)-yl)propanenitrile was obtained (86%) as a colorless solid: mp 200-202° C.; $^1$H NMR (300 MHz, DMSO-d$_6$) δ 7.32 (ddd, J=7.6, 7.4, 1.2 Hz, 1H), 7.24 (d, J=7.6 Hz, 1H), 7.15 (d, J=6.7 Hz, 1H), 7.04 (ddd, J=7.4, 7.4, 1.0 Hz, 1H), 6.66 (s, 1H), 6.24 (s, 1H), 5.89 (d, J=2.2 Hz, 2H), 4.69 (ABq, J=9.3 Hz, 2H), 4.10-3.88 (m, 2H), 2.95 (t, J=6.5 Hz, 2H); $^{13}$C NMR (75 MHz, DMSO-d$_6$) δ 177.1, 155.8, 148.8, 142.2, 141.9, 132.3, 129.3, 124.1, 123.7, 120.1, 119.1, 109.8, 103.6, 101.9, 93.7, 80.3, 57.9, 35.9, 16.2; MS (ES+) m/z 335.1 (M+1).

Preparation 11

Synthesis of tert-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate Following the procedure as described in PREPARATION 7 and making non-critical variations using (S)-tert-butyl 2-(tosyloxymethyl)pyrrolidine-1-carboxylate (Fuji, K., et al., *J. Am. Chem. Soc.* (1989), 111(20):7921-5) to replace α-bromo-m-tolunitrile, tert-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate was obtained (80%) as a colorless solid: $^1$H NMR (300 MHz, CDCl$_3$) (diastereomers) δ 7.37-7.25 (m, 2H), 7.20-7.00 (m, 2H), 6.54-6.41 (m, 2H), 4.96-4.88 (m, 1H), 4.70-4.64 (m, 1H), 4.534 (t, J=8.6 Hz, 1H), 4.527 (t, J=8.6 Hz, 1H), 4.31-4.19 (m, 1H), 3.99-3.85 (m, 1H), 3.80-3.67 (m, 1H), 3.49-3.22 (m, 2H), 3.05-2.91 (m, 2H), 2.10-1.77 (m, 4H), 1.48 (s, 4.5H), 1.42 (s, 4.5H); MS (ES+) m/z 485.1 (M+23).

Preparation 12

Synthesis of 1'-[(2S)-pyrrolidin-2-ylmethyl]-5,6-dihydrospiro[benzo[1,2-b:5,4-b']difuran-3,3'-indol]-2'(1'H)-one A solution of tert-butyl (2S)-2-[(2'-oxo-5,6-dihydrospiro[benzo[1,2-b:5,4-b']difuran-3,3'-indol]-1'(2'H)-yl)methyl]pyrrolidine-1-carboxylate (0.74 g, 1.60 mmol) and trifluoroacetic acid (1.6 mL) in dichloromethane (8 mL) was stirred at ambient temperature for 80 h. The reaction was made basic with 1 M sodium hydroxide (30 mL) and was extracted with dichloromethane (3×25 mL). The combined organic solution was dried over sodium sulfate, filtered and concentrated under reduced pressure to afford 1'-[(2S)-pyrrolidin-2-ylmethyl]-5,6-dihydrospiro[benzo[1,2-b:5,4-b']difuran-3,3'-indol]-2'(1'H)-one (0.51 g, 89%) as a pale yellow solid: mp 83-86° C. (hexanes); $^1$H NMR (300 MHz, CDCl$_3$) (diastereomers) δ 7.29 (dd, J=7.8, 7.5 Hz, 1H), 7.16 (d, J=7.5 Hz, 1H), 7.07-6.99 (m, 2H), 6.52, 6.46 (s, 1H), 6.40 (s, 1H), 4.95, 4.91 (d, J=9.0 Hz, 1H), 4.66 (d, J=9.0 Hz, 1H), 4.53 (t, J=8.7 Hz, 2H), 3.91-3.71 (m, 2H), 3.69-3.60 (m, 1H), 3.14-2.90 (m, 5H), 1.98-1.70 (m, 3H), 1.66-1.51 (m, 1H); MS (ES+) m/z 363.1 (M+1).

Preparation 13

Synthesis of 1'-[3-(benzyloxy)benzyl]-5,6-dihydrospiro[benzo[1,2-b:5,4-b']difuran-3,3'-indol]-2'(1'H)-one To a stirred solution of 5,6-dihydro-2H-spiro[benzofuro[6,5-b]furan-3,3'-indolin]-2'-one (1.0 g, 3.6 mmol) in dry N,N-dimethylformamide (18 mL) was added sodium hydride (60% in mineral oil, 0.17 g, 4.3 mmol) at ambient temperature. The mixture was stirred at ambient temperature for 1 h, cooled in an ice/water bath, and 1-(benzyloxy)-3-(bromomethyl)benzene (1.4 g, 5.0 mmol) in dry N,N-dimethylformamide (2 mL) was added dropwise. The mixture was stirred at ambient temperature for 16 h. Water (200 mL) and ethyl acetate (200 mL) were added to the mixture. The organic solution was separated and the aqueous layer was extracted with ethyl acetate (2×100 mL). The combined organic solution was washed with brine (150 mL), dried over anhydrous magnesium sulfate, filtered, and concentrated in vacuo. The residue was purified by column chromatography (hexanes/ethyl acetate 3:1) to afford 1'-[3-(benzyloxy)benzyl]-5,6-dihydrospiro[benzo[1,2-b:5,4-b']difuran-3,3'-indol]-2'(1'H)-one (1.4 g, 82%) as a colorless solid: mp 66-68° C.; $^1$H NMR (300 MHz, CDCl$_3$) δ 7.43-7.14 (m, 8H), 7.06-6.99 (m, 1H), 6.97-6.87 (m, 3H), 6.81-6.75 (m, 1H), 6.48 (s, 1H), 6.43 (s, 1H), 5.10-5.00 (m, 3H), 4.85-4.75 (m, 1H), 4.84 (ABq, 2H), 4.56-4.47 (m, 2H), 2.98-2.88 (m, 2H); $^{13}$C NMR (75 MHz, CDCl$_3$) δ 177.9, 161.8, 161.3, 159.2, 142.1, 137.4, 136.6, 132.7, 129.9, 128.7, 128.6, 128.0, 127.5, 123.8, 123.4, 120.2, 119.9 (2C), 118.8, 114.0, 113.9, 109.3, 93.2, 80.5, 72.3, 70.0, 57.7, 44.0, 29.0; MS (ES+) m/z 476.1 (M+1).

Preparation 14

Synthesis of 1'-(3-hydroxybenzyl)-5,6-dihydrospiro[benzo[1,2-b:5,4-b']difuran-3,3'-indol]-2'(1H)-one A mixture of 1'-[3-(benzyloxy)benzyl]-5,6-dihydrospiro[benzo[1,2-b:5,4-b']difuran-3,3'-indol]-2'(1'H)-one (1.30 g, 2.7 mmol) and 10% wt. palladium on carbon (0.25 g) in dry methanol (14 mL) was hydrogenated at ambient temperature under a balloon pressure for 16 h. The mixture was filtered through a pad of celite and concentrated in vacuo to dryness. The residue was subjected to column chromatography (hexanes/ethyl acetate from 2:1 to 1:1) to afford 1'-(3-hydroxybenzyl)-5,6-dihydrospiro[benzo[1,2-b:5,4-b']difuran-3,3'-indol]-2'(1'H)-one (0.97 g, 93%) as a colorless solid: mp 225-227° C.; $^1$H NMR (300 MHz, CDCl$_3$) δ 9.48 (s, 1H), 7.30-7.22 (m, 1H), 7.20-7.11 (m, 2H), 7.06-6.94 (m, 2H), 6.81-6.76 (m, 1H), 6.72-6.69 (m, 1H), 6.68-6.63 (m, 1H), 6.46 (s, 1H), 6.43 (s, 1H), 4.85 (ABq, J=35.6, 15.8 Hz, 2H), 4.79 (ABq, 2H), 4.55-4.46 (m, 2H), 3.02-2.92 (m, 2H); $^{13}$C NMR (75 MHz, CDCl$_3$) δ 177.0, 161.1, 160.6, 157.6, 142.2, 137.6, 132.0, 129.7, 128.6, 123.6, 123.0, 120.4, 119.9, 118.9, 117.7, 114.4, 113.6, 109.4, 92.5, 79.8, 72.1, 56.9, 42.9, 28.3; MS (ES+) m/z 386.0 (M+1).

Preparation 15

Synthesis of 1'-[4-(methylsulfanyl)benzyl]-5,6-dihydrospiro[benzo[1,2-b:5,4-b']difuran-3,3'-indol]-2'(1H)-one Following the procedure as described in PREPARATION 7 and making non-critical variations using (4-(bromomethyl)phenyl)(methyl)sulfane to replace α-bromo-m-tolunitrile, 1'-[4-(methylsulfanyl)benzyl]-5,6-dihydrospiro[benzo[1,2-b:5,4-b']difuran-3,3'-indol]-2'(1'H)-one was obtained (61%) as a colorless solid: MS (ES+) m/z: 416.2 (M+1).

Preparation 16

Synthesis of 6-bromo-1'-(diphenylmethyl)spiro[1-benzofuran-3,3'-indol]-2'(1'H)-one To a stirred solution of 3-(4-bromo-2-hydroxyphenyl)-1-(diphenylmethyl)-1,3-dihydro-2H-indol-2-one (10.1 g, 22.6 mmol) and cesium carbonate (22.1 g, 67.8 mmol) in tetrahydrofuran (100.0 mL) was added chloroiodomethane (5.88 g, 33.9 mmol). The solution was stirred at ambient temperature for 3 h, then filtered through a pad of silica gel followed by tetrahydrofuran rinses (500.0 mL). The filtrate was concentrated in vacuo to dryness, and recrystallized from diethyl ether (20.0 mL) in a Branson ultrasonic bench top water bath to afford 6-bromo-1-(diphenylmethyl)spiro[1-benzofuran-3,3'-indol]-2'(1'H)-one (7.3 g, 67%) as a colorless solid: $^1$H NMR (300 MHz, CDCl$_3$) δ 7.44-7.25 (m, 10H), 7.15-7.09 (m, 2H), 7.07-6.90 (m, 4H), 6.56-6.49 (m, 2H), 5.03 (d, J=9.1 Hz, 1H), 4.76 (d, J=9.1 Hz, 1H); MS (ES+) m/z 482.1 (M+1), 484.0 (M+1).

Preparation 17

Synthesis of 6-bromospiro[1-benzofuran-3,3'-indol]-2'(1'H)-one

A stirred solution of 6-bromo-1'-(diphenylmethyl)spiro[1-benzofuran-3,3'-indol]-2'(1H)-one (2.5 g, 5.2 mmol), triethylsilane (5.0 mL) and trifluoroacetic acid (15.0 mL) was refluxed for 14 h. The solution was concentrated in vacuo and precipitated from hexanes to afford 6-bromospiro[1-benzofuran-3,3'-indol]-2'(1'H)-one (1.47 g, 89%) as a colorless solid: MS (ES+) m/z 316.1 (M+1), 318.1 (M+1).

Preparation 18

Synthesis of 6-bromo-1-[(2R)-tetrahydrofuran-2-ylmethyl]spiro[1-benzofuran-3,3'-indol]-2'(1'H)-one To a stirred solution of 6-bromospiro[1-benzofuran-3,3'-indol]-2'(1'H)-one (1.3 g, 4.3 mmol) in 2-butanone (40.0 mL) was added cesium carbonate (4.2 g, 12.9 mmol) and (R)-(tetrahydrofuran-2-yl)methyl 4-methylbenzenesulfonate (1.4 g, 5.4 mmol). The reaction was refluxed for 16 h, filtered and concentrated in vacuo to dryness. The residue was purified by flash chromatography with 25% ethyl acetate in hexanes to afford 6-bromo-1'-[(2R)-tetrahydrofuran-2-ylmethyl]spiro[1-benzofuran-3,3'-indol]-2'(1'H)-one (1.75 g, 100%) as a colorless solid: MS (ES+) m/z 400.0 (M+1), 402.0 (M+1).

Preparation 19

Synthesis of 6-amino-1'-[(2R)-tetrahydrofuran-2-ylmethyl]spiro[1-benzofuran-3,3'-indol]-2'(1'H)-one To a stirred solution of 6-bromo-1'-[(2R)-tetrahydrofuran-2-ylmethyl]spiro[1-benzofuran-3,3'-indol]-2'(1H)-one (1.65 g, 4.1 mmol), benzophenone imine (0.90 g, 4.92 mmol), tris(dibenzylideneacetone)dipalladium(0) (0.46 g, 0.51 mmol), 2,2'-bis(diphenylphosphino)-1,1'-binaphtyl (0.96 g, 1.6 mmol) in toluene (50.0 mL) was added sodium tert-butoxide (0.55 g, 5.8 mmol). The mixture was stirred at reflux for 2 h, cooled to ambient temperature, diluted with ethyl acetate (75 mL), filtered through celite and concentrated in vacuo to dryness. The residue was dissolved in tetrahydrofuran (150 mL) and 3 M hydrochloric acid (15 mL). The solution was diluted with ethyl acetate (250 mL), and adjusted to basic with 5 M sodium hydroxide. The aqueous phase was further extracted with ethyl acetate (2×100 mL). The combined organic solution was dried over magnesium sulfate, filtered and concentrated in vacuo to dryness. The residue was purified by flash chromatography and eluted with ethyl acetate in hexanes (15% to 50% gradient) to afford 6-amino-1-[(2R)-tetrahydrofuran-2-ylmethyl]spiro[1-benzofuran-3,3'-indol]-2'(1'H)-one (0.84 g, 61%) as a colorless solid: mp 71-74° C.; $^1$H NMR (300 MHz, CDCl$_3$, mixture of diastereomers) δ 7.29-7.22 (m, 1H), 7.14-6.95 (m, 3H), 6.46 (d, J=8.1 Hz, 1H), 6.26 (d, J=2.0 Hz, 1H), 6.10 (dd, J=8.1, 2.0 Hz, 1H), 4.75 (ABq, J=75.6, 8.9 Hz, 2H), 4.31-4.19 (m, 1H), 3.99-3.61 (m, 6H), 2.08-1.80 (m, 3H), 1.77-1.61 (m, 1H); $^{13}$C NMR (75 MHz, CDCl$_3$, mixture of diastereomers) δ 178.3 (2), 162.1, 148.4, 142.9 (2), 132.7 (2), 128.6 (2), 123.7, 123.6 (2), 123.2 (2), 118.8 (2), 109.4 (2), 108.4, 97.2, 80.3 (2), 68.2 (2), 57.6 (2), 44.5 (2), 29.1 (2), 25.6 (2); MS (ES+) m/z 337.0 (M+1).

Preparation 20

Synthesis of 6-hydroxy-1'[(2R)-tetrahydrofuran-2-ylmethyl]spiro[1-benzofuran-3,3'-indol]-2'(1'H)-one To a solution of 1'-[(2R)-tetrahydrofuran-2-ylmethyl]-6-{[tris(1-methylethyl)silyl]oxy}spiro[1-benzofuran-3,3'-indol]-2'(1H)-one (1.69 g, 3.43 mmol) in anhydrous tetrahydrofuran (15 mL) under nitrogen was added tetrabutylammonium fluoride (1 M solution in tetrahydrofuran, 10 mL, 10 mmol), and the mixture was stirred at ambient temperature for 16 h. The reaction mixture was concentrated, and the residue was re-dissolved in ethyl acetate (25 mL), washed with water (2×20 mL) and brine (20 mL), dried over sodium sulfate, filtered, and concentrated. The residue was purified by column chromatography with 40% ethyl acetate in hexanes to afford 6-hydroxy-1'-[(2R)-tetrahydrofuran-2-ylmethyl]spiro[1-benzofuran-3,3'-indol]-2'(1'H)-one (1.00 g, 86%) as a colorless solid: mp 72-74° C.; $^1$H NMR (300 MHz, CDCl$_3$) δ 7.29 (ddd, J=7.5, 7.5, 1.2 Hz, 1H), 7.18-7.01 (m, 3H), 6.80-6.67 (br, 1H), 6.44 (d, J=8.4 Hz, 1H), 6.24 (d, J=2.1 Hz, 1H), 6.17-6.09 (m, 1H), 4.96-4.90 (m, 1H), 4.69-4.63 (m, 1H), 4.36-4.24 (m, 1H), 4.00-3.71 (m, 4H), 2.12-1.61 (m, 4H); MS (ES+) m/z 338.1 (M+1).

Preparation 21

Synthesis of 1'-[(2R)-tetrahydrofuran-2-ylmethyl]spiro[benzo[1,2-b:5,4-b']difuran-3,3'-indole]-2',5(1'H,6H)-dione To a solution of ({2'-oxo-1'-[(2R)-tetrahydrofuran-2-ylmethyl]-1',2'-dihydrospiro[1-benzofuran-3,3'-indol]-6-yl}oxy)acetic acid (0.42 g, 1.06 mmol) in benzene were added oxalyl chloride (0.28 mL, 3.18 mmol) and a drop of N,N-dimethyl formamide. The reaction mixture was refluxed for 16 h. The mixture was evaporated to dryness and dried over high vacuum pump. The residue was re-dissolved in anhydrous dichloromethane (30 mL), then aluminum trichloride (0.21 g, 1.59 mmol) was added. The reaction mixture was stirred at ambient temperature for 16 h, and refluxed for 2 h. The reaction was quenched by saturated ammonium chloride solution, then extracted with dichloromethane (2×50 mL). The combined organic solution was dried over sodium sulfate, filtered, and concentrated. The residue was purified by flash chromatography with 50% ethyl acetate in hexanes to give 1-[(2R)-tetrahydrofuran-2-ylmethyl]spiro[benzo[1,2-b:5,4-b']difuran-3,3'-indole]-2',5(1'H,6H)-dione (0.28 g, 69%) as a colorless solid: mp 142-144° C.; $^1$H NMR (300 MHz, CDCl$_3$) δ 7.36-7.29 (m, 1H), 7.16-7.00 (m, 4H), 6.64-6.60 (m, 1H), 5.08 (d, J=9.3 Hz, 1H), 4.85-4.80 (m, 1H), 4.61 (s, 2H), 4.31-4.19 (m, 1H), 3.98-3.68 (m, 4H), 2.11-1.84 (m, 3H), 1.76-1.62 (m, 1H); MS (ES+) m/z 377.9 (M+1), 399.9 (M+23).

Preparation 22

Synthesis of 4-chloro-3-hydroxy-3-(6-hydroxy-1,3-benzodioxol-5-yl)-1,3-dihydro-2H-indol-2-one To a solution of 1,3-benzodioxol-5-ol (4.86 g, 22.0 mmol) in anhydrous tetrahydrofuran (100 mL) was added dropwise a solution of isopropyl magnesium chloride (49.6 mmol, 24.8 mL, 2.0 M solution in tetrahydrofuran) at 0° C. for 10 min. The reaction mixture was stirred for 30 min upon which time 4-chloroisatin (4.00 g, 22.0 mmol) was added in one portion. The reaction mixture was stirred at ambient temperature for 2 h and quenched by the addition of 10% aqueous hydrochloric acid (25.0 mL) and the mixture was concentrated in vacuo to dryness. The residue was diluted with ethyl acetate (100 mL), washed with saturated ammonium chloride (3×30 mL), dried over anhydrous sodium sulfate and filtered. The filtrate was concentrated in vacuo to dryness. The residue was triturated with hot diethyl ether to afford 4-chloro-3-hydroxy-3-(6-hydroxy-1,3-benzodioxol-5-yl)-1,3-dihydro-2H-indol-2-one (6.70 g, 95%) as a beige solid: mp 250-253° C.; $^1$H NMR (300 MHz, DMSO-d$_6$) δ 10.30, (s, 1H), 9.04 (s, 1H), 7.20 (s, 1H), 7.12 (t, J=8.0 Hz, 1H), 6.74 (d, J=8.2 Hz, 1H), 6.70 (d, J=7.7 Hz, 1H), 6.45 (s, 1H), 6.17 (s, 1H), 5.88 (d, J=6.7 Hz, 2H); $^{13}$C NMR (75 MHz, DMSO-d$_6$) δ 178.1, 148.6, 147.0, 145.6, 139.6, 130.6, 130.1, 129.6, 122.3, 118.6, 108.9, 108.4, 101.1, 97.4, 75.8; MS (ES−) m/z 304.2 (M−17), 302.2 (M−17).

Preparation 23

Synthesis of 4-chloro-3-(6-hydroxy-1,3-benzodioxol-5-yl)-1,3-dihydro-2H-indol-2-one To a solution of 4-chloro-3-hydroxy-3-(6-hydroxy-1,3-benzodioxol-5-yl)-1,3-dihydro-2H-indol-2-one (6.00 g, 18.8 mmol) in anhydrous dichloromethane (70.0 mL) was added trifluoroacetic acid (30.7 g, 269 mmol) and triethylsilane (18.0 mL, 13.1 g, 113 mmol) at ambient temperature. The reaction mixture was stirred at ambient temperature for 2 h. The reaction mixture was quenched with water (100.0 mL) and the solid was filtered. The solid was triturated with diethyl ether to afford 4-chloro-3-(6-hydroxy-1,3-benzodioxol-5-yl)-1,3-dihydro-2H-indol-2-one (4.71 g, 83%) as colourless solid: mp 210-225° C. (dec.); MS (ES+) m/z 304.1 (M+1), 302.1 (M+1).

Preparation 24

Synthesis of 4-chloro-3-(6-hydroxy-1,3-benzodioxol-5-yl)-1,3-bis(hydroxymethyl)-1,3-dihydro-2H-indol-2-one To a suspension of 4-chloro-3-(6-hydroxy-1,3-benzodioxol-5-yl)-1,3-dihydro-2H-indol-2-one (4.5 g, 14.9 mmol), para-formaldehyde (1.78 g, 59.4 mmol) in water (50.0 mL) was added the aqueous solution of sodium hydroxide (2.38 g, 59.4 mmol) in water (10.0 mL). The reaction mixture was stirred at 0° C. for 2 h and quenched with 10% hydrochloric acid (50.0 mL). The precipitate was filtered and washed with water (100.0 mL). The filtrate was extracted with ethyl acetate (3×50.0 mL). The combined organic solution was dried over anhydrous sodium sulfate and filtered. The filtrate was concentrated in vacuo to dryness. The residue was triturated with ethyl acetate and diethyl ether to afford 4-chloro-3-(6-hydroxy-1,3-benzodioxol-5-yl)-1,3-bis(hydroxymethyl)-1,3-dihydro-2H-indol-2-one (3.91 g, 72%) as a colourless solid: mp>210° C.; $^1$H NMR (300 MHz, DMSO-$d_6$) δ 9.04 (s, 1H), 7.17 (t, J=8.0 Hz, 1H), 6.99 (d, J=7.7 Hz, 1H), 6.86 (s, 1H), 6.83 (d, J=8.2 Hz, 1H), 6.18 (s, 1H), 5.87 (d, J=11.0 Hz, 2H), 5.03 (q, J=10.8 Hz, 2H), 4.86 (br, 1H), 4.64 (ABq, 2H); $^{13}$C NMR (75 MHz, DMSO-$d_6$) δ 177.9, 150.3, 146.9, 146.8, 139.9, 129.1, 129.0, 128.6, 122.7, 116.0, 108.8, 107.6, 101.2, 97.7, 63.6, 63.3, 56.6; MS (ES+) m/z 364.2 (M+1), 346.2 (M−17).

Preparation 25

Synthesis of 4'-chlorospiro[furo[2,3-f][1,3]benzodioxole-7,3'-indol]-2'(1'H)-one To a solution of 4-chloro-3-(6-hydroxy-1,3-benzodioxol-5-yl)-1,3-bis(hydroxymethyl)-1,3-dihydro-2H-indol-2-one (3.63 g, 10.0 mmol) in anhydrous tetrahydrofuran (100.0 mL) was added tributylphosphine (2.53 g, 12.5 mmol) at 0° C. followed by the solution of di-tert-butylazodicarboxylate (2.88 g, 12.5 mmol) in anhydrous tetrahydrofuran (25.0 mL). The reaction solution was stirred at 0° C. for 1 h followed by the addition of ammonium hydroxide (100.0 mL). The reaction mixture was continued to stir for another 2 h. The reaction was quenched with 10% aqueous solution of hydrochloric acid (100.0 mL). The reaction solution was extracted with ethyl acetate (3×100 mL). The combined organic solution was dried over anhydrous sodium sulfate and filtered. The filtrate was concentrated in vacuo to dryness. The residue was purified by flash chromatography with ethyl acetate in hexanes to afford 4'-chlorospiro[furo[2,3-f][1,3]benzodioxole-7,3'-indol]-2'(1'H)-one (0.98 g, 31%) as a colourless solid: mp 175-185° C.; $^1$H NMR (300 MHz, DMSO-$d_6$) δ 10.81 (s, 1H), 7.24 (t, J=8.0 Hz, 1H), 6.94 (d, J=8.2 Hz, 1H), 6.86 (d, J=7.1 Hz, 1H), 6.59 (s, 1H), 6.28 (s, 1H), 5.90 (d, J=2.5 Hz, 2H), 4.74 (ABq, J=9.5 Hz, 2H); $^{13}$C NMR (75 MHz, DMSO-$d_6$) δ 178.4, 157.0, 148.8, 144.2, 141.9, 130.9, 130.3, 129.2, 123.0, 117.5, 109.4, 103.3, 101.9, 93.3, 77.8, 58.9; MS (ES+) m/z 318.3 (M+1), 316.3 (M+1).

Preparation 26

Synthesis of 4'-chloro-2'-oxospiro[furo[2,3-f][1,3]benzodioxole-7,3'-indol]-1'(2'H)-yl)acetonitrile A mixture of 4'-chlorospiro[furo[2,3-f][1,3]benzodioxole-7,3'-indol]-2'(1'H)-one (2.00 g, 6.35 mmol), chloroacetonitrile (0.60 g, 7.94 mmol) and cesium carbonate in acetone (48.0 mL) and 2-butanone (24.0 mL) was heated at reflux for 1 h. The hot reaction mixture was filtered, and then washed with ethyl acetate. The filtrate was concentrated in vacuo to dryness. The residue was purified by flash chromatography with ethyl acetate in hexanes to afford 4'-chloro-2'-oxospiro [furo[2,3-f][1,3]benzodioxole-7,3'-indol]-1'(2'H)-yl)acetonitrile (2.11 g, 94%) as a colourless solid: mp 122-123° C.; $^1$H NMR (300 MHz, DMSO-$d_6$) δ 7.41 (dd, J=8.0, 8.0 Hz, 1H), 7.27 (d, J=7.9 Hz, 1H), 7.11 (d, J=8.1 Hz, 1H), 6.62 (s, 1H), 6.29 (s, 1H), 5.90 (d, J=1.9 Hz, 2H), 4.95 (ABq, J=17.9 Hz, 2H), 4.79 (ABq, J=9.9 Hz, 2H); $^{13}$C NMR (75 MHz, DMSO-$d_6$) δ 176.4, 156.7, 149.2, 143.0, 141.9, 131.1, 130.4, 128.4, 124.6, 116.8, 115.8, 108.8, 103.3, 101.9, 93.4, 77.6, 58.3, 29.2; MS (ES+) m/z 355.2 (M+1).

Preparation 27

Synthesis of 2-(4'-chloro-2'-oxospiro[furo[2,3-f][1,3] benzodioxole-7,3'-indol]-1'(2'H)-yl)-N'-hydroxyethanimidamide To a solution of 4'-chloro-2'-oxospiro[furo[2,3-f][1,3]benzodioxole-7,3'-indol]-1'(2'H)-yl)acetonitrile (1.81 g, 5.10 mmol) in ethanol (25.0 mL) and dimethylsulfoxide (3.0 mL) was added hydroxylamine (0.67 g, 20.4 mL) at ambient temperature. The yellow reaction solution was stirred for 2 h upon which time yellow precipitate formed. The precipitate was filtered, washed with water (100.0 mL) and dried under vacuum to afford 2-(4'-chloro-2'-oxospiro[furo[2,3-f][1,3] benzodioxole-7,3'-indol]-1'(2'H)-yl)-N'-hydroxyethanimidamide (1.54 g, 78%) as a fluffy yellow solid: mp 180-185° C.; $^1$H NMR (300 MHz, DMSO-$d_6$) δ 9.20 (s, 1H), 7.30 (d, J=8.0 Hz, 1H), 7.01 (d, J=3.8 Hz, 1H), 6.98 (d, J=3.5 Hz, 1H), 6.60 (s, 1H), 6.32 (s, 1H), 5.60 (d, J=3.8 Hz, 2H), 5.54 (br, 2H), 4.78 (ABq, J=9.6 Hz, 2H), 3.68 (s, 2H); $^{13}$C NMR (75 MHz, DMSO-$d_6$) δ 176.8, 156.6, 148.9, 147.7, 145.1, 141.9, 130.8, 129.9, 128.5, 123.5, 117.5, 109.1, 103.7, 101.9, 93.2, 77.5, 58.4, 40.9; MS (ES+) m/z 388.11 (M+1).

Example 1

Synthesis of 6-[2-(dimethylamino)ethoxy]-1'-(diphenylmethyl)spiro[1-benzofuran-3,3'-indol]-2'(1'H)-one

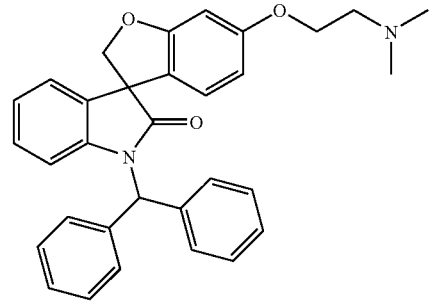

To a solution of 1-(diphenylmethyl)-6-hydroxyspiro[1-benzofuran-3,3'-indol]-2'(1'H)-one (0.69 g, 1.7 mol), N,N-dimethylethanolamine (0.83 mL, 8.3 mmol) and triphenylphosphine (1.74 g, 6.6 mmol) in tetrahydrofuran (50 mL) was added diethyl azodicarboxylate (1.05 mL, 6.6 mmol) slowly at 0° C. The mixture was stirred at ambient temperature for 16 h, then concentrated under vacuum. The residue was purified by column chromatography (ethyl acetate/methanol/ammonium hydroxide, 10/1/0.2) to afford 6-[2-(dimethylamino)ethoxy]-1'-(diphenylmethyl)spiro[1-benzofuran-3,3'-indol]-2'(1'H)-one (0.75 g, 92%) as an oil: $^1$H NMR (300 MHz, CDCl$_3$) δ 7.40-7.25 (m, 10H), 7.15-7.09 (m, 1H), 7.04 (s, 1H), 7.02-6.89 (m, 2H), 6.56-6.46 (m, 3H), 6.36 (dd, J=8.4, 2.1 Hz, 1H), 4.99 (d, J=9.0 Hz, 1H), 4.72 (d, J=9.0 Hz, 1H), 4.00 (t, J=5.8 Hz, 2H), 2.68 (t, J=5.8 Hz, 2H), 2.30 (s, 3H), 2.22 (s, 3H); MS (ES+) m/z 491.1 (M+1).

Example 2

Synthesis of 6-[2-(dimethylamino)ethoxy]spiro[1-benzofuran-3,3'-indol]-2'(1'H)-one

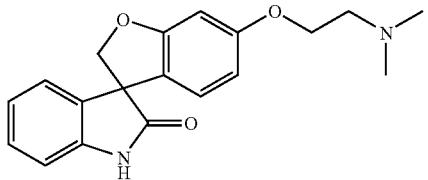

A mixture of 6-[2-(dimethylamino)ethoxy]-1'-(diphenylmethyl)spiro[1-benzofuran-3,3'-indol]-2'(1'H)-one (0.75 g, 1.5 mmol), triethylsilane (1.3 mL, 8.2 mmol) and trifluoroacetic acid (10 mL) was refluxed for 3 h. The mixture was concentrated under vacuum, and the residue was treated with diethyl ether/hexanes to afford 6-[2-(dimethylamino)ethoxy]spiro[1-benzofuran-3,3'-indol]-2'(1'H)-one (0.52 g, 99%) as a colorless solid: mp 95-97° C.; $^1$H NMR (300 MHz, DMSO-$d_6$) δ 10.58 (s, 1H), 7.21 (td, J=7.6, 1.3 Hz, 1H), 7.04 (d, J=6.4 Hz, 1H), 6.97-6.84 (m, 2H), 6.64-6.57 (m, 2H), 6.40 (dd, J=8.3, 2.3 Hz, 1H), 4.79 (d, J=9.3 Hz, 1H), 4.67 (d, J=9.3 Hz, 1H), 4.25 (t, J=4.7 Hz, 2H), 3.45 (t, J=4.7 Hz, 2H), 2.81 (s, 6H); $^{13}$C NMR (75 MHz, DMSO-$d_6$) δ 178.9, 162.1, 159.5, 142.3, 133.1, 129.2, 124.2, 124.1, 122.8, 122.7, 110.3, 108.2, 97.5, 80.4, 62.9, 57.6, 55.7, 43.2; MS (ES+) m/z 325.2 (M+1).

Example 3

Synthesis of 6-{[tris(1-methylethyl)silyl]oxy}spiro[1-benzofuran-3,3'-indol]-2'(1'H)-one

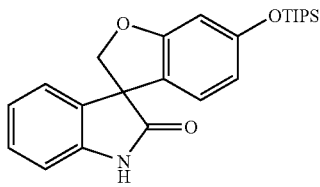

To a solution of 6-hydroxyspiro[1-benzofuran-3,3'-indol]-2'(1'H)-one (3.0 g, 11.8 mmol) in anhydrous N,N-dimethylformamide (30 mL) under nitrogen were added imidazole (1.97 g, 28.9 mmol) and triisopropylsilyl chloride (6.03 mL, 28.5 mmol). The reaction mixture was stirred at ambient temperature for 16 h. The reaction mixture was concentrated in vacuo to dryness. The residue was extracted with ethyl acetate (2×50 mL), the combined organic solution was dried over sodium sulfate, and filtered. The filtrate was concentrated and purified by flash chromatography with 30% ethyl acetate in hexanes to afford 6-{[tris(1-methylethyl)silyl]oxy}spiro[1-benzofuran-3,3'-indol]-2'(1'H)-one (2.68 g, 69% yield) as colorless solid: $^1$H NMR (300 MHz, CDCl$_3$) δ 8.48-8.08 (br, 1H), 7.29-6.90 (m, 4H), 6.10 (d, J=8.1 Hz, 1H), 6.50 (d, J=2.1 Hz, 1H), 6.35 (dd, J=8.1, 2.1 Hz, 1H), 4.96 (d, J=9.0 Hz, 1H), 4.69 (d, J=9.0 Hz, 1H), 1.34-0.98 (m, 21H).

Example 4

Synthesis of 1'-[(2R)-tetrahydrofuran-2-ylmethyl]-6-{[tris(1-methylethyl)silyl]oxy}spiro[1-benzofuran-3,3'-indol]-2'(1'H)-one

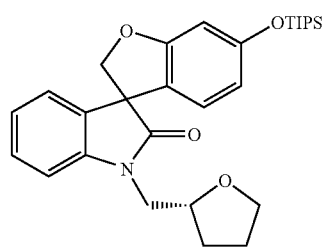

To a solution of 6-{[tris(1-methylethyl)silyl]oxy}spiro[1-benzofuran-3,3'-indol]-2'(1'H)-one (2.46 g, 6.0 mmol) in anhydrous N,N-dimethylformamide (10 mL) at 0° C. under nitrogen was added sodium hydride (0.24 g, 6.0 mmol). The above mixture was stirred at 0° C. for 20 min, then (R)-(tetrahydrofuran-2-yl)methyl 4-methylbenzenesulfonate (1.69 g, 6.6 mmol) was added. The reaction mixture was stirred at ambient temperature for 30 min, then heated to 60° C. for 5 h. The reaction was quenched with aqueous saturated ammonium chloride (10 mL), poured into water (15 mL) and extracted with ethyl acetate (3×40 mL). The combined organic solution was washed with water (2×50 mL) and brine (1×50 mL), dried over sodium sulfate, filtered, and concentrated. The residue was purified by column chromatography with 25% ethyl acetate in hexanes to afford 1-[(2R)-tetrahydrofuran-2-ylmethyl]-6-{[tris(1-methylethyl)silyl]oxy}spiro[1-benzofuran-3,3'-indol]-2'(1'H)-one (1.70 g, 58%) as a colorless oil: $^1$H NMR (300 MHz, CDCl$_3$) δ 7.33-7.26 (m, 1H), 7.14-6.98 (m, 3H), 6.53 (d, J=8.1 Hz, 1H), 6.48 (d, J=2.1 Hz, 1H), 6.32 (dd, J=8.1, 2.1 Hz, 1H), 4.95-4.90 (m, 1H), 4.66 (d, J=9.3 Hz, 1H), 4.34-4.22 (m, 1H), 4.00-3.66 (m, 4H), 2.10-1.66 (m, 4H), 1.34-0.98 (m, 21H); MS (ES+) m/z 494.2 (M+1).

Example 5

Synthesis of tert-butyl (3R)-3-({4-[(2'-oxospiro[furo[2,3-f][1,3]benzodioxole-7,3'-indol]-1'(2'H)-yl)methyl]phenyl}-amino)pyrrolidine-1-carboxylate

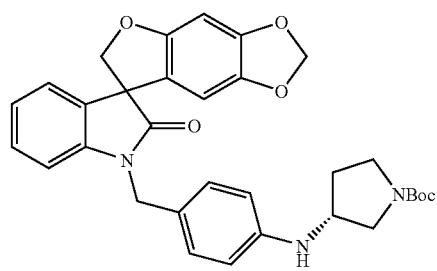

In an oven-dried 25 mL two-neck round bottom flask, equipped with a reflux condensor, was added (R)-1-Boc-3- aminopyrrolidine (0.26 g, 1.39 mmol), (±)-2,2'-bis(diphenylphosphino)-1,1'-binaphthalene (0.07 g, 0.11 mmol), tris(dibenzylideneacetone)dipalladium(0) (0.03 g, 0.03 mmol) and sodium tert-butoxide (0.16 g, 1.61 mmol). The flask was flushed with nitrogen and a solution of 1-(4-bromobenzyl) spiro[furo[2,3-f][1,3]benzodioxole-7,3'-indol]-2'(1'H)-one (0.50 g, 1.11 mmol) in freshly degassed toluene (5 mL) was added. The flask was flushed again with nitrogen and the reaction was stirred at reflux under nitrogen for 14.5 h. The mixture was cooled, diluted with ethyl acetate and filtered through Celite. The filtrate was concentrated under reduced pressure and the residue was purified by flash column chromatography with dichloromethane/diethyl ether (14:1) to afford tert-butyl (3R)-3-({4-[(2'-oxospiro[furo[2,3-f][1,3]benzodioxole-7,3'-indol]-1'(2'H)-yl)methyl]phenyl}-amino)pyrrolidine-1-carboxylate (0.60 g, 98%) as a pale brown solid: mp 115-118° C. (hexanes); $^1$H NMR (300 MHz, CDCl$_3$) 7.24-7.13 (m, 4H), 7.01 (dd, J=7.5, 7.5 Hz, 1H), 6.85 (d, J=7.8 Hz, 1H), 6.56 (d, J=8.4 Hz, 2H), 6.52 (s, 1H), 6.12 (s, 1H), 5.87 (s, 1H), 5.86 (s, 1H), 5.00-4.94 (m, 2H), 4.72-4.66 (m, 2H), 4.00 (br s, 1H), 3.80-3.62 (m, 2H), 3.52-3.38 (m, 2H), 3.30-3.13 (m, 1H), 2.22-2.11 (m, 1H), 1.93-1.80 (m, 1H), 1.46 (s, 9H); $^{13}$C NMR (75 MHz, CDCl$_3$) δ 177.6, 156.0, 154.7, 148.9, 146.6, 142.4, 142.3, 132.4, 128.95, 128.89, 124.8, 123.9, 123.3, 119.7, 113.4, 109.6, 103.2, 101.5, 93.7, 80.6, 79.6, 58.3, 53.0, 52.3, 52.2, 51.8, 44.2, 43.8; MS (ES+) m/z 578.2 (M+23).

Example 6

Synthesis of 1'-{4-[(3R)-pyrrolidin-3-ylamino] benzyl}spiro[furo[2,3-f][1,3]benzodioxole-7,3'-indol]-2'(1'H)-one

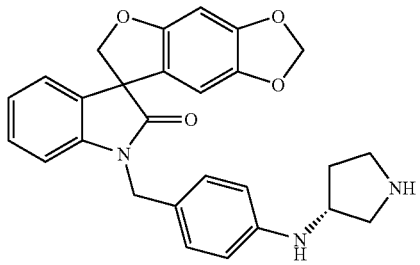

A solution of tert-butyl (3R)-3-({4-[(2'-oxospiro[furo[2,3-f][1,3]benzodioxole-7,3'-indol]-1'(2'H)-yl)methyl]phenyl}-amino)pyrrolidine-1-carboxylate (0.53 g, 0.94 mmol) and trifluoroacetic acid (1 mL) in dichloromethane (5 mL) was stirred at ambient temperature for 70 min. The reaction was made basic with 1 M sodium hydroxide (50 mL) and extracted with dichloromethane (4×30 mL). The combined organic solution was dried over sodium sulfate, filtered and concentrated under reduced pressure. Purification by flash column chromatography with dichloromethane/methanol/ammonium hydroxide (14:1:0.15) afforded 1'-{4-[(3R)-pyrrolidin-3-ylamino]benzyl}spiro[furo[2,3-f][1,3]benzodioxole-7,3'-indol]-2'(1'H)-one (0.34 g, 78%) as an off-white solid: mp 118-121° C. (hexanes); $^1$H NMR (300 MHz, CDCl$_3$) δ 7.23-7.13 (m, 4H), 7.00 (dd, J=7.5, 7.5 Hz, 1H), 6.86 (d, J=7.8 Hz, 1H), 6.55 (d, J=8.4 Hz, 2H), 6.52 (s, 1H), 6.12 (s, 1H), 5.87 (d, J=1.2 Hz, 1H), 5.85 (d, J=1.2 Hz, 1H), 4.99-4.94 (m, 2H), 4.71-4.66 (m, 2H), 3.94-3.85 (m, 1H), 3.83 (br s, 1H), 3.15-3.04 (m, 2H), 2.97-2.88 (m, 1H), 2.83 (dd, J=11.1, 3.0 Hz, 1H), 2.21-2.09 (m, 1H), 1.98 (br s, 1H), 1.67-1.57 (m, 1H); $^{13}$C NMR (75 MHz, CDCl$_3$) δ 177.6, 155.9, 148.8, 147.2, 142.3, 132.3, 128.85, 128.80, 124.3, 123.8, 123.3, 119.6, 113.4, 109.6, 103.1, 101.5, 93.6, 80.5, 58.3, 53.9, 53.6, 45.7, 43.8, 33.6; MS (ES+) m/z 456.2 (M+1).

Example 7

Synthesis of 1'-{4-[(3R)-pyrrolidin-3-ylamino] benzyl}spiro[furo[2,3-f][1,3]benzodioxole-7,3'-indol]-2'(1'H)-one hydrochloride

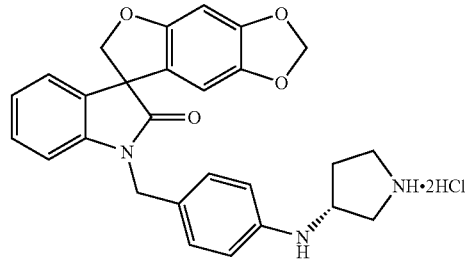

A mixture of 1-{4-[(3R)-pyrrolidin-3-ylamino] benzyl}spiro[furo[2,3-f][1,3]benzodioxole-7,3'-indol]-2'(1'H)-one (0.27 g, 0.59 mmol) and hydrochloric acid (2 M in diethyl ether, 1.6 mL, 3.2 mmol) in methanol (5 mL) was stirred at ambient temperature for 30 min. The mixture was diluted with diethyl ether and the precipitate was collected by filtration, and dried to afford 1-{4-[(3R)-pyrrolidin-3-ylamino]benzyl}spiro[furo[2,3-f][1,3]benzodioxole-7,3'-indol]-2'(1'H)-one hydrochloride (0.27 g, 87%) as a beige solid: mp 190-195° C. (hexanes); $^1$H NMR (300 MHz, DMSO-d$_6$) δ 9.30 (br s, 2H), 7.26 (ddd, J=7.8, 7.8, 0.9 Hz, 1H), 7.19-7.13 (m, 3H), 7.04-6.99 (m, 2H), 6.72 (s, 1H), 6.61 (d, J=8.4 Hz, 2H), 6.10 (s, 1H), 5.95 (s, 1H), 5.93 (s, 1H), 4.82 (d, J=9.3 Hz, 1H), 4.82 (d, J=14.9 Hz, 1H), 4.73 (d, J=14.9 Hz, 1H), 4.70 (d, J=9.3 Hz, 1H), 4.09-4.02 (m, 1H), 3.42-3.14 (m, 3H), 3.07-2.96 (m, 1H), 2.22-2.10 (m, 1H), 1.91-1.80 (m, 1H); $^{13}$C NMR (75 MHz, DMSO-d$_6$) δ 176.8, 155.4, 148.4, 145.2, 142.3, 141.7, 131.7, 128.8, 128.5, 125.7, 123.6, 123.0, 119.8, 114.2, 109.6, 102.8, 101.5, 93.4, 79.8, 57.5, 52.5, 49.0, 43.4, 42.8, 29.9; MS (ES+) m/z 456.2 (M+1).

Example 8

Synthesis of 1'-{[(2S)-1-acetylpyrrolidin-2-yl]methyl}-5,6-dihydrospiro[benzo[1,2-b:5,4-b']difuran-3,3'-indol]-2'(1'H)-one

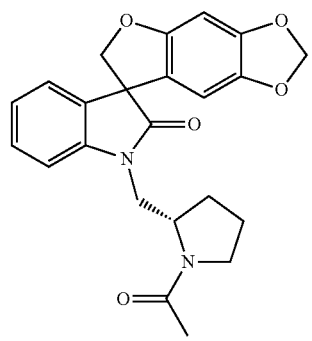

A solution of 1'-[(2S)-pyrrolidin-2-ylmethyl]-5,6-dihydrospiro[benzo[1,2-b:5,4-b']difuran-3,3'-indol]-2'(1'H)-one (0.23 g, 0.62 mmol), acetic anhydride (0.09 mL, 0.95 mmol) and triethylamine (0.17 mL, 1.2 mmol) in dichloromethane (4 mL) was stirred at ambient temperature for 40 min. The reaction was diluted with 0.2 M hydrochloric acid (50 mL) and extracted with dichloromethane (3×25 mL). The combined organic solution was dried over sodium sulfate, filtered and concentrated under reduced pressure. Purification by flash column chromatography with dichloromethane/diethyl ether (4:1) afforded 1'-{[(2S)-1-acetylpyrrolidin-2-yl]methyl}-5,6-dihydrospiro[benzo[1,2-b:5,4-b']difuran-3,3'-indol]-2'(1'H)-one (0.21 g, 84%) as an off-white solid: mp 103-108° C. (hexanes); $^1$H NMR (300 MHz, CDCl$_3$) (diastereomers) δ 7.54, 7.53 (d, J=7.8 Hz, 1H), 7.35, 7.34 (dd, J=8.1, 7.7 Hz, 1H), 7.15 (d, J=7.5 Hz, 1H), 7.06 (dd, J=7.5 Hz, 1H), 6.49, 6.46 (s, 1H), 6.42, 6.41 (s, 1H), 4.91, 4.90 (d, J=9.0 Hz, 1H), 4.68, 4.67 (d, J=9.0 Hz, 1H), 4.54, 4.53 (t, J=8.7 Hz, 2H), 4.49-4.42 (m, 1H), 3.95-3.80 (m, 2H), 3.61-3.54 (m, 1H), 3.46-3.36 (m, 1H), 3.00, 2.99 (t, J=8.6 Hz, 2H), 2.26-1.76 (m, 4H), 2.11-2.08 (s, 3H); $^{13}$C NMR (75 MHz, CDCl$_3$) (diastereomers) δ 178.49, 178.47, 170.2, 161.9, 161.8, 161.5, 161.4, 142.6, 142.4, 132.5, 132.3, 129.36, 129.33, 123.8, 123.7, 123.6, 123.5, 120.4, 120.2, 120.0, 119.9, 119.2, 118.7, 110.01, 109.96, 93.4, 93.2, 80.9, 80.8, 72.5, 57.9, 55.0, 54.8, 47.9, 41.5, 41.2, 29.2, 29.1, 28.0, 27.8, 23.9, 22.92, 22.90; MS (ES+) m/z 405.1 (M+1).

Example 9

Synthesis of N'-hydroxy-4-[(2'-oxo-5,6-dihydrospiro [benzo[1,2-b:5,4-b']difuran-3,3'-indol]-1'(2'H)-yl) methyl]benzenecarboximidamide

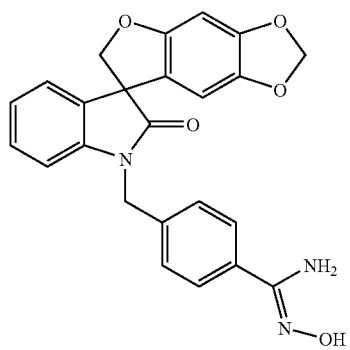

To a stirred solution of 4-[(2'-oxo-5,6-dihydrospiro[benzo [1,2-b:5,4-b']difuran-3,3'-indol]-1'(2'H)-yl)methyl]benzonitrile (1.30 g, 32.9 mmol) in dimethyl sulfoxide (10 mL) was added 50% wt solution hydroxylamine in water (2 mL). The reaction was heated with stirring at 80° C. for 1 h, then cooled to ambient temperature and the product was precipitated by adding distilled water (25 mL). The solid was filtered and air dried to afford N'-hydroxy-4-[(2'-oxo-5,6-dihydrospiro [benzo[1,2-b:5,4-b']difuran-3,3'-indol]-1'(2'H)-yl)methyl] benzenecarboximidamide (1.32 g, 93%) as a colorless solid: $^1$H NMR (300 MHz, CDCl$_3$) δ 9.17 (s, 1H), 7.40-7.03 (m, 13H), 6.99-6.92 (m, 2H), 6.79-6.74 (m, 2H), 6.58-6.50 (m, 1H), 5.10 (s, 1H); MS (ES−) m/z 468.2, 470.2 (M−1).

Example 10

Synthesis of N'-hydroxy-3-(2'-oxo-6H-spiro[benzofuro[6,5-d][1,3]-dioxole-7,3'-indoline]-1'-yl)propanimidamide

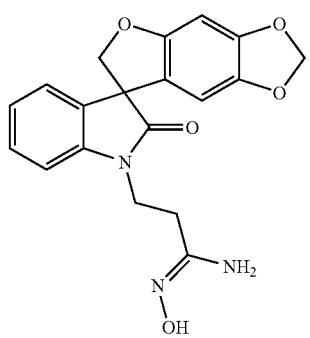

To a stirred solution of 3-(2'-oxo-6H-spiro[benzofuro[6,5-d][1,3]dioxole-7,3'-indoline]-1'-yl)propanenitrile (2.00 g, 6.0 mmol) in dimethyl sulfoxide (15.0 mL) was added hydroxylamine (50% wt solution in water, 1.6 mL, 24 mmol). The reaction was stirred at ambient temperature for 16 h, then the product was precipitated upon addition of water/ethanol (3:1, 100 mL). The solvent was decanted and the remaining solid was triturated in distilled water (75 mL). The solid was filtered and air-dried to afford N'-hydroxy-3-(2'-oxo-6H-spiro[benzofuro[6,5-d][1,3]dioxole-7,3'-indoline]-1'-yl)propanimidamide as a colorless solid (2.00 g, 91%): MS (ES+) m/z 368.2 (M+1).

Example 11

Synthesis of 2-(4'-chloro-2'-oxospiro[furo[2,3-f][1,3] benzodioxole-7,3'-indol]-1'(2'H)-yl)-N'-[(cyclopropylcarbonyl)oxy]ethanimidamide

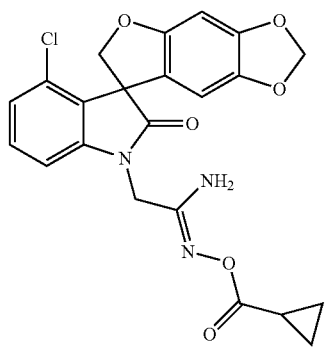

A stirred solution of 2-(4'-chloro-2'-oxo-6H-spiro[benzofuro[6,5-d][1,3]dioxole-7,3'-indoline]-1'-yl)-N'-hydroxyacetimidamide (0.40 g, 1.0 mmol), diisopropylamine (0.16 g, 1.6 mmol) and cyclopropane carbonyl chloride (0.16 g, 1.6 mmol) in dichloromethane (20 mL) was stirred for 16 h at ambient temperature. The colorless solid that precipitated from the solution was filtered, washed with water (5 mL) and diethyl ether (5 mL) to afford 2-(4'-chloro-2'-oxospiro[furo[2,3-f][1,3]benzodioxole-7,3'-indol]-1'(2'H)-yl)-N'-[(cyclopropylcarbonyl)oxy]ethanimidamide (0.25 g, 53%) as a colorless solid: $^1$H NMR (300 MHz, DMSO-$d_6$) δ 7.31 (dd, J=8.0, 8.0 Hz, 1H), 7.02 (d, J=8.0 Hz, 2H), 6.64 (br s, 2H), 6.54 (s, 1H), 6.47 (s, 1H), 5.88 (s, 2H), 4.77 (ABq, 2H), 4.43 (ABq, 2H), 1.75-1.67 (m, 1H), 0.86-0.73 (m, 4H); $^{13}$C NMR (75 MHz, DMSO-$d_6$) δ 176.9, 171.9, 156.5, 153.6, 148.9, 144.8, 141.9, 130.8, 130.0, 128.6, 117.4, 108.8, 104.4, 101.8, 104.5, 101.8, 104.4, 101.8, 93.0, 77.5, 58.4, 11.7, 8.45, 8.42; MS (ES+) m/z 456.1 (M+1), 478.1 (M+23).

Example 12

Synthesis of N'-hydroxy-3-[(2'-oxo-5,6-dihydrospiro[benzo[1,2-b:5,4-b']difuran-3,3'-indol]-1'(2'H)-yl)methyl]benzenecarboximidamide

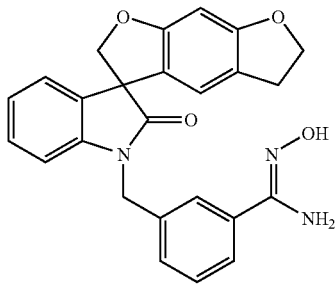

To a solution of 3-[(2'-oxo-5,6-dihydrospiro[benzo[1,2-b:5,4-b']difuran-3,3'-indol]-1'(2'H)-yl)methyl]benzonitrile (1.15 g, 2.92 mmol) in dimethyl sulfoxide (20 mL) was added hydroxylamine (50% wt in H$_2$O, 2 mL, 32.67 mmol). The reaction was stirred at 80° C. for 3 h, and cooled to ambient temperature. The precipitate was collected by filtration, washed with water and diethyl ether, and dried in vacuo to afford N'-hydroxy-3-[(2'-oxo-5,6-dihydrospiro[benzo[1,2-b:5,4-b']difuran-3,3'-indol]-1'(2'H) yl)methyl]benzenecarboximidamide (0.85 g, 68%): $^1$H NMR (300 MHz, CDCl$_3$) δ 7.96 (br s, 1H), 7.61 (s, 1H), 7.53-7.50 (m, 1H), 7.38-7.35 (m, 2H), 7.21-7.15 (m, 2H), 7.03-6.98 (m, 1H), 6.77-6.74 (m, 1H), 6.48 (s, 1H), 6.40 (s, 1H), 5.12-4.68 (m, 6H), 4.49 (t, J=8.6 Hz, 2H), 3.01-2.91 (m, 2H); MS (ES+) m/z 427.8 (M+1).

Example 13

Synthesis of 2-{3-[(2-oxo-5,6-dihydrospiro[benzo[1,2-b:5,4-b']difuran-3,3'-indol]-1(2H)-yl)methyl]phenoxy}acetamide

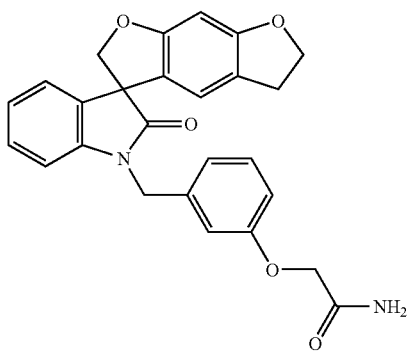

To a stirred solution of 1'-(3-hydroxybenzyl)-5,6-dihydrospiro[benzo[1,2-b:5,4-b']difuran-3,3'-indol]-2'(1'H)-one (0.30 g, 0.78 mmol) in N,N-dimethylformamide (2 mL) was added potassium carbonate (0.32 g, 2.3 mmol) at ambient temperature and 2-iodoacetamide (0.29 g, 1.6 mmol). The mixture was stirred at 40° C. for 16 h. Water (20 mL) and chloroform (80 mL) were added to the mixture. The organic solution was separated and the aqueous layer was extracted with chloroform (2×80 mL). The combined organic solution was washed with saturated aqueous sodium bicarbonate solution (60 mL), brine (60 mL), dried over anhydrous magnesium sulfate, filtered, and concentrated in vacuo. The residue was purified by column chromatography (hexanes/ethyl acetate from 1:1 to 1:2 to 0:1) to afford 2-{3-[(2-oxo-5,6-dihydrospiro[benzo[1,2-b:5,4-b]difuran-3,3-indol]-1(2H)-yl)methyl]phenoxy}acetamide (0.30 g, 87%) as a colorless solid: mp 109-111° C.; $^1$H NMR (300 MHz, CDCl$_3$) δ 7.54 (s, 1H), 7.39 (s, 1H), 7.33-7.22 (m, 2H), 7.21-7.16 (m, 1H), 7.06-6.92 (m, 4H), 6.89-6.84 (m, 1H), 6.46 (s, 1H), 6.43 (s, 1H), 5.00-4.81 (m, 3H), 4.77-4.71 (m, 1H), 4.55-4.45 (m, 2H), 4.39 (s, 1H), 3.07-2.87 (m, 2H); $^{13}$C NMR (75 MHz, CDCl$_3$) δ 177.1, 169.7, 161.1, 160.6, 158.0, 142.1, 137.9, 132.0, 129.8, 128.6, 123.6, 123.1, 120.4, 119.9 (2C), 118.9, 113.7, 113.5, 109.4, 92.5, 79.8, 72.1, 66.6, 56.9, 42.9, 28.3; MS (ES+) m/z 443.0 (M+1).

Example 13.1

Synthesis of 2-{4-[(2'-oxo-5,6-dihydrospiro[benzo[1,2-b:5,4-b']difuran-3,3'-indol]-1'(2'H)-yl)methyl]phenoxy}acetamide

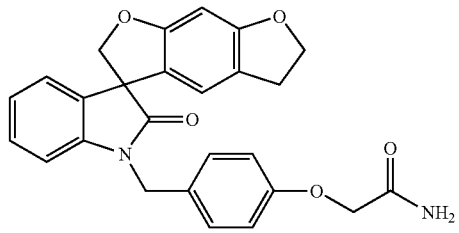

Following the procedure as described in EXAMPLE 13 and making non-critical variations using 1'-(4-hydroxybenzyl)-5,6-dihydrospiro[benzo[1,2-b:5,4-b']difuran-3,3'-indol]-2'(1'H)-one to replace 1'-(3-hydroxybenzyl)-5,6-dihydrospiro[benzo[1,2-b:5,4-b']difuran-3,3'-indol]-2'(1'H)-one, 2-{4-[(2'-oxo-5,6-dihydrospiro[benzo[1,2-b:5,4-b']difuran-3,3'-indol]-1'(2'H)-yl)methyl]phenoxy}acetamide was obtained (81%) as a colorless solid: mp 215-216° C.; $^1$H NMR (300 MHz, CDCl$_3$) δ 7.35-7.29 (m, 2H), 7.25-7.14 (m, 2H), 7.06-6.99 (m, 1H), 6.93-6.87 (m, 2H), 6.83-6.78 (m, 1H), 6.52 (br s, 1H), 6.46 (s, 1H), 6.43 (s, 1H), 5.67 (br s, 1H), 5.04-4.95 (m, 2H), 4.85-4.76 (m, 1H), 4.73-4.66 (m, 1H), 4.59-4.50 (m, 2H), 4.48 (s, 2H), 3.10-2.90 (m, 2H); $^{13}$C NMR (75 MHz, CDCl$_3$) δ 177.9, 170.7, 161.8, 160.3, 156.7, 142.0, 132.7, 129.6, 129.0, 128.6, 123.9, 123.4, 120.1, 119.9, 118.8, 115.0, 109.1, 93.2, 80.6, 72.4, 67.1, 57.7, 43.4, 29.0; MS (ES+) m/z 443.0 (M+1).

Example 13.2

Synthesis of 2-{4-[(2'-oxo-2,3-dihydrospiro[furo[2,3-g][1,4]benzodioxine-8,3'-indol]-1'(2'H)-yl)methyl]phenoxy}acetamide

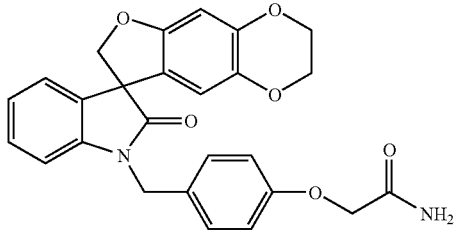

Following the procedure as described in EXAMPLE 13 and making non-critical variations using 1'-(4-hydroxybenzyl)-2,3-dihydrospiro[furo[2,3-g][1,4]benzodioxine-8,3'-indol]-2'(1'H)-one to replace 1-(3-hydroxybenzyl)-5,6-dihydrospiro[benzo[1,2-b:5,4-b']difuran-3,3'-indol]-2'(1H)-one, 2-{4-[(2'-oxo-2,3-dihydrospiro[furo[2,3-g][1,4]benzodioxine-8,3'-indol]-1'(2'H)-yl)methyl]phenoxy}acetamide was obtained (63%) as a colorless solid: mp 225-227° C.; $^1$H NMR (300 MHz, DMSO-d$_6$) δ 7.51 (s, 1H), 7.38 (s, 1H), 7.33-7.22 (m, 3H), 7.19-7.13 (m, 1H), 7.05-6.98 (m, 2H), 6.96-6.90 (m, 2H), 6.53 (s, 1H), 6.07 (s, 1H), 4.86 (ABq, J=27.4, 15.3 Hz, 2H), 4.74 (ABq, J=40.5, 9.3 Hz, 2H), 4.39 (s, 2H), 4.22-4.08 (m, 4H); $^{13}$C NMR (75 MHz, DMSO-d$_6$) δ 176.6, 169.8, 157.1, 154.6, 144.1, 142.1, 137.8, 131.7, 128.8, 128.7, 128.5, 123.6, 123.0, 121.2, 114.8, 110.9, 109.4, 98.8, 79.4, 66.6, 64.2, 63.5, 57.2, 42.4; MS (ES+) m/z 458.9 (M+1).

Example 13.3

Synthesis of 1-[4-(2-methoxyethoxy)benzyl]-2,3-dihydrospiro[furo[2,3-g][1,4]benzodioxine-8,3'-indol]-2'(1'H)-one

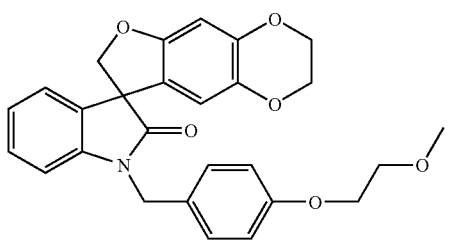

Following the procedure as described in EXAMPLE 13 and making non-critical variations using 1'-(4-hydroxybenzyl)-2,3-dihydrospiro[furo[2,3-g][1,4]benzodioxine-8,3'-indol]-2'(1'H)-one to replace 1'-(3-hydroxybenzyl)-5,6-dihydrospiro[benzo[1,2-b:5,4-b']difuran-3,3'-indol]-2'(1'H)-one, and 2-bromoethyl methyl ether to replace 2-iodoacetamide, 1'-[4-(2-methoxyethoxy)benzyl]-2,3-dihydrospiro[furo[2,3-g][1,4]benzodioxine-8,3'-indol]-2'(1'H)-one was obtained (68%) as a colorless solid: mp 124-125° C.; $^1$H NMR (300 MHz, CDCl$_3$) δ 7.29-7.11 (m, 4H), 7.04-6.96 (m, 1H), 6.93-6.87 (m, 2H), 6.82-6.77 (m, 1H), 6.50 (s, 1H), 6.21 (s, 1H), 4.88 (ABq, J=76.5, 15.3 Hz, 2H), 4.79 (ABq, J=83.8, 8.9 Hz, 2H), 4.22-4.07 (m, 6H), 3.76-3.71 (m, 2H), 3.44 (s, 3H); $^{13}$C NMR (300 MHz, CDCl$_3$) δ 177.5, 158.4, 155.2, 144.6, 142.1, 138.3, 132.3, 128.7, 128.0, 123.8, 123.3, 121.1, 114.9, 111.5, 109.3, 99.4, 80.1, 71.0, 67.2, 64.5, 63.9, 59.2, 58.0, 43.6; MS (ES+) m/z 460.0 (M+1).

Example 13.4

Synthesis of 1'-{-4-[2-(dimethylamino)ethoxy]benzyl}-2,3-dihydrospiro[furo[2,3-g][1,4]benzodioxine-8,3'-indol]-2'(1'H)-one

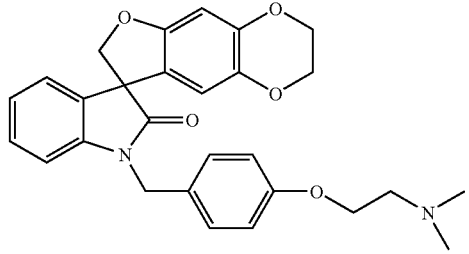

Following the procedure as described in EXAMPLE 13 and making non-critical variations using 1'-(4-hydroxybenzyl)-2,3-dihydrospiro[furo[2,3-g][1,4]benzodioxine-8,3'-indol]-2'(1'H)-one to replace 1'-(3-hydroxybenzyl)-5,6-dihydrospiro[benzo[1,2-b:5,4-b']difuran-3,3'-indol]-2'(1'H)-one, and 2-(dimethylamino)ethyl chloride hydrochloride to replace 2-iodoacetamide, 1'-{4-[2-(dimethylamino)ethoxy]benzyl}-2,3-dihydrospiro[furo[2,3-g][1,4]benzodioxine-8,3'-indol]-2'(1'H)-one was obtained (26%) as a colorless solid: mp 77-79° C.; $^1$H NMR (300 MHz, CDCl$_3$) δ 7.30-7.11 (m, 4H), 7.05-6.97 (m, 1H), 6.92-6.86 (m, 2H), 6.82-6.78 (m, 1H), 6.51 (s, 1H), 6.21 (s, 1H), 4.88 (ABq, J=77.2, 15.3 Hz, 2H), 4.79 (ABq, J=83.8, 8.9 Hz, 2H), 4.23-4.05 (m, 6H), 2.84-2.75 (m, 2H), 2.40 (s, 6H); $^{13}$C NMR (300 MHz, CDCl$_3$) δ 177.5, 158.3, 155.2, 144.6, 142.1, 138.3, 132.3, 128.7, 127.9, 123.8, 123.3, 121.1, 114.9, 111.5, 109.3, 99.4, 80.2, 65.8, 64.5, 63.9, 58.2, 58.0, 45.8, 43.6; MS (ES+) m/z 472.8 (M+1).

Example 14

Synthesis of ethyl {3-[(2'-oxo-5,6-dihydrospiro[benzo[1,2-b:5,4-b']difuran-3,3'-indol]-1'(2'H)-yl)methyl]phenoxy}acetate

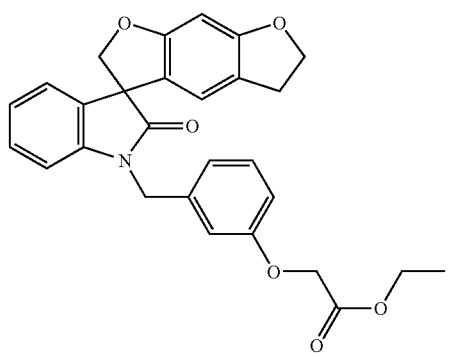

To a stirred solution of 1'-(3-hydroxybenzyl)-5,6-dihydrospiro[benzo[1,2-b:5,4-b']difuran-3,3'-indol]-2'(1'H)-one (0.46 g, 1.18 mmol) in N,N-dimethylformamide (4 mL) were added potassium carbonate (0.32 g, 2.36 mmol), ethyl bromoacetate (0.20 mL, 1.77 mmol), and potassium iodide (0.024 g, 0.14 mmol) at ambient temperature. The mixture was stirred at 40° C. for 16 h. Water (50 mL) and ethyl acetate (150 mL) were added to the mixture. The organic solution was separated and the aqueous layer was extracted with ethyl acetate (2×80 mL). The combined organic solution was washed with brine (100 mL), dried over anhydrous magnesium sulfate, filtered, and concentrated in vacuo. The residue was purified by column chromatography (hexanes/ethyl acetate from 2:1 to 1:1) to afford ethyl {3-[(2'-oxo-5,6-dihydrospiro[benzo[1,2-b:5,4-b']difuran-3,3'-indol]-1'(2'H)-yl)methyl]phenoxy}acetate (0.52 g, 93%): mp 45-46° C.; $^1$H NMR (300 MHz, CDCl$_3$) δ 7.30-7.15 (m, 3H), 7.06-6.96 (m, 2H), 6.90 (br s, 1H), 6.84-6.76 (m, 2H), 6.50 (s, 1H), 6.43 (s, 1H), 5.07-4.96 (m, 2H), 4.87-4.78 (m, 1H), 4.75-4.68 (m, 1H), 4.60-4.50 (m, 4H), 4.22 (q, J=7.1 Hz, 2H), 3.11-2.91 (m, 2H), 1.26 (t, J=7.1 Hz, 3H); $^{13}$C NMR (75 MHz, CDCl$_3$) δ 177.9, 168.7, 161.8, 161.3, 158.2, 142.0, 137.6, 132.7, 130.0, 128.7, 123.8, 123.4, 120.7, 120.2, 119.9, 118.9, 114.0, 113.7, 109.2, 93.2, 80.6, 72.4, 65.4, 61.4, 57.7, 44.0, 29.0, 14.1; MS (ES+) m/z 471.9 (M+1).

Example 14.1

Synthesis of ethyl {4-[(2'-oxo-5,6-dihydrospiro[benzo[1,2-b:5,4-b']difuran-3,3'-indol]-1'(2'H)-yl)methyl]phenoxy}acetate

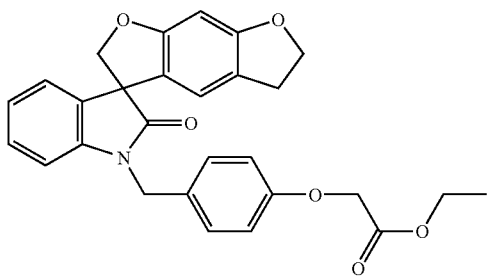

Following the procedure as described in EXAMPLE 14 and making non-critical variations using 1'-(4-hydroxybenzyl)-5,6-dihydrospiro[benzo[1,2-b:5,4-b']difuran-3,3'-indol]-2'(1H)-one to replace 1'-(3-hydroxybenzyl)-5,6-dihydrospiro[benzo[1,2-b:5,4-b']difuran-3,3'-indol]-2'(1H)-one, ethyl {4-[(2'-oxo-5,6-dihydrospiro[benzo[1,2-b:5,4-b']difuran-3,3'-indol]-1'(2'H)-yl)methyl]phenoxy}acetate was obtained (76%) as a colorless solid: mp 158-159° C.; $^1$H NMR (300 MHz, CDCl$_3$) δ 7.33-7.13 (m, 4H), 7.06-6.98 (m, 1H), 6.92-6.84 (m, 2H), 6.84-6.77 (m, 1H), 6.46 (s, 1H), 6.43 (s, 1H), 4.89 (ABq, J=64.4, 15.3 Hz, 2H), 4.84 (ABq, J=82.8, 9.0 Hz, 2H), 4.60 (s, 2H), 4.58-4.51 (m, 2H), 4.27 (q, J=7.1 Hz, 2H), 3.10-2.91 (m, 2H), 1.29 (t, J=7.1 Hz, 3H); $^{13}$C NMR (75 MHz, CDCl$_3$) δ 177.9, 168.8, 161.8, 161.3, 157.4, 142.0, 132.8, 129.0, 128.9, 128.6, 123.8, 123.3, 120.2, 119.9, 118.8, 115.0, 109.2, 93.2, 80.6, 72.4, 65.4, 61.4, 57.7, 43.5, 29.0, 14.1; MS (ES+) m/z 472.0 (M+1).

Example 14.2

Synthesis of ethyl {4-[(2'-oxo-2,3-dihydrospiro[furo[2,3-g][1,4]benzodioxine-8,3'-indol]-1'(2'H)-yl)methyl]phenoxy}acetate

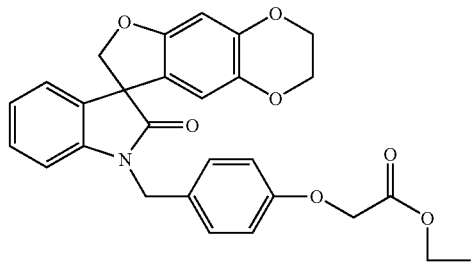

Following the procedure as described in EXAMPLE 14 and making non-critical variations using 1'-(4-hydroxybenzyl)-2,3-dihydrospiro[furo[2,3-g][1,4]benzodioxine-8,3'-indol]-2'(1'H)-one to replace 1'-(3-hydroxybenzyl)-5,6-dihydrospiro[benzo[1,2-b:5,4-b']difuran-3,3'-indol]-2'(1'H)-one, ethyl {4-[(2'-oxo-2,3-dihydrospiro[furo[2,3-g][1,4]benzodioxine-8,3'-indol]-1'(2'H)-yl)methyl]phenoxy}acetate was obtained (95%) as a colorless solid: mp 59-61° C.; $^1$H NMR (300 MHz, CDCl$_3$) δ 7.34-7.12 (m, 4H), 7.05-6.98 (m, 1H), 6.91-6.85 (m, 2H), 6.81-6.77 (m, 1H), 6.51 (s, 1H), 6.21 (s, 1H), 4.89 (ABq, J=73.0, 15.4 Hz, 2H), 4.79 (ABq, J=82.8, 8.9 Hz, 2H), 4.61-4.59 (m, 2H), 4.27 (q, J=7.2 Hz, 2H), 4.22-4.10 (m, 4H), 1.29 (t, J=7.1 Hz, 3H); $^{13}$C NMR (75 MHz, CDCl$_3$) δ 177.5, 168.8, 157.4, 155.2, 144.6, 142.0, 138.3, 132.3, 128.9, 128.8, 128.7, 123.8, 123.3, 121.1, 115.0, 111.5, 109.3, 99.4, 80.1, 65.4, 64.5, 63.9, 61.4, 58.0, 43.5, 14.1; MS (ES+) m/z 488.0 (M+1).

Example 15

Synthesis of {3-[(2'-oxo-5,6-dihydrospiro[benzo[1,2-b:5,4-b']difuran-3,3'-indol]-1'(2'H)-yl)methyl]phenoxy}acetic acid

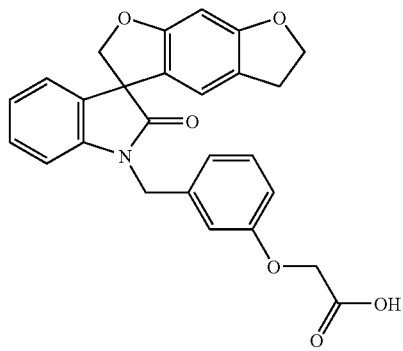

To a stirred solution of ethyl {3-[(2'-oxo-5,6-dihydrospiro[benzo[1,2-b:5,4-b']difuran-3,3'-indol]-1'(2'H)-yl)methyl]phenoxy}acetate (0.46 g, 0.98 mmol) in a mixture of tetrahydrofuran (30 mL) and water (15 mL) was added lithium hydroxide monohydrate (0.32 g, 2.3 mmol) at ambient temperature. The mixture was stirred at ambient temperature for 16 h. The mixture was concentrated in vacuo to a small volume, diluted with water (15 mL), washed with diethyl ether (60 mL), and acidified with 37% hydrochloric acid to pH 1. A white precipitate was formed. The mixture was extracted with ethyl acetate (3×60 mL). The combined organic solution was washed with water (30 mL), brine (50 mL), dried over anhydrous magnesium sulfate, filtered, and concentrated in vacuo to afford {3-[(2'-oxo-5,6-dihydrospiro[benzo[1,2-b:5,4-b']difuran-3,3'-indol]-1'(2'H)-yl)methyl]phenoxy}acetic acid (0.41 g, 95%): mp 95-96° C.; $^1$H NMR (300 MHz, CDCl$_3$) 7.33-7.14 (m, 3H), 7.07-6.97 (m, 2H), 6.92 (br s, 1H), 6.88-6.77 (m, 2H), 6.48 (s, 1H), 6.42 (s, 1H), 5.08-4.95 (m, 2H), 4.88-4.79 (m, 1H), 4.74-4.67 (m, 1H), 4.63 (s, 2H), 4.57-4.48 (m, 2H), 3.09-2.89 (m, 2H); $^{13}$C NMR (75 MHz, CDCl$_3$) δ 178.2, 172.6, 161.8, 161.3, 157.9, 141.9, 137.6, 132.6, 130.1, 128.8, 123.9, 123.6, 120.9, 120.0, 118.9, 113.9, 113.7, 113.7, 109.3, 93.2, 80.5, 72.4, 64.7, 57.8, 44.0, 29.0; MS (ES+) m/z 444.0 (M+1).

Example 15.1

Synthesis of {4-[(2'-oxo-5,6-dihydrospiro[benzo[1,2-b:5,4-b']difuran-3,3'-indol]-1'(2'H)-yl)methyl]phenoxy}acetic acid

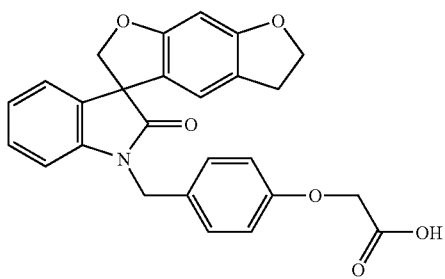

Following the procedure as described in EXAMPLE 15 and making non-critical variations using ethyl {4-[(2'-oxo-5,6-dihydrospiro[benzo[1,2-b:5,4-b']difuran-3,3'-indol]-1'(2'H)-yl)methyl]phenoxy}acetate to replace ethyl {3-[(2'-oxo-5,6-dihydrospiro[benzo[1,2-b:5,4-b']difuran-3,3'-indol]-1'(2'H)-yl)methyl]phenoxy}acetate, {4-[(2'-oxo-5,6-dihydrospiro[benzo[1,2-b:5,4-b']difuran-3,3'-indol]-1'(2'H)-yl)methyl]phenoxy}acetic acid was obtained (88%) as a colorless solid: mp 265-266° C.; $^1$H NMR (300 MHz, DMSO-d$_6$) δ 12.99 (s, 1H), 7.33-7.21 (m, 3H), 7.19-7.14 (m, 1H), 7.05-6.98 (m, 2H), 6.93-6.86 (m, 2H), 6.43 (s, 1H), 6.41 (s, 1H), 4.86 (q, J=15.5 Hz, 2H), 4.79 (ABq, J=38.0, 9.3 Hz, 2H), 4.65 (s, 2H), 4.55-4.46 (m, 2H), 3.04-2.90 (m, 2H); $^{13}$C NMR (75 MHz, DMSO-d$_6$) δ 177.0, 170.1, 161.1, 160.6, 157.0, 142.1, 132.1, 128.7, 128.5, 123.6, 122.9, 120.4, 119.8, 118.8, 114.6, 109.4, 92.4, 79.8, 72.0, 64.3, 56.9, 42.4, 28.3; MS (ES+) m/z 443.8 (M+1).

Example 15.2

Synthesis of {4-[(2'-oxo-2,3-dihydrospiro[furo[2,3-g][1,4]benzodioxine-8,3'-indol]-1'(2'H)-yl)methyl]phenoxy}acetic acid

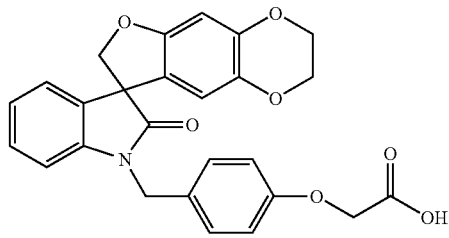

Following the procedure as described in EXAMPLE 15 and making non-critical variations using ethyl {4-[(2'-oxo-2,3-dihydrospiro[furo[2,3-g][1,4]benzodioxine-8,3'-indol]-1'(2'H)-yl)methyl]phenoxy}acetate to replace ethyl {3-[(2'-oxo-5,6-dihydrospiro[benzo[1,2-b:5,4-b']difuran-3,3'-indol]-1'(2'H)-yl)methyl]phenoxy}acetate, {4-[(2'-oxo-2,3-dihydrospiro[furo[2,3-g][1,4]benzodioxine-8,3'-indol]-1'(2'H)-yl)methyl]phenoxy}acetic acid was obtained (66%) as a colorless solid: mp 223-224° C.; $^1$H NMR (300 MHz, DMSO-d$_6$) δ 13.00 (s, 1H), 7.31-7.22 (m, 3H), 7.18-7.13 (m, 1H), 7.05-6.98 (m, 2H), 6.92-6.85 (m, 2H), 6.53 (s, 1H), 6.08 (s, 1H), 4.93-4.77 (m, 3H), 4.70-4.61 (m, 3H), 4.21-4.08 (m, 4H); $^{13}$C NMR (75 MHz, DMSO-d$_6$) δ 180.6, 176.6, 170.1, 157.0, 154.7, 144.1, 142.1, 137.8, 131.7, 128.7, 128.5, 123.6, 123.0, 121.2, 114.6, 110.9, 109.4, 98.8, 79.4, 64.4, 64.2, 63.5, 57.2, 42.4; MS (ES+) m/z 459.9 (M+1).

Example 15.3

Synthesis of 1'-[4-(2-hydroxyethoxy)benzyl]-2,3-dihydrospiro[furo[2,3-g][1,4]benzodioxine-8,3'-indol]-2'(1'H)-one

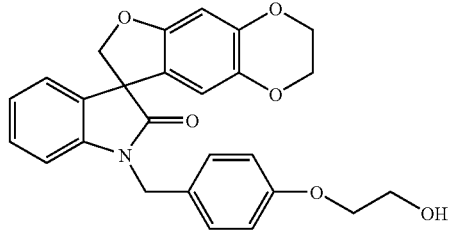

To a solution of ethyl {4-[(2'-oxo-2,3-dihydrospiro[furo[2,3-g][1,4]benzodioxine-8,3'-indol]-1'(2'H)-yl)methyl]phenoxy}acetate (0.22 g, 0.44 mmol) in anhydrous 1,2-dimethoxyethane (5 mL) was added at 0° C. lithium borohydride (2.0 M solution in tetrahydrofuran, 0.44 mL, 0.88 mmol) dropwise. The mixture was stirred at ambient temperature for 2 h, cooled to 0° C., and 7% w/v aqueous citric acid (15 mL) was added dropwise. The mixture was extracted with chloroform (3×60 mL). The combined organic layers was washed with saturated aqueous sodium bicarbonate (50 mL) and brine (50 mL), dried over anhydrous magnesium sulfate, filtered and concentrated in vacuo. The residue was purified by column chromatography eluted with 50% ethyl acetate in hexanes to afford 1'-[4-(2-hydroxyethoxy)benzyl]-2,3-dihydrospiro[furo[2,3-g][1,4]benzodioxine-8,3'-indol]-2'(1'H)-one (0.12 g, 63%) as a colorless solid: mp 196-197° C.; $^1$H NMR (300 MHz, CDCl$_3$) δ 7.31-7.24 (m, 2H), 7.23-7.12 (m, 2H), 7.05-6.97 (m, 1H), 6.92-6.86 (m, 2H), 6.83-6.78 (m, 1H), 6.51 (s, 1H), 6.22 (s, 1H), 4.89 (ABq, J=79.6, 15.4 Hz, 2H), 4.79 (ABq, J=83.8, 8.9 Hz, 2H), 4.22-4.08 (m, 4H), 4.08-3.91 (m, 4H), 1.94 (s, 1H); $^{13}$C NMR (300 MHz, CDCl$_3$) δ 177.5, 158.2, 155.2, 144.6, 142.0, 138.2, 132.3, 128.8, 128.7, 128.2, 123.8, 123.3, 121.0, 114.9, 111.5, 109.3, 99.4, 80.1, 69.1, 64.5, 63.9, 61.4, 58.0, 43.6; MS (ES+) m/z 446.0 (M+1).

Example 16

Synthesis of N-methyl-2-{3-[(2'-oxo-5,6-dihydrospiro[benzo[1,2-b:5,4-b']difuran-3,3'-indol]-1'(2'H)-yl)methyl]phenoxy}acetamide

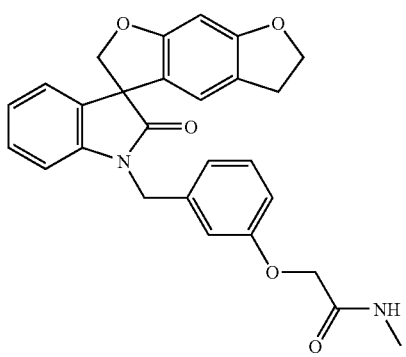

To a stirred solution of {3-[(2'-oxo-5,6-dihydrospiro[benzo[1,2-b:5,4-b']difuran-3,3'-indol]-1'(2'H)-yl)methyl]phenoxy}acetic acid (0.22 g, 0.5 mmol) in dry chloroform (5 mL) was added at ambient temperature oxalyl chloride (0.43 mL, 5.0 mmol) followed by 1 drop of N,N-dimethylformamide. The mixture was stirred at ambient temperature for 2 h and evaporated to dryness in vacuo to afford crude {3-[(2'-oxo-5,6-dihydrospiro[benzo[1,2-b:5,4-b']difuran-3,3'-indol]-1'(2'H)-yl)methyl]phenoxy}acetyl chloride. The crude product was dissolved in dry dichloromethane (5 mL), and used in the next step. To a solution of methylamine hydrochloride (0.07 mg, 1.0 mmol) in dry dichloromethane (5 mL) containing triethylamine (0.35 mL, 2.5 mmol) was added at 0° C. 5.0 mL (0.50 mmol) of the stock solution of {3-[(2'-oxo-5,6-dihydrospiro[benzo[1,2-b:5,4-b']difuran-3,3'-indol]-1'(2'H)-yl)methyl]phenoxy}acetyl chloride. The mixture was stirred at ambient temperature for 16 h, diluted with dichloromethane (20 mL), washed with 7% aqueous solution of citric acid (10 mL), water (10 mL), and brine (10 mL). The organic layer was dried over anhydrous magnesium sulfate, filtered, and concentrated in vacuo. The residue was purified by column chromatography (hexanes/ethyl acetate 1:3) to afford N-methyl-2-{3-[(2'-oxo-5,6-dihydrospiro[benzo[1,2-b:5,4-b']difuran-3,3'-indol]-1'(2'H)-yl)methyl]phenoxy}acetamide (0.09 g, 40%) as a colorless solid: mp 175-176° C.; $^1$H NMR (300 MHz, CDCl$_3$) δ 7.34-7.17 (m, 3H), 7.09-6.98 (m, 2H), 6.90 (s, 1H), 6.87-6.76 (m, 2H), 6.55 (br s, 1H), 6.48 (s, 1H), 6.44 (s, 1H), 5.09-4.96 (m, 2H), 4.88-4.79 (m, 1H), 4.75-4.69 (m, 1H), 4.60-4.51 (m, 2H), 4.47 (s, 2H), 3.11-2.92 (m, 2H), 2.92-2.88 (m, 3H); $^{13}$C NMR (75 MHz, CDCl$_3$) δ 177.9, 168.4, 161.9, 161.3, 157.6, 142.0, 137.9, 132.7, 130.3, 128.7, 123.9, 123.5, 121.0, 120.1, 120.0, 118.8, 113.9, 113.6, 109.1, 93.3, 80.6, 72.4, 67.2, 57.7, 43.9, 29.0, 25.7; MS (ES+) m/z 457.0 (M+1).

Example 17

Synthesis of 1'-[4-(methylsulfinyl)benzyl]-5,6-dihydrospiro[benzo[1,2-b:5,4-b']difuran-3,3'-indol]-2'(1'H)-one

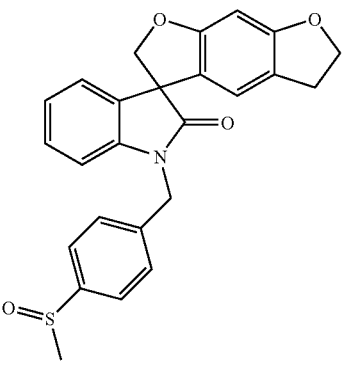

A solution of 1'-(4-(methylthiobenzyl)-5,6-dihydrospiro[benzo[1,2-b:5,4-b']difuran-3,3'-indol]-2'(1'H)-one (0.28 g, 0.67 mmol) and sodium metaperiodate (0.071 g, 0.33 mmol) in water (5 mL) was refluxed for 10 min. The reaction mixture was cooled to ambient temperature, and extracted with ethyl acetate (2×20 mL). The organic layer was concentrated to dryness under reduced pressure, and the residue was subjected to column chromatography eluting with ethyl acetate-hexanes (1:2) to afford 1'-[4-(methylsulfinyl)benzyl]-5,6-dihydrospiro[benzo[1,2-b:5,4-b']difuran-3,3'-indol]-2'(1'H)-one (0.09 g, 30%) as an off-white solid: $^1$H NMR (300 MHz, CDCl$_3$) δ 7.56 (dd, J=39.8, 7.74 Hz, 4H), 7.26-6.72 (m, 4H), 6.45 (s, 1H), 6.41 (s, 1H), 4.99 (ABq, 2H), 4.82 (ABq, 2H), 4.53 (t, J=8.7 Hz, 2H), 3.05-2.92 (m, 2H), 2.70 (s, 3H); $^{13}$C NMR (75 MHz, CDCl$_3$) δ 178.0, 161.9, 161.3, 145.4, 141.7, 139.2, 132.6, 128.8, 128.3, 124.2, 124.1, 123.7, 120.0, 119.9, 118.7, 108.9, 93.3, 80.6, 72.4, 57.7, 43.9, 43.7, 29.0; MS (ES+) m/z: 431.8 (M+1).

Example 18

Synthesis of N-(methylsulfonyl)-N-{2'-oxo-1'-[(2R)-tetrahydrofuran-2-ylmethyl]-1',2'-dihydrospiro[1-benzofuran-3,3'-indol]-6-yl}methanesulfonamide

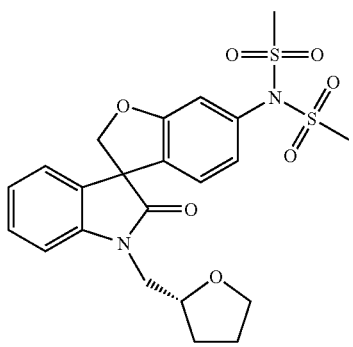

To a stirred solution of 6-amino-1-[(2R)-tetrahydrofuran-2-ylmethyl]spiro[1-benzofuran-3,3'-indol]-2'(1'H)-one (0.15 g, 0.45 mmol), triethylamine (0.09 g, 0.9 mmol) in dichloromethane was added methanesulfonyl chloride (0.13 g, 1.1 mmol). The solution was stirred at ambient temperature for 2 h then concentrated in vacuo to dryness. The residue was purified by flash chromatography with ethyl acetate in hexanes (gradient: 25% to 75%) to afford N-(methylsulfonyl)-N-{2'-oxo-1'-[(2R)-tetrahydrofuran-2-ylmethyl]-1',2'-dihydrospiro[1-benzofuran-3,3'-indol]-6-yl}methanesulfonamide (0.83 g, 37%) as a colorless solid: $^1$H NMR (300 MHz, DMSO-$d_6$, mixture of diastereomers) δ 7.32 (dd, J=7.7, 7.7 Hz, 1H), 7.24-7.14 (m, 3H), 7.02 (dd, J=7.5, 7.5 Hz, 1H), 6.95-6.89 (m, 1H), 6.69 (dd, J=8.0, 2.5 Hz, 1H), 4.94-4.74 (m, 2H), 4.25-4.06 (m, 1H), 3.91-3.39 (m, 11H), 2.03-1.68 (m, 3H), 1.66-1.51 (m, 1H); MS (ES+) m/z 493.1 (M+1).

Example 19

Synthesis of tert-butyl[1-methyl-2-({2'-oxo-1'-[(2R)-tetrahydrofuran-2-ylmethyl]-1',2'-dihydrospiro[1-benzofuran-3,3'-indol]-6-yl}oxy)ethyl]carbamate

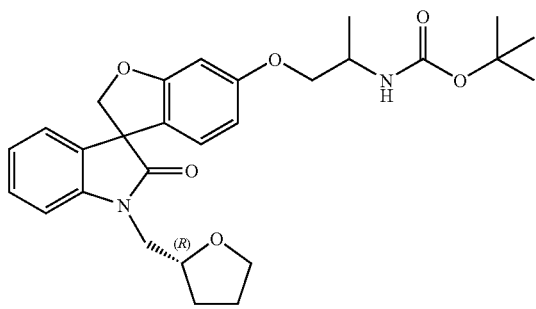

To a stirred solution of triphenylphosphine (0.58 g, 2.22 mmol) in anhydrous tetrahydrofuran (20 mL) at 0° C. under nitrogen were added diisopropyl azodicarboxylate (0.44 mL, 2.22 mmol), (D,L) tert-butyl 1-hydroxypropan-2-ylcarbamate (0.39 g, 2.22 mmol) and 6-hydroxy-1-[(2R)-tetrahydrofuran-2-ylmethyl]spiro[1-benzofuran-3,3'-indol]-2'(1'H)-one (0.30 g, 0.889 mmol). The reaction mixture was stirred at ambient temperature for 16 h, and quenched with ammonium chloride solution. The solvent tetrahydrofuran was removed, and the residue was dissolved in ethyl acetate (100 mL) and was washed with water, brine, then dried over sodium sulfate and filtered. The filtrate was concentrated in vacuo. The residue was purified by flash chromatograph with 25% ethyl acetate in hexanes to yield tert-butyl[1-methyl-2-({2'-oxo-1'-[(2R)-tetrahydrofuran-2-ylmethyl]-1',2'-dihydrospiro[1-benzofuran-3,3'-indol]-6-yl}oxy)ethyl]carbamate (0.14 g, 32%) as a colorless solid: $^1$H NMR (300 MHz, CDCl$_3$) δ 7.33-7.26 (m, 1H), 7.15-6.99 (m, 3H), 6.60 (d, J=8.1 Hz, 1H), 6.52 (d, J=2.1 Hz, 1H), 6.36 (d, J=8.4, 2.4 Hz, 1H), 4.94 (d, J=9.0 Hz, 1H), 4.85-4.69 (m, 1H), 4.68 (d, J=9.0 Hz, 1H), 4.33-4.22 (m, 1H), 4.14-3.66 (m, 7H), 2.10-1.65 (m, 4H), 1.45 (s, 9H), 1.26 (d, J=6.9 Hz, 3H); MS (ES+) m/z 517.2 (M+23).

Example 20

Synthesis of 6-(2-aminopropoxy)-1'-[(2R)-tetrahydrofuran-2-ylmethyl]spiro[1-benzofuran-3,3'-indol]-2'(1'H)-one hydrochloride

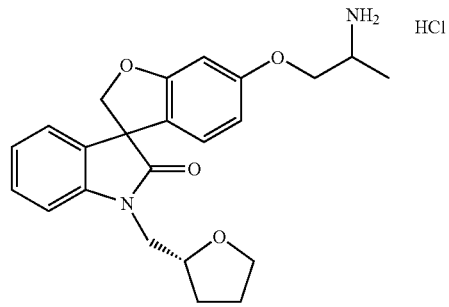

To a solution of tert-butyl[1-methyl-2-({2'-oxo-1'-[(2R)-tetrahydrofuran-2-ylmethyl]-1',2'-dihydrospiro[1-benzofuran-3,3'-indol]-6-yl}oxy)ethyl]carbamate (0.135 g, 0.273 mmol) in dichloromethane (5 mL) was added 4 M HCl in dioxane (2 mL, 8 mmol). The mixture was stirred at ambient temperature for 3 h, followed by the addition of anhydrous ether (20 mL). The white solid was filtered, washed with ether and dried to afford 6-(2-aminopropoxy)-1-[(2R)-tetrahydrofuran-2-ylmethyl]spiro[1-benzofuran-3,3'-indol]-2'(1'H)-one hydrochloride (0.115 g, 99%) as a colorless solid: mp 120-130° C.; $^1$H NMR (300 MHz, CD$_3$OD) δ 7.37-7.04 (m, 4H), 6.67-6.62 (m, 3H), 4.94-4.85 (m, 1H), 4.73 (d, J=9.3 Hz, 1H), 4.36-4.15 (m, 2H), 4.00-3.65 (m, 6H), 2.14-1.68 (m, 4H), 1.40 (d, J=6.6 Hz, 3H); MS (ES+) m/z 395.1 (M+1).

Example 21

Synthesis of 6-[2-(dimethylamino)ethoxy]-1'-[(2R)-tetrahydrofuran-2-ylmethyl]spiro[1-benzofuran-3,3'-indol]-2'(1'H)-one

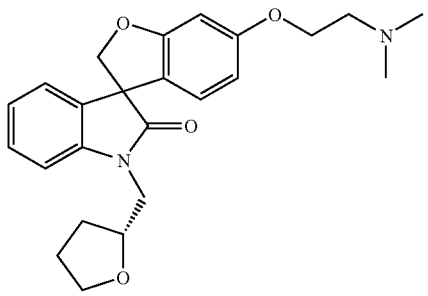

To a stirred solution of 6-[2-(dimethylamino)ethoxy]spiro[1-benzofuran-3,3'-indol]-2'(1'H)-one (0.21 g, 0.64 mmol) in 2-butanone (10 mL) was added (R)-(tetrahydrofuran-2-yl)methyl 4-methylbenzenesulfonate (0.20 g, 0.76 mmol) followed by cesium carbonate (0.63 g, 1.90 mmol) at 0° C. The mixture was stirred at ambient temperature for 16 h. The reaction mixture was filtered and the filtrate was concentrated in vacuo. The residue was subjected to column chromatography (ethyl acetate/methanol/ammonium hydroxide, 10/1/0.2) to give 6-[2-(dimethylamino)ethoxy]-1'-[(2R)-tetrahydrofuran-2-ylmethyl]spiro[1-benzofuran-3,3'-indol]-2'(1'H)-one (0.20 g, 76%): $^1$H NMR (300 MHz, CDCl$_3$) δ 7.31-7.24 (m, 1H), 7.14-6.96 (m, 3H), 6.57 (d, J=8.3 Hz, 1H), 6.52 (d, J=2.2 Hz, 1H), 6.36 (dd, J=8.3, 2.2 Hz, 1H), 4.91 (d, J=9.0 Hz, 1H), 4.66 (d, J=9.0 Hz, 1H), 4.31-4.19 (m, 1H), 4.00 (t, J=5.8 Hz, 2H), 3.94-3.63 (m, 4H), 2.68 (t, J=5.8 Hz, 2H), 2.97 (s, 6H), 2.09-1.63 (m, 4H); $^{13}$C NMR (75 MHz, CDCl$_3$) δ 178.1, 177.9, 162.0, 160.7, 142.9, 142.8, 132.5, 132.4, 128.7, 128.6, 123.7, 123.6, 123.5, 123.4, 123.2, 121.1, 121.0, 109.6, 109.4, 108.1, 97.2, 80.6, 80.5, 68.24, 68.2, 66.3, 58.2, 57.5, 45.9, 44.6, 44.5, 29.2, 28.9, 25.7, 25.5; MS (ES+) m/z 409.3 (M+1).

Example 22

Synthesis of methyl({2'-oxo-1'-[(2R)-tetrahydrofuran-2-ylmethyl]-1',2'-dihydrospiro[1-benzofuran-3,3'-indol]-6-yl}oxy)acetate

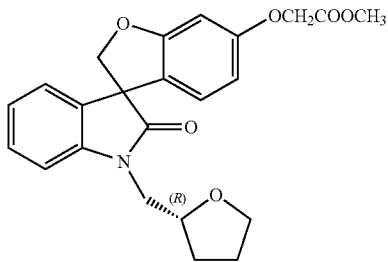

The mixture of 6-hydroxy-1'-[(2R)-tetrahydrofuran-2-ylmethyl]spiro[1-benzofuran-3,3'-indol]-2'(1'H)-one (0.42 g, 1.23 mmol), potassium carbonate (0.22 g, 1.60 mmol) and methyl bromoacetate (0.15 mL, 1.60 mmol) in 2-butanone (10 mL) was refluxed for 15 h. The reaction mixture was concentrated in vacuo to dryness. The residue was purified by flash chromatography with 25% ethyl acetate in hexanes to afford methyl({2'-oxo-1'-[(2R)-tetrahydrofuran-2-ylmethyl]-1',2'-dihydrospiro[1-benzofuran-3,3'-indol]-6-yl}oxy)acetate (0.51 g, 87%) as a colorless solid: $^1$H NMR (300 MHz, CDCl$_3$) δ 7.33-7.26 (m, 1H), 7.15-7.00 (m, 3H), 6.64-6.59 (m, 1H), 6.51 (d, J=2.4 Hz, 1H), 6.36 (dd, J=8.4, 2.4 Hz, 1H), 4.95 (d, J=9.0 Hz, 1H), 4.72 (d, J=9.0 Hz, 1H), 4.59 (s, 2H), 4.32-4.24 (m, 1H), 3.99-3.66 (m, 7H), 2.07-1.84 (m, 3H), 1.78-1.64 (m, 1H); MS (ES+) m/z 409.9 (M+1), 447.9 (M+39).

Example 23

Synthesis of ({2'-oxo-1'-[(2R)-tetrahydrofuran-2-ylmethyl]-1',2'-dihydrospiro[1-benzofuran-3,3'-indol]-6-yl}oxy)acetic acid

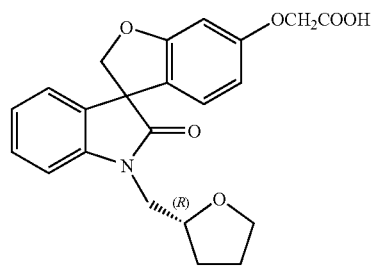

To a solution of methyl({2'-oxo-1'-[(2R)-tetrahydrofuran-2-ylmethyl]-1,2'-dihydrospiro[1-benzofuran-3,3'-indol]-6-yl}oxy)acetate (0.51 g, 1.25 mmol) in tetrahydrofuran (4 mL) and water (1 mL) was added lithium hydroxide (0.05 g, 1.62 mmol). The reaction mixture was stirred at ambient temperature for 16 h. To the reaction mixture was added 1 N HCl to adjust pH<2, then extracted with ethyl acetate (2×50 mL). The combined organic solution was washed with water and brine, then dried over sodium sulfate, filtered and concentrated to afford ({2'-oxo-1'-[(2R)-tetrahydrofuran-2-ylmethyl]-1',2'-dihydrospiro[1-benzofuran-3,3'-indol]-6-yl}oxy)acetic acid (0.42 g, 85%) as a colorless solid: $^1$H NMR (300 MHz, CDCl$_3$) δ 7.33-7.26 (m, 1H), 7.15-7.00 (m, 3H), 6.64 (d, J=8.4 Hz, 1H), 6.54 (d, J=2.4 Hz, 1H), 6.40-6.34 (m, 1H), 4.96 (d, J=9.0 Hz, 1H), 4.70 (d, J=9.0 Hz, 1H), 4.59 (s, 2H), 4.35-4.24 (m, 1H), 3.99-3.68 (m, 4H), 2.10-1.86 (m, 3H), 1.79-1.65 (m, 1H); MS (ES+) m/z 396.0 (M+1), 417.9 (M+23).

Example 24

Synthesis of 1'-[(2R)-tetrahydrofuran-2-ylmethyl]spiro[benzo[1,2-b:5,4-b']difuran-3,3'-indole]-2',5(1'H,6H)-dione 5-oxime

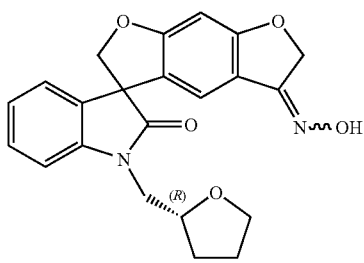

To a solution of 1'-[(2R)-tetrahydrofuran-2-ylmethyl]spiro[benzo[1,2-b:5,4-b']difuran-3,3'-indole]-2',5(1'H,6H)-dione (0.25 g, 0.66 mmol) in methanol (10 mL) and tetrahydrofuran (10 mL) were added hydroxylamine hydrochloride (0.92 g, 13.3 mmol) and sodium acetate (1.09 g, 13.3 mmol). The reaction mixture was stirred for 48 h at ambient temperature. To the reaction mixture was added 1 N sodium hydroxide to adjust pH>9. The mixture was extracted with ethyl acetate (2×50 mL). The combined organic solution was washed with water and brine, then dried over sodium sulfate, filtered and concentrated to afford 1'-[(2R)-tetrahydrofuran-2-ylmethyl]spiro[benzo[1,2-b:5,4-b']difuran-3,3'-indole]-2',5(1'H,6H)-dione 5-oxime (0.25 g, 96%) as a colorless solid: mp 82-100° C.; $^1$H NMR (300 MHz, CDCl$_3$) δ 8.00-7.50 (br, 1H), 7.49-6.83 (m, 5H), 6.52-6.46 (m, 1H), 5.10-4.93 (m, 3H), 4.76-4.69 (m, 1H), 4.30-5.19 (m, 1H), 3.95-3.66 (m, 4H), 2.08-1.60 (m, 4H); MS (ES+) m/z 392.9 (M+1), 414.9 (M+23).

Example 25

Synthesis of (1Z)-N'-hydroxy-2-(2'-oxospiro[furo[2,3-f][1,3]benzodioxole-7,3'-indol]-1'(2'H)-yl)ethanimidamide

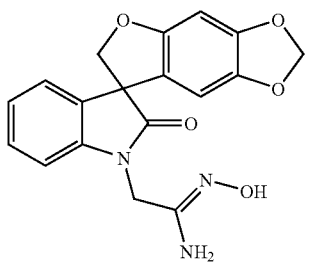

To a mixture of 2'-oxospiro[furo[2,3-f][1,3]benzodioxole-7,3'-indol]-1'(2'H)-yl)acetonitrile (2.00 g, 6.25 mmol) in ethanol (40 mL) and dimethyl sulfoxide (5 mL) was added hydroxylamine (25.0 g, 1.6 mL, 50% wt solution in water). The reaction solution was stirred at ambient temperature for 2 h to form a colourless precipitate. The solid was filtered, washed with water (3×20 mL), and dried to afford (1Z)-N'-hydroxy-2-(2'-oxospiro[furo[2,3-f][1,3]benzodioxole-7,3'-indol]-1'(2'H)-yl)ethanimidamide (1.88 g, 85%) as a colourless solid: mp 235-238° C.; $^1$H NMR (300 MHz, DMSO-d$_6$) δ 9.20 (s, 1H), 7.26 (dd, J=7.7, 7.7 Hz, 1H), 7.10 (d, J=7.3 Hz, 1H), 6.99 (dd, J=8.6, 8.6 Hz, 2H), 6.65 (s, 1H), 6.28 (s, 1H), 5.89 (d, J=1.8 Hz, 2H), 5.49 (s, 2H), 4.70 (ABq, 2H), 4.29 (s, 2H); $^{13}$C NMR (75 MHz, DMSO-d$_6$) δ 177.1, 155.7, 148.7, 147.9, 143.0, 142.1, 132.3, 129.1, 123.7, 123.3, 120.5, 110.0, 103.9, 101.8, 93.6, 80.2, 57.8, 40.3; MS (ES+) m/z 354.18 (M+1), 337.2 (M−17).

Biological Assays

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Guanidine Influx Assay (In Vitro Assay)

This example describes an in vitro assay for testing and profiling test agents against human or rat sodium channels stably expressed in cells of either an endogenous or recombinant origin. The assay is also useful for determining the IC$_{50}$ of a sodium channel blocking compound. The assay is based on the guanidine flux assay described by Reddy, N. L., et al., *J. Med. Chem.* (1998), 41(17):3298-302.

The guanidine influx assay is a radiotracer flux assay used to determine ion flux activity of sodium channels in a high-throughput microplate-based format. The assay uses $^{14}$C-guanidine hydrochloride in combination with various known sodium channel modulators, to assay the potency of test agents. Potency is determined by an IC$_{50}$ calculation. Selectivity is determined by comparing potency of the compound for the channel of interest to its potency against other sodium channels (also called 'selectivity profiling').

Each of the test agents is assayed against cells that express the channels of interest. Voltage gated sodium channels are either TTX sensitive or insensitive. This property is useful when evaluating the activities of a channel of interest when it resides in a mixed population with other sodium channels. The following Table 1 summarizes cell lines useful in screening for a certain channel activity in the presence or absence of TTX.

TABLE 1

| CELL LINE | mRNA Expression | Functional Characterization |
|---|---|---|
| CHO-K1 (Chinese Hamster Ovary; recommended host cell line) ATTC accession number CCL-61 | $Na_v1.4$ expression has been shown by RT-PCR No other $Na_v$ expression has been detected | The 18- to 20-fold increase in [$^{14}$C] guanidine influx was completely blocked using TTX. ($Na_v1.4$ is a TTX sensitive channel) |
| L6 (rat myoblast cell) ATTC Number CRL-1458 | Expression of $Na_v1.4$ and 1.5 | The 10- to 15-fold increase in [$^{14}$C] guanidine influx was only partially blocked by TTX at 100 nM ($Na_v1.5$ is TTX resistant) |
| SH-SY5Y (Human neuroblastoma) ATTC Number CRL-2266 | Published Expression of $Na_v1.9$ and $Na_v1.7$ (Blum et al.) | The 10- to 16-fold increase in [$^{14}$C] guanidine influx above background was partially blocked by TTX ($Na_v1.9$ is TTX resistant) |
| SK-N-BE2C (a human neuroblastoma cell line ATCC Number CRL-2268) | Expression of $Na_v1.8$ | Stimulation of BE2C cells with pyrethroids results in a 6-fold increase in [$^{14}$C] guanidine influx above background. TTX partially blocked influx ($Na_v1.8$ is TTX resistant) |
| PC12 (rat pheochromocytoma) ATTC Number CRL-1721 | Expression of $Na_v1.2$ expression | The 8- to 12-fold increase in [$^{14}$C] guanidine influx was completely blocked using TTX. ($Na_v1.2$ is a TTX sensitive channel) |

It is also possible to employ recombinant cells expressing these sodium channels. Cloning and propagation of recombinant cells are known to those skilled in the art (see, for example, Klugbauer, N, et al., *EMBO J.* (1995), 14(6):1084-90; and Lossin, C., et al., *Neuron* (2002), 34, pp. 877-884).

Cells expressing the channel of interest are grown according to the supplier or in the case of a recombinant cell in the presence of selective growth media such as G418 (Gibco/Invitrogen). The cells are disassociated from the culture dishes with an enzymatic solution (1×) Trypsin/EDTA (Gibco/Invitrogen) and analyzed for density and viability using haemocytometer (Neubauer). Disassociated cells are washed and resuspended in their culture media then plated into Scintiplates (Beckman Coulter Inc.) (approximately 100, 000 cells/well) and incubated at 37° C./5% $CO_2$. for 20-24 hours. After an extensive wash with Low sodium HEPES-buffered saline solution (LNHBSS) (150 mM Choline Chloride, 20 nM HEPES (Sigma), 1 mM Calcium Chloride, 5 mM Potassium Chloride, 1 mM Magnesium Chloride, 10 mM Glucose) agents diluted with LNHBSS are added to each well. (Varying concentrations of test agent may be used). The activation/radiolabel mixture contains aconitine (Sigma) to increase the percentage of time that the sodium channels are open, and $^{14}$C-guanidine hydrochloride (ARC) to measure flux through the voltage-gated sodium channels.

After loading the cells with test agent and activation/radiolabel mixture, the Scintiplates are incubated at ambient temperature. Following the incubation, the Scintplates are extensively washed with LNHBSS supplemented with guanidine (Sigma). The Scintiplates are dried and then counted using a Wallac MicroBeta TriLux (Perkin-Elmer Life Sciences). The ability of the test agent to block sodium channel activity is determined by comparing the amount of $^{14}$C-guanidine present inside the cells expressing the different sodium channels. Based on this data, a variety of calculations, as set out elsewhere in this specification, may be used to determine whether a test agent is selective for a particular sodium channel.

The $IC_{50}$ value of a test agent for a specific sodium channel may be determined using the above general method. The $IC_{50}$ may be determined using a 3, 8, 10, 12 or 16 point curve in duplicate or triplicate with a starting concentration of 1, 5 or 10 μM diluted serially with a final concentration reaching the sub-nanomolar, nanomolar and low micromolar ranges. Typically the mid-point concentration of test agent is set at 1 μM, and sequential concentrations of half dilutions greater or smaller are applied (e.g. 0.5 μM; 5 μM and 0.25 μM; 10 μM and 0.125 μM; 20 μM etc.). The $IC_{50}$ curve is calculated using the 4 Parameter Logistic Model or Sigmoidal Dose-Response Model formula (fit=$(A+((B-A)/(1+((C/x)^D))))$.

The fold selectivity, factor of selectivity or multiple of selectivity, is calculated by dividing the $IC_{50}$ value of the test sodium channel by the reference sodium channel, for example, $Na_v1.5$.

Representative compounds of the invention, when tested in the above assay using a known cell line that expresses a sodium channel, demonstrated an $IC_{50}$ (nM) activity level as set forth below in Table 2 wherein "A" refers to an $IC_{50}$ activity level of from 1 nM to 100 nM, "B" refers to an $IC_{50}$ activity level from 100 nM to 1 μM, "C" refers to an $IC_{50}$ activity level from 1 μM to 10 μM, and "D" refers to an $IC_{50}$ activity level equal to or greater than 10 μM. The Synthetic Example numbers provided in Table 2 correspond to the Synthetic Examples herein:

TABLE 2

| Ex. # | Compound Name | $IC_{50}$ Activity Level |
|---|---|---|
| 2 | 6-[2-(dimethylamino)ethoxy]spiro[1-benzofuran-3,3'-indol]-2'(1'H)-one | D |
| 4 | 1'-[(2R)-tetrahydrofuran-2-ylmethyl]-6-{[tris(1-methylethyl)silyl]oxy}spiro[1-benzofuran-3,3'-indol]-2'(1'H)-one | B |
| 8 | 1'-{[(2S)-1-acetylpyrrolidin-2-yl]methyl}-5,6-dihydrospiro[benzo[1,2-b:5,4-b']difuran-3,3'-indol]-2'(1'H)-one | C |

TABLE 2-continued

| Ex. # | Compound Name | IC$_{50}$ Activity Level |
|---|---|---|
| 11 | 2-(4'-chloro-2'-oxospiro[furo[2,3-f][1,3]benzodioxole-7,3'-indol]-1'(2'H)-yl)-N'-[(cyclopropylcarbonyl)oxy]ethanimidamide | B |
| 13 | 2-{3-[(2-oxo-5,6-dihydrospiro[benzo[1,2-b:5,4-b']difuran-3,3'-indol]-1(2H)-yl)methyl]phenoxy}acetamide | A |
| 13.1 | 2-{4-[(2'-oxo-5,6-dihydrospiro[benzo[1,2-b:5,4-b']difuran-3,3'-indol]-1'(2'H)-yl)methyl]phenoxy}acetamide | A |
| 13.2 | 2-{4-[(2'-oxo-2,3-dihydrospiro[furo[2,3-g][1,4]benzodioxine-8,3'-indol]-1'(2'H)-yl)methyl]phenoxy}acetamide | A |
| 13.3 | 1'-[4-(2-methoxyethoxy)benzyl]-2,3-dihydrospiro[furo[2,3-g][1,4]benzodioxine-8,3'-indol]-2'(1'H)-one | A |
| 13.4 | 1'-{4-[2-(dimethylamino)ethoxy]benzyl}-2,3-dihydrospiro[furo[2,3-g][1,4]benzodioxine-8,3'-indol]-2'(1'H)-one | B |
| 14 | ethyl {3-[(2'-oxo-5,6-dihydrospiro[benzo[1,2-b:5,4-b']difuran-3,3'-indol]-1'(2'H)-yl)methyl]phenoxy}acetate | B |
| 14.1 | ethyl {4-[(2'-oxo-5,6-dihydrospiro[benzo[1,2-b:5,4-b']difuran-3,3'-indol]-1'(2'H)-yl)methyl]phenoxy}acetate | A |
| 14.2 | ethyl {4-[(2'-oxo-2,3-dihydrospiro[furo[2,3-g][1,4]benzodioxine-8,3'-indol]-1'(2'H)-yl)methyl]phenoxy}acetate | A |
| 15 | {3-[(2'-oxo-5,6-dihydrospiro[benzo[1,2-b:5,4-b']difuran-3,3'-indol]-1'(2'H)-yl)methyl]phenoxy}acetic acid | C |
| 16 | N-methyl-2-{3-[(2'-oxo-5,6-dihydrospiro[benzo[1,2-b:5,4-b']difuran-3,3'-indol]-1'(2'H)-yl)methyl]phenoxy}acetamide | A |
| 17 | 1'-[4-(methylsulfinyl)benzyl]-5,6-dihydrospiro[benzo[1,2-b:5,4-b']difuran-3,3'-indol]-2'(1'H)-one | B |
| 18 | N-(methylsulfonyl)-N-{2'-oxo-1'-[(2R)-tetrahydrofuran-2-ylmethyl]-1',2'-dihydrospiro[1-benzofuran-3,3'-indol]-6-yl}methanesulfonamide | C |
| 20 | 6-(2-aminopropoxy)-1'-[(2R)-tetrahydrofuran-2-ylmethyl]spiro[1-benzofuran-3,3'-indol]-2'(1'H)-one hydrochloride | C |
| 21 | 6-[2-(dimethylamino)ethoxy]-1'-[(2R)-tetrahydrofuran-2-ylmethyl]spiro[1-benzofuran-3,3'-indol]-2'(1'H)-one | C |
| 24 | 1'-[(2R)-tetrahydrofuran-2-ylmethyl]spiro[benzo[1,2-b:5,4-b']difuran-3,3'-indole]-2',5(1'H,6H)-dione 5-oxime | C |
| 25 | (1Z)-N'-hydroxy-2-(2'-oxospiro[furo[2,3-f][1,3]benzodioxole-7,3'-indol]-1'(2'H)-yl)ethanimidamide | B |

Biological Example 2

Electrophysiological Assay (In Vitro Assay)

Cells expressing the channel of interest are cultured in DMEM growth media (Gibco) with 0.5 mg/mL G418, +/−1% PSG, and 10% heat-inactivated fetal bovine serum at 37° C. and 5% $CO_2$. For electrophysiological recordings, cells are plated on 10 mm dishes.

Whole cell recordings are examined by established methods of whole cell voltage clamp (Bean et al., op. cit.) using an Axopatch 200B amplifier and Clampex software (Axon Instruments, Union City, Calif.). All experiments are performed at ambient temperature. Electrodes are fire-polished to resistances of 2-4 Mohms Voltage errors and capacitance artifacts are minimized by series resistance compensation and capacitance compensation, respectively. Data are acquired at 40 kHz and filtered at 5 kHz. The external (bath) solution consists of: NaCl (140 mM), KCl (5 mM), $CaCl_2$ (2 mM), $MgCl_2$ (1 mM), HEPES (10 mM) at pH 7.4. The internal (pipette) solution consists of (in mM): NaCl (5), $CaCl_2$ (0.1), $MgCl_2$ (2), CsCl (10), CsF (120), HEPES (10), EGTA (10), at pH 7.2.

To estimate the steady-state affinity of compounds for the resting and inactivated state of the channel ($K_r$ and $K_i$, respectively), 12.5 ms test pulses to depolarizing voltages from −60 to +90 mV from a holding potential of −120 mV is used to construct current-voltage relationships (I-V curves). A voltage near the peak of the IV-curve (−30 to 0 mV) is used as the test pulse throughout the remainder of the experiment. Steady-state inactivation (availability) curves are then constructed by measuring the current activated during a 8.75 ms test pulse following 1 second conditioning pulses to potentials ranging from −120 to −10 mV.

The steady-state voltage-dependence of binding of a compound to a sodium channel is determined by measuring the blockage of the ionic current at two holding potentials. Binding to rested-state channels is determined by using a holding potential of −120 mV, so that maximal availability is achieved. Binding to inactivated-state channels is evaluated at a holding potential such that only 10% of the channels are available to open. The membrane potential is held at this voltage for at least 10 seconds so that drug binding can equilibrate.

The apparent dissociation constant at each voltage is calculated with the equation:

$$\% \text{ inhibition} = \frac{[\text{Drug}]}{([\text{Drug}] + K_d)}$$

where $K_d$ is the dissociation constant (either $K_r$ or $K_i$), and [Drug] is the concentration of the test compound.

Representative compounds of the invention, when tested in this model, demonstrated affinities for the inactivated state of the channel of interest as set forth below in Table 3 wherein "A" refers to $K_i$ of less than 300 nM and "B" refers to $K_i$ of greater than 300 nM. The Example numbers provided in Table 3 correspond to the Examples herein:

TABLE 3

| Ex. No. | Compound Name | $K_i$ (μM) |
|---|---|---|
| 13.2 | 2-{4-[(2'-oxo-2,3-dihydrospiro[furo[2,3-g][1,4]benzodioxine-8,3'-indol]-1'(2'H)-yl)methyl]phenoxy}acetamide | B |
| 13.4 | 1'-{4-[2-(dimethylamino)ethoxy]benzyl}-2,3-dihydrospiro[furo[2,3-g][1,4]benzodioxine-8,3'-indol]-2'(1'H)-one | A |
| 14 | ethyl {3-[(2'-oxo-5,6-dihydrospiro[benzo[1,2-b:5,4-b']difuran-3,3'-indol]-1'(2'H)-yl)methyl]phenoxy}acetate | B |
| 15.3 | 1'-[4-(2-hydroxyethoxy)benzyl]-2,3-dihydrospiro[furo[2,3-g][1,4]benzodioxine-8,3'-indol]-2'(1'H)-one | B |

Biological Example 3

Analgesia Induced by Sodium Channel Blockers

Heat Induced Tail Flick Latency Test

In this test, the analgesia effect produced by administering a compound of the invention can be observed through heat-induced tail-flick in mice. The test includes a heat source consisting of a projector lamp with a light beam focused and directed to a point on the tail of a mouse being tested. The tail-flick latencies, which are assessed prior to drug treatment, and in response to a noxious heat stimulus, i.e., the response time from applying radiant heat on the dorsal surface of the tail to the occurrence of tail flick, are measured and recorded at 40, 80, 120, and 160 minutes.

For the first part of this study, 65 animals undergo assessment of baseline tail flick latency once a day over two consecutive days. These animals are then randomly assigned to one of the 11 different treatment groups including a vehicle control, a morphine control, and 9 compounds at 30 mg/Kg are administered intramuscularly. Following dose administration, the animals are closely monitored for signs of toxicity including tremor or seizure, hyperactivity, shallow, rapid or depressed breathing and failure to groom. The optimal incubation time for each compound is determined via regression analysis. The analgesic activity of the test compounds is expressed as a percentage of the maximum possible effect (% MPE) and is calculated using the following formula:

$$\% MPE \frac{\text{Postdrug latency} - \text{Predrug latency}}{\text{Cut-off time (10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals are briefly habituated to the plexiglass test chamber on the day prior to experimental day for 20 minutes. On the test day, animals are randomly injected with the test articles. At 30 minutes after drug administration, 50 μL of 10% formalin is injected subcutaneously into the plantar surface of the left hind paw of the rats. Video data acquisition begins immediately after formalin administration, for duration of 90 minutes.

The images are captured using the Actimetrix Limelight software which stores files under the *.IIii extension, and then converts it into the MPEG-4 coding. The videos are then analyzed using behaviour analysis software "The Observer 5.1", (Version 5.0, Noldus Information Technology, Wageningen, The Netherlands). The video analysis is conducted by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs is calculated by a series of steps, where the first is to sum the length of non-normal behaviours (behaviours 1, 2, 3) of each animal. A single value for the vehicle group is obtained by averaging all scores within the vehicle treatment group. The following calculation yields the MPIE value for each animal:

MPIE (%)=100−[(treatment sum/average vehicle value)×100%]

The pain score is calculated from a weighted scale as described above. The duration of the behaviour is multiplied by the weight (rating of the severity of the response), and divided by the total length of observation to determine a pain rating for each animal. The calculation is represented by the following formula:

Pain rating=[0($T_0$)+1($T_1$)+2($T_2$)+3($T_3$)]/($T_0$+$T_1$+$T_2$+$T_3$)

CFA Induced Chronic Inflammatory Pain

In this test, tactile allodynia is assessed with calibrated von Frey filaments. Following a full week of acclimatization to the vivarium facility, 150 μL of the "Complete Freund's Adjuvant" (CFA) emulsion (CFA suspended in an oil/saline (1:1) emulsion at a concentration of 0.5 mg/mL) is injected subcutaneously into the plantar surface of the left hind paw of rats under light isoflurane anaesthesia. Animals are allowed to recover from the anaesthesia and the baseline thermal and mechanical nociceptive thresholds of all animals are assessed one week after the administration of CFA. All animals are habituated to the experimental equipment for 20 minutes on the day prior to the start of the experiment. The test and control articles are administrated to the animals, and the nociceptive thresholds measured at defined time points after drug administration to determine the analgesic responses to each of the six available treatments. The time points used are previously determined to show the highest analgesic effect for each test compound.

Thermal nociceptive thresholds of the animals are assessed using the Hargreaves test. Animals are placed in a Plexiglas enclosure set on top of an elevated glass platform with heating units. The glass platform is thermostatically controlled at a temperature of approximately 30° C. for all test trials. Animals are allowed to accommodate for 20 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 45 respectively, and a cut off time of 20 seconds is employed to prevent tissue damage.

The response thresholds of animals to tactile stimuli are measured using the Model 2290 Electrovonfrey anesthesiometer (IITC Life Science, Woodland Hills, Calif.) following the Hargreaves test. Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Postoperative Models of Nociception

In this model, the hypealgesia caused by an intra-planar incision in the paw is measured by applying increased tactile stimuli to the paw until the animal withdraws its paw from the applied stimuli. While animals are anaesthetized under 3.5% isofluorane, which is delivered via a nose cone, a 1 cm longitudinal incision is made using a number 10 scalpel blade in the plantar aspect of the left hind paw through the skin and fascia, starting 0.5 cm from the proximal edge of the heel and extending towards the toes. Following the incision, the skin is apposed using 2, 3-0 sterilized silk sutures. The injured site is covered with Polysporin and Betadine. Animals are returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals are placed in an elevated Plexiglas enclosure set on a mire mesh surface. After at least 10 minutes of acclimatization, pre-calibrated Von Frey hairs are applied perpendicularly to the plantar surface of both paws of the animals in an ascending order starting from the 10 g hair, with sufficient force to cause slight buckling of the hair against the paw. Testing continues until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Neuropathic Pain Model; Chronic Constriction Injury

Briefly, an approximately 3 cm incision is made through the skin and the fascia at the mid thigh level of the animals' left hind leg using a no. 10 scalpel blade. The left sciatic nerve is exposed via blunt dissection through the biceps femoris with care to minimize haemorrhagia. Four loose ligatures are tied along the sciatic nerve using 4-0 non-degradable sterilized silk sutures at intervals of 1 to 2 mm apart. The tension of the loose ligatures is tight enough to induce slight constriction of the sciatic nerve when viewed under a dissection microscope at a magnification of 4 fold. In the sham-operated animal, the left sciatic nerve is exposed without further manipulation. Antibacterial ointment is applied directly into the wound, and the muscle is closed using sterilized sutures. Betadine is applied onto the muscle and its surroundings, followed by skin closure with surgical clips.

The response thresholds of animals to tactile stimuli are measured using the Model 2290 Electrovonfrey anesthesiometer (IITC Life Science, Woodland Hills, Calif.). Animals are placed in an elevated Plexiglas enclosure set on a mire mesh surface. After 10 minutes of accommodation, pre-calibrated Von Frey hairs are applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus.

Thermal nociceptive thresholds of the animals are assessed using the Hargreaves test. Following the measurement of tactile thresholds, animals are placed in a Plexiglass enclosure set on top of an elevated glass platform with heating units. The glass platform is thermostatically controlled at a temperature of approximately 24 to 26° C. for all test trials. Animals are allowed to accommodate for 10 minutes following placement into the enclosure until all exploration behaviour ceases. The Model 226 Plantar/Tail Stimulator Analgesia Meter (IITC, Woodland Hills, Calif.) is used to apply a radiant heat beam from underneath the glass platform to the plantar surface of the hind paws. During all test trials, the idle intensity and active intensity of the heat source are set at 1 and 55 respectively, and a cut off time of 20 seconds is used to prevent tissue damage.

Neuropathic Pain Model: Spinal Nerve Ligation

The spinal nerve ligation (SNL) neuropathic pain model is used as an animal (i.e. rat) model of neuropathic pain. In the SNL test, the lumbar roots of spinal nerves L5 and L6 are tightly ligated to cause nerve injury, which results in the development of mechanical hyperalgesia, mechanical allodynia and thermal hypersensitivity. The surgery is performed two weeks before the test day in order for the pain state to fully develop in the animals. Several spinal nerve ligation variations are used to characterize the analgesic properties of a compound of the invention.

(1) Ligation of the L5 spinal nerve;
(2) Ligation of the L5 and L6 spinal nerves;
(3) Ligation and transection of the L5 spinal nerve;
(4) Ligation and transection of the L5 and L6 spinal nerves; or
(5) Mild irritation of the L4 spinal nerve in combination with any one of the above (1)-(4).

While the animals are anaesthetized under 3.5% isofluorane delivered via a nose cone, an approximately 2.5 cm longitudinal incision is made using a number 10 scalpel blade in the skin just lateral to the dorsal midline, using the level of the posterior iliac crests as the midpoint of the incision. Following the incision, the isoflorane is readjusted to maintenance levels (1.5%±2.5%). At mid-sacral region, an incision is made with the scalpel blade, sliding the blade along the side of the vertebral column (in the saggital plane) until the blade hits the sacrum. Scissors tips are introduced through the incision and the muscle and ligaments are removed from the spine to expose 2-3 cm of the vertebral column. The muscle and fascia are cleared from the spinal vertebra in order to locate the point where the nerve exits from the vertebra. A small glass hook is placed medial to the spinal nerves and the spinal nerves are gently elevated from the surrounding tissues. Once the spinal nerves have been isolated, a small length of non-degradable 6-0 sterilized silk thread is wound twice around the ball at the tip of the glass hook and passed back under the nerve. The spinal nerves are then firmly ligated by tying a knot, ensuring that the nerve bulges on both sides of the ligature. The procedure may be repeated as needed. In some animals, the L4 spinal nerve may be lightly rubbed (up to 20 times) with the small glass hook to maximize the development of neuropathic pain. Antibacterial ointment is applied directly into the incision, and the muscle is closed using sterilized sutures. Betadine is applied onto the muscle and its surroundings, followed by skin closure with surgical staples or sterile non-absorbable monofilament 5-0 nylon sutures.

The analgesic effect produced by topical administration of a compound of the invention to the animals can then be observed by measuring the paw withdrawal threshold of animals to mechanical tactile stimuli. These may be measured using either the mechanical allodynia procedure or the mechanical hyperalgesia procedure as described below. After establishment of the appropriate baseline measurements by either method, topical formulation of a compound of the invention is applied on the ipsilateral ankle and foot. The animals are then placed in plastic tunnels for 15 minutes to prevent them from licking the treated area and removing the compound. Animals are placed in the acrylic enclosure for 15 minutes before testing the ipsilateral paw by either of the methods described below, and the responses are recorded at 0.5, 1.0 and 2.0 hour post treatment.

A. Mechanical Allodynia Method

The pain threshold of animals to mechanical alloydnia for both operated and control animals can be measured approximately 14 days post-surgery using manual calibrated von Frey filaments as follows. Animals are placed in an elevated plexiglass enclosure set on a mire mesh surface. Animals are allowed to acclimate for 20-30 minutes. Pre-calibrated Von Frey hairs are applied perpendicularly to the plantar surface of the ipsilateral paw of the animals starting from the 2.0 g hair, with sufficient force to cause slight buckling of the hair against the paw to establish the baseline measurements. Stimuli are presented in a consecutive manner, either in an ascending or descending order until the first change in response is noted, after which four additional responses are recorded for a total of six responses. The six responses measured in grams are entered into a formula as described by Chaplan, S. R. et al., *J. Neurosci. Methods,* 1994 July; 53(1): 55-63, and a 50% withdrawal threshold is calculated. This constitutes the mechanical allodynia value.

B. Mechanical Hyperalgesia Method

The response thresholds of animals to tactile stimuli were measured using the Model 2290 Electrovonfrey anesthesiometer (IITC Life Science, Woodland Hills, Calif.). Animals were placed in an elevated Plexiglas enclosure set on a wire mesh surface. After 15 minutes of accommodation in this enclosure, a von Frey hair was applied perpendicularly to the plantar surface of the ipsilateral hind paws of the animals, with sufficient force, measured in grams, to elicit a crisp response of the paw. The response indicated a withdrawal from the painful stimulus and constituted the efficacy endpoint. The data were expressed as percent change from baseline threshold measured in grams.

Biological Example 4

Aconitine Induced Arrhythmia Test

The antiarrhythmic activity of compounds of the invention is demonstrated by the following test. Arrhythmia is provoked by intravenous administration of aconitine (2.0 µg/Kg) dissolved in physiological saline solution. Test compounds of the invention are intravenously administered 5 minutes after the administration of aconitine. Evaluation of the anti-arrhythmic activity is conducted by measuring the time from the aconitine administration to the occurrence of extrasystole (ES) and the time from the aconitine administration to the occurrence of ventricular tachycardia (VT).

In rates under isoflurane anaesthesia (¼ to ⅓ of 2%), a tracheotomy is performed by first creating an incision in the neck area, then isolating the trachea and making a 2 mm incision to insert tracheal tube 2 cm into the trachea such that the opening of the tube is positioned just on top of the mouth. The tubing is secured with sutures and attached to a ventilator for the duration of the experiment.

Incisions (2.5 cm) are then made into the femoral areas and using a blunt dissection probe, the femoral vessels are isolated. Both femoral veins are cannulated, one for pentobarbital anaesthetic maintenance (0.02-0.05 mL) and one for the infusion and injection of drug and vehicle. The femoral artery is cannulated with the blood pressure gel catheter of the transmitter.

The ECG leads are attached to the thoracic muscle in the Lead II position (upper right/above heart—white lead and lower left/below heart—red lead). The leads are secured with sutures.

All surgical areas are covered with gauze moistened with 0.9% saline. Saline (1-1.5 mL of a 0.9% solution) is supplied to moisten the areas post-surgery. The animals' ECG and ventilation are allowed to equilibrate for at least 30 minutes.

The arrhythmia is induced with a 2 µg/Kg/min aconitine infusion for 5 minutes. During this time the ECG is recorded and continuously monitored. Compounds of the present invention can be tested in these assays to determine their effectiveness in treating arrhythmia.

Biological Example 5

Ischemia Induced Arrhythmia Test

Rodent models of ventricular arrhythmias, in both acute cardioversion and prevention paradigms have been employed in testing potential therapeutics for both atrial and ventricular arrhythmias in humans. Cardiac ischemia leading to myocardial infarction is a common cause of morbidity and mortality. The ability of a compound to prevent ischemia-induced ventricular tachycardia and fibrillation is an accepted model for determining the efficacy of a compound in a clinical setting for both atrial and ventricular tachycardia and fibrillation.

Anaesthesia is first induced by pentobarbital (i.p.), and maintained by an i.v. bolus infusion. Male SD rats have their trachea cannulated for artificial ventilation with room air at a stroke volume of 10 mL/Kg, 60 strokes/minute. The right femoral artery and vein are cannulated with PE50 tubing for mean arterial blood pressure (MAP) recording and intravenous administration of compounds, respectively.

The chest is opened between the $4^{th}$ and $5^{th}$ ribs to create a 1.5 cm opening such that the heart is visible. Each rat is placed on a notched platform and metal restraints are hooked onto the rib cage opening the chest cavity. A suture needle is used to penetrate the ventricle just under the lifted atrium and exited the ventricle in a downward diagonal direction so that a >30% to <50% occlusion zone (OZ) would be obtained. The exit position is ~0.5 cm below where the aorta connects to the left ventricle. The suture is tightened such that a loose loop (occluder) is formed around a branch of the artery. The chest is then closed with the end of the occluder accessible outside of the chest.

Electrodes are placed in the Lead II position (right atrium to apex) for ECG measurement as follows: one electrode inserted into the right forepaw and the other electrode inserted into the left hind paw.

The body temperature, MAP, ECG, and heart rate are constantly recorded throughout the experiment. Once the critical parameters has stabilized, a 1-2 minute recording is taken to establish the baseline values. Infusion of a compound of the invention or control substance is initiated once baseline values are established. After a 5-minute infusion of compound or control, the suture is pulled tight to ligate the LCA and create ischemia in the left ventricle. The critical parameters are recorded continuously for 20 minutes after ligation, unless the MAP reached the critical level of 20-30 mmHg for at least 3 minutes, in which case the recording is stopped because the animal would be declared deceased and is then sacrificed. The ability of compounds of the invention to prevent arrhythmias and sustain near-normal MAP and HR is scored and compared to control.

Biological Example 6

In Vivo Assay for Benign Prostate Hyperplasia (BPH)

The effectiveness of the compounds of the present invention for treating BPH can be demonstrated by the following in vivo assay.

Dogs are dosed orally with compounds of the present invention at oral doses of between 0 mg/Kg and 100 mg/Kg for a period of 4 weeks. A control group receives placebo. The animals are sacrificed and the prostate glands dissected out, dabbed dry and then weighed.

Biological Example 7

In Vivo Assay for Antihypercholesterlemia Efficacy and Antiatherosclerotic Efficacy Dogs have cardiovascular systems similar to that of humans, making them ideal for studying the effects of medicinal compounds designed to treat cardiovascular disorders.

Dogs are dosed orally at a range of 0 mg/Kg to 100 mg/Kg daily with compounds of the present invention for a period of 2-4 weeks. After 2 and 4 weeks the animals are bled and their serum collected for total cholesterol analysis and compared to the animals dosed with vehicle alone (0 mg/Kg).

The measurement of cholesterol is one of the most common tests performed in the clinical laboratory setting. Simple fluorometric methods for the sensitive quantitation of total cholesterol in plasma or serum are commonly used. In one assay, cholesteryl esters in the sample are first hydrolyzed by cholesterol esterase. All cholesterol, whether previously esterified or existing free in the circulation, is then oxidized by cholesterol oxidase to the corresponding ketone and hydrogen peroxide. ADHP (10-acetyl-3,7-dihydroxyphenoxazine) is utilized as a highly sensitive and stable probe for hydrogen peroxide. Horseradish peroxidase catalyzes the reaction of ADHP with hydrogen peroxide to yield the highly fluorescent product resorufin, which can be monitored using excitation wavelengths of 565-580 nm and emission wavelengths of 585-595 nm.

Biological Example 8

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/mL, 50 µL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

Biological Example 9

Cytochrome P450 (CYP450) Inhibition Assay

CYP450 (CYP) is the designation for a superfamily of enzymes. Each family consists of one or more subfamilies and each subfamily contains one or more specific CYP isoforms. The Cytochrome P450 (CYP450) Inhibition Assay is a fluorescence-based assay using a CYP isozyme for screening of compounds of the invention to determine the level of CYP inhibition by a specific compound. The assay is based on the CYP inhibition kit described by Vivid CYP450 Screening Kit Protocol, 2005, Invitrogen Corporation (Invitrogen Corporation, 1600 Faraday Avenue, Carlsbad, Calif. 92008, USA).

This assay is designed to assess compounds by quantifying the inhibition of the predominant human CYP isozymes involved in hepatic drug metabolism. It is based on the principle derived from the testing of many pharmacologically active compounds for their ability to serve as substrates and inhibitors for the major Drug Metabolizing Enzymes, primarily CYPs, or for their interference with the metabolism of existing drugs. The standard method for evaluating specific CYP isozyme inhibition is to determine the conversion of a probe substrate (Table 4) into its metabolite, in the presence and absence of the potential inhibitor. Quantification of the metabolite is achieved by HPLC or by using a probe substrate that is metabolized into a fluorescent product (fluorescent assay).

Four CYP isozymes were investigated: CYP3A4, 2C9, 2C19 and 2D6. In particular, CYP3A4 is shown to be one of the most important isozyme involved in the metabolism of drugs in the body (see http://medicine.iupui.edu/flockhart/table.htm). A drug that inhibits a specific CYP isozyme may decrease the metabolism of the drug and increase serum concentrations of drugs that are substrates for that isoenzyme. The CYP3A4 data reported below can be useful to predict potential clinical drug-drug interactions for a particular compound.

TABLE 4

CYP450 ISOZYMES (CYP) AND SUBSTRATES USED

| CYP | Substrate Acronym | Structure Name |
| --- | --- | --- |
| 3A4 | BOMCC | 7-(benzyloxymethoxy)-3-cyanocoumarin |
| 2C19 | EOMCC | 7-(ethoxymethoxy)-3-cyanocoumarin |
| 2C9 | BOMF | (benzyloxymethoxy)fluorescein |
| 2D6 | MOBFC | 7-(4-methoxybenzyloxy)-4-trifluoromethylcoumarin |

TABLE 5

CYP450 ISOZYME INHIBITORS

| Isozyme | Inhibitor | Concentration in 10 μM assay | % Inhibition in 10 μM assay | $IC_{50}$ (nM) |
|---|---|---|---|---|
| 3A4 | Ketoconazole | 0.1 μM | 50 +/− 10% | 88 +/− 30 nM |
| 2C9 | Sulfaphenazole | 0.420 μM | 50 +/− 15% | 345 +/− 20 nM |
| 2C19 | Ketoconazole | 7.62 μM | 65 +/− 10% | 3132 +/− 680 nM |
| 2D6 | Quinidine | 0.0137 μM | 55 +/− 15% | 15 +/− 5 nM |

TABLE 6

TERMINOLOGY

| Name | Definition |
|---|---|
| Regeneration System (RS) | 100x consists of 333 mM Glucose-6-phosphate and 40 U/mL Glucose-6-phosphate dehydrogenase in 100 mM Potassium Phosphate Buffer (pH 8.0). |
| Baculosomes (Bac) | Microsomes prepared from insect cells that were infected with baculovirus containing the cDNAs for human CYP isozyme (1 μM specific P450 content) and rabbit NADPH reductase. |
| $NADP^+$ | Nicotinamide adenine dinucleotide phosphate at 10 μM in potassium phosphate buffer (100 mM, pH 8.0). Conversion of NADP+ into NADPH by the regeneration system is required to start the CYP450 reaction. |
| Reaction Buffer | Contains 100 or 200 mM potassium phosphate buffer. |
| Pre-Mix | Contains reaction buffer, RS, Bac. Prepare separately for each isozyme. |
| Substrate Mix | Contains reaction buffer, substrate (BOMCC, EOMCC, BOMF, or MOBFC), and NADP+. Prepare separately for each isozyme. |

This assay can be used for single concentration screening or for $IC_{50}$ determination. In a single concentration screening assay, the final assay concentration of the test compound is 10 μM. In an $IC_{50}$ determination assay, $IC_{50}$ may be determined using a 3, 6, or 12 point curve in triplicate with a chosen starting concentration diluted serially.

Preparation Stage:

In the Preparation Stage, the test compounds, controls (acetonitrile (ACN) or dimethyl sulfoxide (DMSO) and No Baculosomes), and known inhibitors (Table 5) were diluted to 10% ACN or DMSO in water at appropriate concentrations. The Premix and Substrate Mix solutions were also prepared per kit instructions. The Premix consisted of P450 Baculosomes, regeneration system (RS), and Vivid® CYP450 reaction buffer. The Substrate Mix consisted of Vivid® substrate, NADP+ and Vivid® CYP450 reaction buffer.

Assay Stage:

In the Assay Stage, 30 μL water was added to each well of a 96-well assay plate. Then 10 μL of the 10% ACN or DMSO in water stocks of the test compounds, negative controls, or known inhibitors were added to designated wells according to the assay plate layout. The third step was to add 50 μL of the Premix solution to each working well (except for No Baculosomes control wells, 50 μL buffer was added instead). The assay plate was then pre-warmed at ambient temperature in the dark for 20 minutes. When pre-warming was completed, 10 μL of the Substrate Mix solution was added to each working well (including the No Baculosomes control wells). This resulted in a final 1% ACN or DMSO concentration. The assay plate was immediately placed in a PolarStar plate reader to read initial fluorescence. The assay plate was again incubated at ambient temperature in the dark for 20, 30, or 60 minutes, depending on the reaction time of the isozyme (Table 7). 10 μL of the stop reagent was added to each working well and final fluorescence was read.

TABLE 7

ISOZYME REACTION TIME AND STOP REAGENT

| Isozyme | Reaction Time (min) | Concentration of Stop Reagent |
|---|---|---|
| 3A4 | 20 | 10 μM Ketoconazole |
| 2C19 | 20 | 30 μM Ketoconazole |
| 2C9 | 30 | 10 μM Sulfaphenazole |
| 2D6 | 60 | 1 μM Quinidine |

Data Analysis:

The difference between the initial and final fluorescence readings was used to calculate percent inhibition. The ACN or DMSO readings represented 0% inhibition and the No Baculosomes readings represented 100% inhibition. Percent inhibition by the compound or known inhibitor was calculated based on comparison with the solvent (ACN or DMSO) control and the No Baculosomes control. To minimize any fluorescence compound or background effect, the relative fluorescence unit (RFU) initial was subtracted from the RFU final.

Determine the % inhibition for each compound or control for each CYP450 isozyme:

$$\% \text{ Inhibition} = \frac{\text{Compound } (RFU \text{ final-initial}) - \text{DMSO control } (RFU \text{ final-initial})}{\text{NoBac } (RFU \text{ final-initial}) - \text{DMSO control } (RFU \text{ final-initial})} \times 100$$

Representative compounds of the invention, when tested in the above assay demonstrated percent inhibition of the CYP3A4 isozyme as set forth below in Table 8 wherein "A" refers to percent inhibition of less than 50% at 10 μM and "B" refers to percent inhibition of greater than 50% at 10 μM. The Example numbers provided in Table 8 correspond to the Examples herein:

TABLE 8

| Ex. No. | Compound Name | % Inhibition of CYP3A4 |
|---|---|---|
| 8 | 1'-{[(2S)-1-acetylpyrrolidin-2-yl]methyl}-5,6-dihydrospiro[benzo[1,2-b:5,4-b']difuran-3,3'-indol]-2'(1'H)-one | B |
| 11 | 2-(4'-chloro-2'-oxospiro[furo[2,3-f][1,3]benzodioxole-7,3'-indol]-1'(2'H)-yl)-N'-[(cyclopropylcarbonyl)oxy]ethanimidamide | B |
| 13 | 2-{3-[(2-oxo-5,6-dihydrospiro[benzo[1,2-b:5,4-b]difuran-3,3-indol]-1(2H)-yl)methyl]phenoxy}acetamide | B |

TABLE 8-continued

| Ex. No. | Compound Name | % Inhibition of CYP3A4 |
|---|---|---|
| 13.1 | 2-{4-[(2'-oxo-5,6-dihydrospiro[benzo[1,2-b:5,4-b']difuran-3,3'-indol]-1'(2'H)-yl)methyl]phenoxy}acetamide | A |
| 13.2 | 2-{4-[(2'-oxo-2,3-dihydrospiro[furo[2,3-g][1,4]benzodioxine-8,3'-indol]-1'(2'H)-yl)methyl]phenoxy}acetamide | B |
| 13.3 | 1'-[4-(2-methoxyethoxy)benzyl]-2,3-dihydrospiro[furo[2,3-g][1,4]benzodioxine-8,3'-indol]-2'(1'H)-one | B |
| 13.4 | 1'-{4-[2-(dimethylamino)ethoxy]benzyl}-2,3-dihydrospiro[furo[2,3-g][1,4]benzodioxine-8,3'-indol]-2'(1'H)-one | B |
| 14 | ethyl {3-[(2'-oxo-5,6-dihydrospiro[benzo[1,2-b:5,4-b']difuran-3,3'-indol]-1'(2'H)-yl)methyl]phenoxy}acetate | B |
| 14.1 | ethyl {4-[(2'-oxo-5,6-dihydrospiro[benzo[1,2-b:5,4-b']difuran-3,3'-indol]-1'(2'H)-yl)methyl]phenoxy}acetate | A |
| 14.2 | ethyl {4-[(2'-oxo-2,3-dihydrospiro[furo[2,3-g][1,4]benzodioxine-8,3'-indol]-1'(2'H)-yl)methyl]phenoxy}acetate | A |
| 15 | {3-[(2'-oxo-5,6-dihydrospiro[benzo[1,2-b:5,4-b']difuran-3,3'-indol]-1'(2'H)-yl)methyl]phenoxy}acetic acid | A |
| 15.1 | {4-[(2'-oxo-5,6-dihydrospiro[benzo[1,2-b:5,4-b']difuran-3,3'-indol]-1'(2'H)-yl)methyl]phenoxy}acetic acid | A |
| 15.2 | {4-[(2'-oxo-2,3-dihydrospiro[furo[2,3-g][1,4]benzodioxine-8,3'-indol]-1'(2'H)-yl)methyl]phenoxy}acetic acid | A |
| 15.3 | 1'-[4-(2-hydroxyethoxy)benzyl]-2,3-dihydrospiro[furo[2,3-g][1,4]benzodioxine-8,3'-indol]-2'(1'H)-one | A |
| 16 | N-methyl-2-{3-[(2'-oxo-5,6-dihydrospiro[benzo[1,2-b:5,4-b']difuran-3,3'-indol]-1'(2'H)-yl)methyl]phenoxy}acetamide | B |
| 17 | 1'-[4-(methylsulfinyl)benzyl]-5,6-dihydrospiro[benzo[1,2-b:5,4-b']difuran-3,3'-indol]-2'(1'H)-one | B |
| 18 | N-(methylsulfonyl)-N-{2'-oxo-1'-[(2R)-tetrahydrofuran-2-ylmethyl]-1',2'-dihydrospiro[1-benzofuran-3,3'-indol]-6-yl}methanesulfonamide | A |
| 20 | 6-(2-aminopropoxy)-1'-[(2R)-tetrahydrofuran-2-ylmethyl]spiro[1-benzofuran-3,3'-indol]-2'(1'H)-one hydrochloride | A |
| 21 | 6-[2-(dimethylamino)ethoxy]-1'-[(2R)-tetrahydrofuran-2-ylmethyl]spiro[1-benzofuran-3,3'-indol]-2'(1'H)-one | A |
| 24 | 1'-[(2R)-tetrahydrofuran-2-ylmethyl]spiro[benzo[1,2-b:5,4-b']difuran-3,3'-indole]-2',5(1'H,6H)-dione 5-oxime | B |
| 25 | (1Z)-N'-hydroxy-2-(2'-oxospiro[furo[2,3-f][1,3]benzodioxole-7,3'-indol]-1'(2'H)-yl)ethanimidamide | B |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

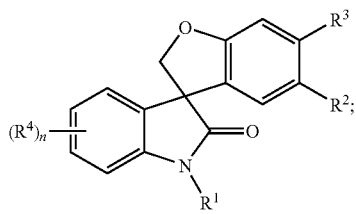

(I)

wherein:
n is 0, 1, 2, 3 or 4;
$R^1$ is selected from the group consisting of hydrogen, —$R^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—OR$^7$, —O—R$^5$—C(O)OR$^7$, —O—R$^5$—C(O)N(R$^7$)R$^8$, —O—R$^5$—N(R$^7$)R$^8$ and —S(O)R$^7$) and heterocyclylalkyl (optionally substituted with —C(O)R$^7$);
$R^2$ is hydrogen;
$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;
or $R^2$ and $R^3$, together with the carbons to which they are attached, form a fused O-heterocyclyl ring optionally substituted by —NOR$^7$;
$R^4$ is selected from the group consisting of alkyl, halo, haloalkyl, optionally substituted aryl and optionally substituted aralkyl;
each $R^5$ is independently selected from the group consisting of an optionally substituted straight or branched alkylene chain, an optionally substituted straight or branched alkenylene chain and an optionally substituted straight or branched alkynylene chain;
$R^6$ is selected from the group consisting of hydrogen and —C(O)R$^7$; and
each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;
as a stereoisomer, enantiomer or tautomer thereof or mixtures thereof;
or a pharmaceutically acceptable salt thereof.

2. The compound of claim 1 wherein:
n is 0, 1, 2, 3 or 4;
$R^1$ is selected from the group consisting of hydrogen, —$R^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—OR$^7$, —O—R$^5$—C(O)OR$^7$, —O—R$^5$—C(O)N(R$^7$)R$^8$, —O—R$^5$—N(R$^7$)R$^8$ and —S(O)R$^7$) and heterocyclylalkyl (optionally substituted with —C(O)R$^7$);
$R^2$ is hydrogen;
$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;
$R^4$ is selected from the group consisting of alkyl, halo, haloalkyl, aryl and aralkyl;
each $R^5$ is independently selected from the group consisting of an optionally substituted straight or branched alkylene chain, an optionally substituted straight or branched alkenylene chain and an optionally substituted straight or branched alkynylene chain;
$R^6$ is selected from the group consisting of hydrogen and —C(O)R$^7$; and
each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

3. The compound of claim 2 wherein:
n is 0;
$R^1$ is selected from the group consisting of hydrogen, —$R^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—OR$^7$, —O—R$^5$—C(O)OR$^7$, —O—R$^5$—C(O)N(R$^7$)R$^8$, —O—R$^5$—N(R$^7$)R$^8$ and —S(O)R$^7$) and heterocyclylalkyl (optionally substituted with —C(O)R$^7$);
$R^2$ is hydrogen;
$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;
each $R^5$ is an optionally substituted straight or branched alkylene chain;
$R^6$ is selected from the group consisting of hydrogen and —C(O)R$^7$; and
each $R^7$ and $R^8$ is independently selected from the group consisting of hydrogen, alkyl, haloalkyl, optionally substituted cycloalkyl and optionally substituted heterocyclyl.

4. The compound of claim 3 wherein:
n is 0;
$R^1$ is hydrogen;
$R^2$ is hydrogen;
$R^3$ is selected from the group consisting of —O—R$^5$—N(R$^7$)R$^8$ and —O—Si(R$^7$)$_3$;
$R^5$ is an optionally substituted straight or branched alkylene chain;
each $R^7$ and $R^8$ is independently selected from the group consisting of hydrogen, alkyl, haloalkyl, optionally substituted cycloalkyl and optionally substituted heterocyclyl.

5. The compound of claim 4 selected from the group consisting of:
6-[2-(dimethylamino)ethoxy]spiro[1-benzofuran-3,3'-indol]-2'(1'H)-one; and
6-{[tris(1-methylethyl)silyl]oxy}spiro[1-benzofuran-3,3'-indol]-2'(1'H)-one.

6. The compound of claim 3 wherein:
n is 0;
$R^1$ is diphenylmethyl;
$R^2$ is hydrogen;
$R^3$ is —O—R$^5$—N(R$^7$)R$^8$;
$R^5$ is an optionally substituted straight or branched alkylene chain;
$R^7$ and $R^8$ are each independently selected from the group consisting of hydrogen, alkyl, haloalkyl, optionally substituted cycloalkyl and optionally substituted heterocyclyl.

7. The compound of claim 6 wherein:
n is 0;
$R^1$ is diphenylmethyl;
$R^2$ is hydrogen;
$R^3$ is —O—R$^5$—N(R$^7$)R$^8$;
$R^5$ is an optionally substituted straight or branched alkylene chain;
$R^7$ and $R^8$ are each independently selected from the group consisting of hydrogen and alkyl.

8. The compound of claim 7 which is 6-[2-(dimethylamino)ethoxy]-1'-(diphenylmethyl)spiro[1-benzofuran-3,3'-indol]-2'(1'H)-one.

9. The compound of claim 3 wherein:
n is 0;
$R^1$ is heterocyclylalkyl (optionally substituted with —C(O)R$^7$);
$R^2$ is hydrogen;
$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;
each $R^5$ is an optionally substituted straight or branched alkylene chain; and
each $R^7$ and $R^8$ is independently selected from the group consisting of hydrogen, alkyl, haloalkyl, optionally substituted cycloalkyl and optionally substituted heterocyclyl.

10. The compound of claim 9 wherein:
n is 0;
$R^1$ is tetrahydrofuranylmethyl;
$R^2$ is hydrogen;
$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;
each $R^5$ is straight or branched alkylene chain; and
each $R^7$ and $R^8$ is independently selected from the group consisting of hydrogen and alkyl.

11. The compound of claim 10 selected from the group consisting of:
1'-[(2R)-tetrahydrofuran-2-ylmethyl]-6-{[tris(1-methylethyl)silyl]oxy}spiro[1-benzofuran-3,3'-indol]-2'(1'H)-one;
N-(methylsulfonyl)-N-{2'-oxo-1'-[(2R)-tetrahydrofuran-2-ylmethyl]-1',2'-dihydrospiro[1-benzofuran-3,3'-indol]-6-yl}methanesulfonamide;
tert-butyl[1-methyl-2-({2'-oxo-1'-[(2R)-tetrahydrofuran-2-ylmethyl]-1',2'-dihydrospiro[1-benzofuran-3,3'-indol]-6-yl}oxy)ethyl]carbamate;
6-(2-aminopropoxy)-1'-[(2R)-tetrahydrofuran-2-ylmethyl]spiro[1-benzofuran-3,3'-indol]-2'(1'H)-one hydrochloride;

6-[2-(dimethylamino)ethoxy]-1'-[(2R)-tetrahydrofuran-2-ylmethyl]spiro[1-benzofuran-3,3'-indol]-2'(1'H)-one;
methyl({2'-oxo-1'-[(2R)-tetrahydrofuran-2-ylmethyl]-1',2'-dihydrospiro[1-benzofuran-3,3'-indol]-6-yl}oxy)acetate; and
({2'-oxo-1'-[(2R)-tetrahydrofuran-2-ylmethyl]-1',2'-dihydrospiro[1-benzofuran-3,3'-indol]-6-yl}oxy)acetic acid.

12. The compound of claim 1 wherein:
n is 0, 1, 2, 3 or 4;
$R^1$ is selected from the group consisting of hydrogen, —$R^5$—C(=N$OR^6$)N($R^7$)$R^8$, diphenylmethyl, aralkyl (optionally substituted with a substituent selected from the group consisting of —N($R^7$)$R^8$, —C(=N$OR^6$)N($R^7$)$R^8$, —O—$R^5$—$OR^7$, —O—$R^5$—C(O)$OR^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);
$R^2$ and $R^3$, together with the carbons to which they are attached, form a fused O-heterocyclyl ring optionally substituted by =N$OR^7$;
$R^4$ is selected from the group consisting of alkyl, halo, haloalkyl, optionally substituted aryl and optionally substituted aralkyl;
each $R^5$ is independently selected from the group consisting of an optionally substituted straight or branched alkylene chain, an optionally substituted straight or branched alkenylene chain and an optionally substituted straight or branched alkynylene chain;
$R^6$ is selected from the group consisting of hydrogen and —C(O)$R^7$; and
each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

13. The compound of claim 12 wherein:
n is 0 or 1;
$R^1$ is selected from the group consisting of hydrogen, —$R^5$—C(=N$OR^6$)N($R^7$)$R^8$, diphenylmethyl, aralkyl (optionally substituted with a substituent selected from the group consisting of —N($R^7$)$R^8$, —C(=N$OR^6$)N($R^7$)$R^8$, —O—$R^5$—$OR^7$, —O—$R^5$—C(O)$OR^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);
$R^2$ and $R^3$, together with the carbons to which they are attached, form a fused O-heterocyclyl ring optionally substituted by =N$OR^7$;
$R^4$ is selected from the group consisting of alkyl, halo, haloalkyl, optionally substituted aryl and optionally substituted aralkyl;
each $R^5$ is independently selected from the group consisting of an optionally substituted straight or branched alkylene chain, an optionally substituted straight or branched alkenylene chain and an optionally substituted straight or branched alkynylene chain;
$R^6$ is selected from the group consisting of hydrogen and —C(O)$R^7$; and
each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

14. The compound of claim 13 wherein:
n is 0 or 1;
$R^1$ is selected from the group consisting of hydrogen, —$R^5$—C(=N$OR^6$)N($R^7$)$R^8$, diphenylmethyl, aralkyl (optionally substituted with a substituent selected from the group consisting of —N($R^7$)$R^8$, —C(=N$OR^6$)N($R^7$)$R^8$, —O—$R^5$—$OR^7$, —O—$R^5$—C(O)$OR^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);
$R^2$ and $R^3$, together with the carbons to which they are attached, form a fused [1,3]-dioxolyl;
$R^4$ is selected from the group consisting of alkyl, halo, haloalkyl, optionally substituted aryl and optionally substituted aralkyl;
each $R^5$ is independently selected from the group consisting of an optionally substituted straight or branched alkylene chain, an optionally substituted straight or branched alkenylene chain and an optionally substituted straight or branched alkynylene chain;
$R^6$ is selected from the group consisting of hydrogen and —C(O)$R^7$; and
each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

15. The compound of claim 14 wherein:
n is 0 or 1;
$R^1$ is —$R^5$—C(=N$OR^6$)N($R^7$)$R^8$;
$R^2$ and $R^3$, together with the carbons to which they are attached, form a fused [1,3]-dioxolyl;
$R^4$ is halo;
$R^5$ is an optionally substituted straight or branched alkylene chain;
$R^6$ is selected from the group consisting of hydrogen and —C(O)$R^7$; and
each $R^7$ and $R^8$ is independently selected from the group consisting of hydrogen, alkyl and optionally substituted cycloalkyl.

16. The compound of claim 15 selected from the group consisting of:
N'-hydroxy-3-(2'-oxo-6H-spiro[benzofuro[6,5-d][1,3]dioxole-7,3'-indoline]-1'-yl)propanimidamide;
2-(4'-chloro-2'-oxospiro[furo[2,3-f][1,3]benzodioxole-7,3'-indol]-1'(2'H)-yl)-N'-[(cyclopropylcarbonyl)oxy]ethanimidamide; and
(1Z)-N'-hydroxy-2-(2'-oxospiro[furo[2,3-f][1,3]benzodioxole-7,3'-indol]-1'(2'H)-yl)ethanimidamide.

17. The compound of claim 14 wherein:
n is 0;
$R^1$ is aralkyl optionally substituted with —N($R^7$)$R^8$;
$R^2$ and $R^3$, together with the carbons to which they are attached, form a fused [1,3]-dioxolyl;
each $R^5$ is independently selected from the group consisting of an optionally substituted straight or branched alkylene chain; and
each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl.

18. The compound of claim 17 wherein:
n is 0;
$R^1$ is benzyl optionally substituted with —N($R^7$)$R^8$;
$R^2$ and $R^3$, together with the carbons to which they are attached, form a fused [1,3]-dioxolyl;

$R^7$ and $R^8$ are each independently selected from the group consisting of hydrogen and optionally substituted pyrrolidinyl.

19. The compound of claim 18 selected from the group consisting of:
   tert-butyl (3R)-3-({4-[(2'-oxospiro[furo[2,3-f][1,3]benzodioxole-7,3'-indol]-1'(2'H)-yl)methyl]phenyl}-amino)pyrrolidine-1-carboxylate;
   1'-{4-[(3R)-pyrrolidin-3-ylamino]benzyl}spiro[furo[2,3-f][1,3]benzodioxole-7,3'-indol]-2'(1'H)-one, and
   1'-{4-[(3R)-pyrrolidin-3-ylamino]benzyl}spiro[furo[2,3-f][1,3]benzodioxole-7,3'-indol]-2'(1'H)-one hydrochloride.

20. The compound of claim 13 wherein:
   n is 0;
   $R^1$ is aralkyl (optionally substituted with a substituent selected from the group consisting of —$N(R^7)R^8$, —$C(=NOR^6)N(R^7)R^8$, —O—$R^5$—$OR^7$, —O—$R^5$—$C(O)OR^7$, —O—$R^5$—$C(O)N(R^7)R^8$, —O—$R^5$—$N(R^7)R^8$ and —$S(O)R^7$) and heterocyclylalkyl (optionally substituted with —$C(O)R^7$);
   $R^2$ and $R^3$, together with the carbons to which they are attached, form a fused dihydrofuranyl optionally substituted by =$NOR^7$;
   each $R^5$ is independently an optionally substituted straight or branched alkylene chain;
   $R^6$ is selected from the group consisting of hydrogen and —$C(O)R^7$; and
   each $R^7$ and $R^8$ is independently selected from the group consisting of hydrogen and alkyl.

21. The compound of claim 20 wherein:
   n is 0;
   $R^1$ is benzyl optionally substituted with a substituent selected from the group consisting of —$N(R^7)R^8$, —$C(=NOR^6)N(R^7)R^8$, —O—$R^5$—$OR^7$, —O—$R^5$—$C(O)OR^7$, —O—$R^5$—$C(O)N(R^7)R^8$, —O—$R^5$—$N(R^7)R^8$ and —$S(O)R^7$;
   $R^2$ and $R^3$, together with the carbons to which they are attached, form a fused dihydrofuranyl optionally substituted by =$NOR^7$;
   each $R^5$ is independently an optionally substituted straight or branched alkylene chain;
   $R^6$ is selected from the group consisting of hydrogen and —$C(O)R^7$; and
   each $R^7$ and $R^8$ is independently selected from the group consisting of hydrogen and alkyl.

22. The compound of claim 21 selected from the group consisting of:
   N'-hydroxy-4-[(2'-oxo-5,6-dihydrospiro[benzo[1,2-b:5,4-b']difuran-3,3'-indol]-1'(2'H)-yl)methyl]benzenecarboximidamide;
   N'-hydroxy-3-[(2'-oxo-5,6-dihydrospiro[benzo[1,2-b:5,4-b']difuran-3,3'-indol]-1'(2'H)-yl)methyl]benzenecarboximidamide;
   2-{3-[(2-oxo-5,6-dihydrospiro[benzo[1,2-b:5,4-b']difuran-3,3-indol]-1'(2H)-yl)methyl]phenoxy}acetamide;
   2-{4-[(2'-oxo-5,6-dihydrospiro[benzo[1,2-b:5,4-b']difuran-3,3'-indol]-1'(2'H)-yl)methyl]phenoxy}acetamide;
   ethyl {3-[(2'-oxo-5,6-dihydrospiro[benzo[1,2-b:5,4-b']difuran-3,3-indol]-1'(2'H)-yl)methyl]phenoxy}acetate;
   {3-[(2'-oxo-5,6-dihydrospiro[benzo[1,2-b:5,4-b']difuran-3,3-indol]-1'(2'H)-yl)methyl]phenoxy}acetic acid;
   2-(4-((2'-oxo-5,6-dihydro-2H-spiro[benzofuro[6,5-b']difuran-3,3'-indoline]-1'-yl)methyl)phenoxy)acetic acid;
   N-methyl-2-{3-[(2'-oxo-5,6-dihydrospiro[benzo[1,2-b:5,4-b']difuran-3,3-indol]-1'(2'H)-yl)methyl]phenoxy}acetamide; and
   1'-[4-(methylsulfinyl)benzyl]-5,6-dihydrospiro[benzo[1,2-b:5,4-b']difuran-3,3'-indol]-2'(1'H)-one.

23. The compound of claim 20 wherein:
   n is 0;
   $R^1$ is independently selected from the group consisting of pyrrolidin-2-ylmethyl (optionally substituted with —$C(O)R^7$) and tetrahydrofuran-2-ylmethyl;
   $R^2$ and $R^3$, together with the carbons to which they are attached, form a fused dihydrofuranyl optionally substituted by =$NOR^7$;
   each $R^5$ is independently an optionally substituted straight or branched alkylene chain;
   each $R^7$ is independently selected from the group consisting of hydrogen and alkyl.

24. The compound of claim 23 selected from the group consisting of:
   1'-{[(2S)-1-acetylpyrrolidin-2-yl]methyl}-5,6-dihydrospiro[benzo[1,2-b:5,4-b']difuran-3,3'-indol]-2'(1'H)-one; and
   1'-[(2R)-tetrahydrofuran-2-ylmethyl]spiro[benzo[1,2-b:5,4-b']difuran-3,3'-indole]-2',5(1'H,6H)-dione 5-oxime.

25. The compound of claim 13 wherein:
   n is 0;
   $R^1$ is aralkyl (optionally substituted with a substituent selected from the group consisting of —$N(R^7)R^8$, —$C(=NOR^6)N(R^7)R^8$, —O—$R^5$—$OR^7$, —O—$R^5$—$C(O)OR^7$, —O—$R^5$—$C(O)N(R^7)R^8$, —O—$R^5$—$N(R^7)R^8$ and —$S(O)R^7$) and heterocyclylalkyl (optionally substituted with —$C(O)R^7$);
   $R^2$ and $R^3$, together with the carbons to which they are attached, form a fused [1,4]-dioxinyl;
   each $R^5$ is independently an optionally substituted straight or branched alkylene chain;
   $R^6$ is selected from the group consisting of hydrogen and —$C(O)R^7$; and
   each $R^7$ and $R^8$ is independently selected from the group consisting of hydrogen and alkyl.

26. The compound of claim 25 wherein:
   n is 0;
   $R^1$ is benzyl optionally substituted with a substituent selected from the group consisting of —$N(R^7)R^8$, —$C(=NOR^6)N(R^7)R^8$, —O—$R^5$—$OR^7$, —O—$R^5$—$C(O)OR^7$, —O—$R^5$—$C(O)N(R^7)R^8$, —O—$R^5$—$N(R^7)R^8$ and —$S(O)R^7$;
   $R^2$ and $R^3$, together with the carbons to which they are attached, form a fused [1,4]-dioxinyl;
   each $R^5$ is independently an optionally substituted straight or branched alkylene chain;
   $R^6$ is selected from the group consisting of hydrogen and —$C(O)R^7$; and
   each $R^7$ and $R^8$ is independently selected from the group consisting of hydrogen and alkyl.

27. The compound of claim 26 selected from the group consisting of:
   2-{4-[(2'-oxo-2,3-dihydrospiro[furo[2,3-g][1,4]benzodioxine-8,3'-indol]-1'(2'H)-yl)methyl]phenoxy}acetamide;
   1'-[4-(2-methoxyethoxy)benzyl]-2,3-dihydrospiro[furo[2,3-g][1,4]benzodioxine-8,3'-indol]-2'(1'H)-one;
   1'-{4-[2-(dimethylamino)ethoxy]benzyl}-2,3-dihydrospiro[furo[2,3-g][1,4]benzodioxine-8,3'-indol]-2'(1'H)-one;
   ethyl {4-[(2'-oxo-2,3-dihydrospiro[furo[2,3-g][1,4]benzodioxine-8,3'-indol]-1'(2'H)-yl)methyl]phenoxy}acetate;

{4-[(2'-oxo-2,3-dihydrospiro[furo[2,3-g][1,4]benzodioxine-8,3'-indol]-1'(2'H)-yl)methyl]phenoxy}acetic acid; and 1'-[4-(2-hydroxyethoxy)benzyl]-2,3-dihydrospiro[furo[2,3-g][1,4]benzodioxine-8,3'-indol]-2'(1'H)-one.

28. A pharmaceutical composition comprising a pharmaceutically acceptable excipient and a compound of formula (I):

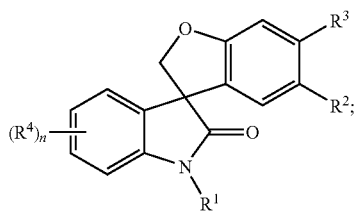

(I)

wherein:

n is 0, 1, 2, 3 or 4;

$R^1$ is hydrogen, —$R^5$—C(=NO$R^6$)N($R^7$)$R^8$, diphenylmethyl, aralkyl (optionally substituted with a substituent selected from the group consisting of —N($R^7$)$R^8$, —C(=NO$R^6$)N($R^7$)$R^8$, —O—$R^5$—O$R^7$, —O—$R^5$—C(O)O$R^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);

$R^2$ is hydrogen;

$R^3$ is selected from the group consisting of —O—$R^5$—N($R^7$)$R^8$, —O—$R^5$—N($R^7$)C(O)O$R^8$, —O—$R^5$—C(O)O$R^7$, —O—Si($R^7$)$_3$ and —N[S(O)$_2R^7$]$_2$;

or $R^2$ and $R^3$, together with the carbons to which they are attached, form a fused O-heterocyclyl ring optionally substituted by =NO$R^7$;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)$R^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

29. A method of treating or ameliorating, but not preventing, pain in a mammal, and combinations thereof, wherein the method comprises administering to the mammal in need thereof a therapeutically effective amount of a compound of formula (I):

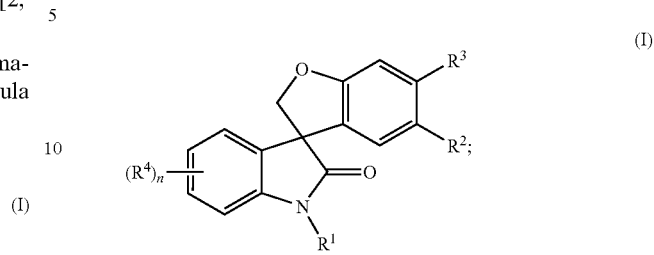

(I)

wherein:

n is 0, 1, 2, 3 or 4;

$R^1$ is hydrogen, —$R^5$—C(=NO$R^6$)N($R^7$)$R^8$, diphenylmethyl, aralkyl (optionally substituted with a substituent selected from the group consisting of —N($R^7$)$R^8$, —C(=NO$R^6$)N($R^7$)$R^8$, —O—$R^5$—O$R^7$, —O—$R^5$—C(O)O$R^7$, —O—$R^5$—C(O)N($R^7$)$R^8$, —O—$R^5$—N($R^7$)$R^8$ and —S(O)$R^7$) and heterocyclylalkyl (optionally substituted with —C(O)$R^7$);

$R^2$ is hydrogen;

$R^3$ is selected from the group consisting of —O—$R^5$—N($R^7$)$R^8$, —O—$R^5$—N($R^7$)C(O)O$R^8$, —O—$R^5$—C(O)O$R^7$, —O—Si($R^7$)$_3$ and —N[S(O)$_2R^7$]$_2$;

or $R^2$ and $R^3$, together with the carbons to which they are attached, form a fused O-heterocyclyl ring optionally substituted by =NO$R^7$;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)$R^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

30. The method of claim 29, wherein the pain is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury, and combinations thereof.

31. The method of claim 29, wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis, diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, cancer, epilepsy, partial and general tonic seizures, restless leg syndrome, arrhythmias, ischaemic conditions caused by stroke or neural trauma, tachy-arrhythmias, atrial fibrillation and ventricular fibrillation.

32. A method of treating but not preventing pain in a mammal by the inhibition of ion flux through a voltage-dependent sodium channel in the mammal, wherein the method comprises administering to the mammal in need thereof a therapeutically effective amount of a compound selected from formula (I):

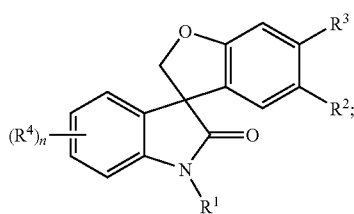

(I)

wherein:

n is 0, 1, 2, 3 or 4;

$R^1$ is hydrogen, —$R^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—OR$^7$, —O—R$^5$—C(O)OR$^7$, —O—R$^5$—C(O)N(R$^7$)R$^8$, —O—R$^5$—N(R$^7$)R$^8$ and —S(O)R$^7$) and heterocyclylalkyl (optionally substituted with —C(O)R$^7$);

$R^2$ is hydrogen;

$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;

or $R^2$ and $R^3$, together with the carbons to which they are attached, form a fused O-heterocyclyl ring optionally substituted by =NOR$^7$;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)R$^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

33. A method of decreasing ion flux through a voltage-dependent sodium channel in a cell in a mammal, wherein the method comprises contacting the cell with a compound selected from formula (I):

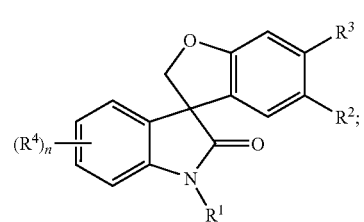

(I)

wherein:

n is 0, 1, 2, 3 or 4;

$R^1$ is hydrogen, —$R^5$—C(=NOR$^6$)N(R$^7$)R$^8$, diphenylmethyl, aralkyl (optionally substituted with a substituent selected from the group consisting of —N(R$^7$)R$^8$, —C(=NOR$^6$)N(R$^7$)R$^8$, —O—R$^5$—OR$^7$, —O—R$^5$—C(O)OR$^7$, —O—R$^5$—C(O)N(R$^7$)R$^8$, —O—R$^5$—N(R$^7$)R$^8$ and —S(O)R$^7$) and heterocyclylalkyl (optionally substituted with —C(O)R$^7$);

$R^2$ is hydrogen;

$R^3$ is selected from the group consisting of —O—R$^5$—N(R$^7$)R$^8$, —O—R$^5$—N(R$^7$)C(O)OR$^8$, —O—R$^5$—C(O)OR$^7$, —O—Si(R$^7$)$_3$ and —N[S(O)$_2$R$^7$]$_2$;

or $R^2$ and $R^3$, together with the carbons to which they are attached, form a fused O-heterocyclyl ring optionally substituted by =NOR$^7$;

$R^4$ is selected from the group consisting of alkyl, halo, haloalkyl, optionally substituted aryl and optionally substituted aralkyl;

each $R^5$ is independently selected from the group consisting of an optionally substituted straight or branched alkylene chain, an optionally substituted straight or branched alkenylene chain and an optionally substituted straight or branched alkynylene chain;

$R^6$ is selected from the group consisting of hydrogen and —C(O)R$^7$; and each $R^7$ and $R^8$ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

34. A method of treating, but not preventing, hypercholesterolemia in a mammal, wherein the method comprises administering to the mammal in need thereof a therapeutically effective amount of a compound selected from formula (I):

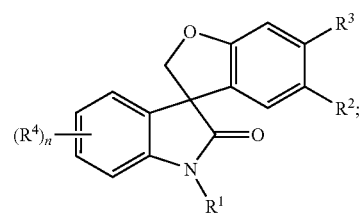

(I)

wherein:

n is 0, 1, 2, 3 or 4;

$R^1$ is hydrogen, —$R^5$—C(=NOR$^6$)N(R$^7$)R$^8$, diphenylmethyl, aralkyl (optionally substituted with a substituent selected from the group consisting of —N(R$^7$)R$^8$, —C(=NOR⁶)N(R⁷)R⁸, —O—R⁵—OR⁷, —O—R⁵—C(O)OR⁷, —O—R⁵—C(O)N(R⁷)R⁸, —O—R⁵—N(R⁷)R⁸ and —S(O)R⁷) and heterocyclylalkyl (optionally substituted with —C(O)R⁷);

R² is hydrogen;

R³ is selected from the group consisting of —O—R⁵—N(R⁷)R⁸, —O—R⁵—N(R⁷)C(O)OR⁸, —O—R⁵—C(O)OR⁷, —O—Si(R⁷)₃ and —N[S(O)₂R⁷]₂;

or R² and R³, together with the carbons to which they are attached, form a fused O-heterocyclyl ring optionally substituted by =NOR⁷;

R⁴ is selected from the group consisting of alkyl, halo, haloalkyl, optionally substituted aryl and optionally substituted aralkyl;

each R⁵ is independently selected from the group consisting of an optionally substituted straight or branched alkylene chain, an optionally substituted straight or branched alkenylene chain and an optionally substituted straight or branched alkynylene chain;

R⁶ is selected from the group consisting of hydrogen and —C(O)R⁷; and each R⁷ and R⁸ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

35. A method of treating, but not preventing, benign prostatic hyperplasia in a mammal, wherein the method comprises administering to the mammal in need thereof a therapeutically effective amount of a compound selected from formula (I):

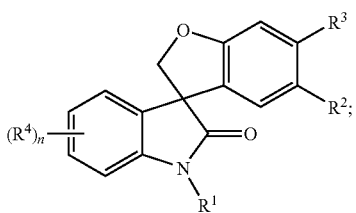

(I)

wherein:

n is 0, 1, 2, 3 or 4;

R¹ is hydrogen, —R⁵—C(=NOR⁶)N(R⁷)R⁸, diphenylmethyl, aralkyl (optionally substituted with a substituent selected from the group consisting of —N(R⁷)R⁸, —C(=NOR⁶)N(R⁷)R⁸, —O—R⁵—OR⁷, —O—R⁵—C(O)OR⁷, —O—R⁵—C(O)N(R⁷)R⁸, —O—R⁵—N(R⁷)R⁸ and —S(O)R⁷) and heterocyclylalkyl (optionally substituted with —C(O)R⁷);

R² is hydrogen;

R³ is selected from the group consisting of —O—R⁵—N(R⁷)R⁸, —O—R⁵—N(R⁷)C(O)OR⁸, —O—R⁵—C(O)OR⁷, —O—Si(R⁷)₃ and —N[S(O)₂R⁷]₂;

or R² and R³, together with the carbons to which they are attached, form a fused O-heterocyclyl ring optionally substituted by =NOR⁷;

R⁴ is selected from the group consisting of alkyl, halo, haloalkyl, optionally substituted aryl and optionally substituted aralkyl;

each R⁵ is independently selected from the group consisting of an optionally substituted straight or branched alkylene chain, an optionally substituted straight or branched alkenylene chain and an optionally substituted straight or branched alkynylene chain;

R⁶ is selected from the group consisting of hydrogen and —C(O)R⁷; and each R⁷ and R⁸ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

36. A method of treating, but not preventing, pruritis in a mammal, wherein the method comprises administering to the mammal in need thereof a therapeutically effective amount of a compound selected from formula (I):

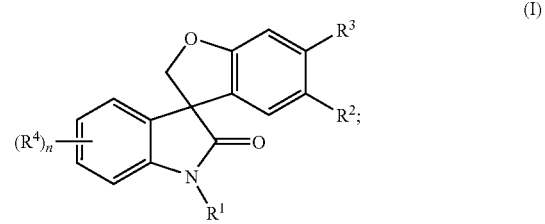

(I)

wherein:

n is 0, 1, 2, 3 or 4;

R¹ is hydrogen, —R⁵—C(=NOR⁶)N(R⁷)R⁸, diphenylmethyl, aralkyl (optionally substituted with a substituent selected from the group consisting of —N(R⁷)R⁸, —C(=NOR⁶)N(R⁷)R⁸, —O—R⁵—OR⁷, —O—R⁵—C(O)OR⁷, —O—R⁵—C(O)N(R⁷)R⁸, —O—R⁵—N(R⁷)R⁸ and —S(O)R⁷) and heterocyclylalkyl (optionally substituted with —C(O)R⁷);

R² is hydrogen;

R³ is selected from the group consisting of —O—R⁵—N(R⁷)R⁸, —O—R⁵—N(R⁷)C(O)OR⁸, —O—R⁵—C(O)OR⁷, —O—Si(R⁷)₃ and —N[S(O)₂R⁷]₂;

or R² and R³, together with the carbons to which they are attached, form a fused O-heterocyclyl ring optionally substituted by =NOR⁷;

R⁴ is selected from the group consisting of alkyl, halo, haloalkyl, optionally substituted aryl and optionally substituted aralkyl;

each R⁵ is independently selected from the group consisting of an optionally substituted straight or branched alkylene chain, an optionally substituted straight or branched alkenylene chain and an optionally substituted straight or branched alkynylene chain;

R⁶ is selected from the group consisting of hydrogen and —C(O)R⁷; and each R⁷ and R⁸ is independently selected from the group consisting of hydrogen, alkyl, haloalkyl, optionally substituted aryl, optionally substituted aralkyl, optionally substituted cycloalkyl, optionally substituted cycloalkylalkyl, and optionally substituted heterocyclyl;

as a stereoisomer, enantiomer or tautomer thereof or mixtures thereof;

or a pharmaceutically acceptable salt thereof.

37. The method of claim 29 wherein the pain is selected from trigeminal neuralgia, post-herpetic neuralgia, eudynia, familial erythromelalgia, primary erythromelalgia, familial rectal pain or fibromyalgia.

* * * * *